(12) United States Patent
Shapiro et al.

(10) Patent No.: US 9,631,192 B2
(45) Date of Patent: Apr. 25, 2017

(54) AUTO-RECOGNIZING THERAPEUTIC RNA/DNA CHIMERIC NANOPARTICLES (NP)

(71) Applicant: The United States of America, as represented by the Secretary, Department of Health & Human Services, Washington, DC (US)

(72) Inventors: Bruce A. Shapiro, Gaithersburg, MD (US); Kirill A. Afonin, Frederick, MD (US); Mathias D. Viard, Frederick, MD (US); Eckart H. Bindewald, Frederick, MD (US); Luc Jaeger, Goleta, CA (US); Arti N. Santhanam, Elliott City, MD (US)

(73) Assignees: The United States of America, as represented by the Secretary, Department of Health & Human Services, Washington, DC (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 14/358,942

(22) PCT Filed: Nov. 19, 2012

(86) PCT No.: PCT/US2012/065945
§ 371 (c)(1),
(2) Date: May 16, 2014

(87) PCT Pub. No.: WO2013/075140
PCT Pub. Date: May 23, 2013

(65) Prior Publication Data
US 2014/0303237 A1    Oct. 9, 2014

Related U.S. Application Data

(60) Provisional application No. 61/698,113, filed on Sep. 7, 2012, provisional application No. 61/561,257, filed on Nov. 17, 2011.

(51) Int. Cl.
| | | |
|---|---|---|
| C07H 21/02 | (2006.01) | |
| C07H 21/04 | (2006.01) | |
| A61K 48/00 | (2006.01) | |
| C12N 15/113 | (2010.01) | |
| C12N 15/11 | (2006.01) | |

(52) U.S. Cl.
CPC .......... *C12N 15/113* (2013.01); *C12N 15/111* (2013.01); *C12N 15/1132* (2013.01); *C12N 15/1135* (2013.01); *C12N 2310/14* (2013.01); *C12N 2310/16* (2013.01); *C12N 2310/322* (2013.01); *C12N 2310/3519* (2013.01); *C12N 2320/51* (2013.01)

(58) Field of Classification Search
CPC ............................ C12N 15/111; C12N 15/113
See application file for complete search history.

(56) References Cited

U.S. PATENT DOCUMENTS

| | | | | |
|---|---|---|---|---|
| 7,820,809 B2 * | 10/2010 | Khvorova | ............ | A61K 31/713 435/6.1 |
| 8,871,199 B2 * | 10/2014 | Centeno | ................. | A61K 35/16 424/145.1 |

FOREIGN PATENT DOCUMENTS

WO    2004022771 A2    3/2004

OTHER PUBLICATIONS

Hogrefe et al., "Chemically Modified Short Interfering Hybrids (siHYBRIDS): Nanoimmunoliposome Delivery In Vitro and In Vivo for RNAi of HER-2", Nucleosides, Nucleotides, and Nucleic Acids, vol. 25, No. 8, pp. 889-907 (2006).
Hoerter et al., "siRNA-Like Double-Stranded RNAs Are Specifically Protected Against Degredation in Human Cell Extract", Plus One, vol. 6, No. 5, p. E20359 (2011).
Ui-Tei et al., "Functional dissection of siRNA sequence by systematic DNA seed arm is a powerful tool for mammalian gene silencing with significantly reduced off-target effect", Nucleic Acid Research, vol. 36, No. 7, pp. 2136-2151 (2008).

\* cited by examiner

*Primary Examiner* — Amy Bowman
(74) *Attorney, Agent, or Firm* — Locke Lord LLP; Gabriel J. McCool

(57) ABSTRACT

Auto-recognizing therapeutic R/DNA chimeric nanoparticles (R/DNA NP) are described that are pairs of DNA/RNA hybrids where the DNA molecules have complementary toehold sequences that promote the re-association of the R/DNA NPs when mixed resulting in the formation of RNA/RNA duplexes that act as siRNAs.

22 Claims, 61 Drawing Sheets

From Rose et al., Nucleic Acids Research, 2005, Vol. 33, No. 13:
EGFPS1 25D/27:
5'  pACCCUGAAGUUCAUCUGCACCACcg   EGFPS1 R 25D/27 (SEQ ID NO: 58)
3'  ACUGGGACUUCAAGUAGACGUGGUGC (SEQ ID NO: 59)
sense
5' - pACCCUGAAGUUCAUCUGCACCACCG (SEQ ID NO: 2)
antisense
5' - CGGUGGUGCAGAUGAACUUCAGGGUCA (SEQ ID NO: 3)

Complementary to each ssRNA DNA strand with toeholds:
DNA for sense
5' - GGAGACCGTGACCGGTGGTGCAGATGAACTTCAGGGTCA (SEQ ID NO: 60)

DNA for antisense
5' - TGACCCTGAAGTTCATCTGCACCACCGGTCACGGTCTCC (SEQ ID NO: 61)

Figure 9

Two individual hybrids (ΔG ~ - 85.405 kcal/mol)

ΔG(R/DNA hybrid) ~ (ΔG(DNA duplex) + ΔG(RNAduplex))/2
ΔG(hybrid 1) ~ -42.075 kcal/mol    ΔG(hybrid2) ~ -43.33 kcal/mol

SEQUENCE LISTING

```
<160> NUMBER OF SEQ ID NOS: 61

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Val Val Pro Pro
1               5

<210> SEQ ID NO 2
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phosphorylated base

<400> SEQUENCE: 2
acccugaagu ucaucugcac caccg                                           25

<210> SEQ ID NO 3
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
```

```
cgguggugca gaugaacuuc aggguca                                          27

<210> SEQ ID NO 4
<211> LENGTH: 12
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phosphorylated base

<400> SEQUENCE: 4
acccugaagu uc                                                          12

<210> SEQ ID NO 5
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
aucugcacca ccg                                                         13

<210> SEQ ID NO 6
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phosphorylated base

<400> SEQUENCE: 6
acccugaagu ucaucugcac c                                                21

<210> SEQ ID NO 7
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
ugcagaugaa cuucaggguc a                                                21

<210> SEQ ID NO 8
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phosphorylated base

<400> SEQUENCE: 8
gagcagauga uacaguauua gaaga                                            25
```

```
<210> SEQ ID NO 9
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
ucuucuaaua cuguaucauc ugcuccu                                           27

<210> SEQ ID NO 10
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
ggacaauugg agaagugaau uauauu                                            26

<210> SEQ ID NO 11
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phosphorylated base

<400> SEQUENCE: 11
uauaauucac uucuccaauu gucc                                              24

<210> SEQ ID NO 12
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phosphorylated base

<400> SEQUENCE: 12
aaggaugacu augugaaggc acugc                                             25

<210> SEQ ID NO 13
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
gcagugccuu cacauaguca uccuugc                                           27

<210> SEQ ID NO 14
<211> LENGTH: 39
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 14
ggagaccgtg accggtggtg cagatgaact tcagggtca                                 39

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tgaccctgaa gttcatctgc accaccggtc acggtctcc                                 39

<210> SEQ ID NO 16
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggagaccgtg acagtgatta cggtggtgca gatgaacttc agggtca                        47

<210> SEQ ID NO 17
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tgaccctgaa gttcatctgc accaccgtaa tcactgtcac ggtctcc                        47

<210> SEQ ID NO 18
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ggagaccgtg acagtgatta gattacactc cggtggtgca gatgaacttc agggtca             57

<210> SEQ ID NO 19
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tgaccctgaa gttcatctgc accaccggag tgtaatctaa tcactgtcac ggtctcc             57

<210> SEQ ID NO 20
<211> LENGTH: 41
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 20
agucuucuaa uacuguauca ucugcuccug tcacggtctc c                41

<210> SEQ ID NO 21
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 21
ggagaccgtg acgagcagau gauacaguau uagaaga                37

<210> SEQ ID NO 22
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
aatataattc acttctccaa ttgtccgtca cggtctcc                38

<210> SEQ ID NO 23
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
ggagaccgtg acggacaatt ggagaagtga attatatt                38

<210> SEQ ID NO 24
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
ggagaccgtg actggaggaa atgaacaagt agataaat                38

<210> SEQ ID NO 25
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gcagtgcctt cacatagtca tccttgcgtc acggtctcc                39

<210> SEQ ID NO 26

```
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ggagaccgtg acgcaaggat gactatgtga aggcactgc                              39

<210> SEQ ID NO 27
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 27
acccugaagu ucaucugcac caccg                                             25

<210> SEQ ID NO 28
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
ggagaccgtg accggtggtg cagatgaact tcagggtcat t                           41

<210> SEQ ID NO 29
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aatgaccctg aagttcatct gcaccaccgg tcacggtctc c                           41

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
aatgaccctg aagttcatct gcaccaccg                                         29

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
accctgaagt tcatctgcac caccg                                             25

<210> SEQ ID NO 32
<211> LENGTH: 21
```

<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phosphorylated base

<400> SEQUENCE: 32
ugcagaugaa cuucaggguc a                                             21

<210> SEQ ID NO 33
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 33
uaugacaugg uaacgaauga caguau                                        26

<210> SEQ ID NO 34
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
auacuguccg acaugucaua                                               20

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ggagaccgtg acggtgcaga tgaacttcag ggtca                              35

<210> SEQ ID NO 36
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
tgaccctgaa gttcatctgc accgtcacgg tctcc                              35

<210> SEQ ID NO 37
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
ggagaccgtg acatactgtc attcgttacc atgtcatagc atg                     43

<210> SEQ ID NO 38
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 38
catgctatga catgtcggac agtatgtcac ggtctcc                               37

<210> SEQ ID NO 39
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
ggagaccgtg acggtgcaga tgaacttcag ggtcaatact gtcattcgtt accatgtcat      60
agcatg                                                                66

<210> SEQ ID NO 40
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
catgctatga catgtcggac agtattgacc ctgaagttca tctgcaccgt cacggtctcc      60

<210> SEQ ID NO 41
<211> LENGTH: 66
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
ggagaccgtg acatactgtc attcgttacc atgtcatagc atgggtgcag atgaacttca      60
gggtca                                                                66

<210> SEQ ID NO 42
<211> LENGTH: 60
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
tgaccctgaa gttcatctgc acccatgcta tgacatgtcg acagtatgt cacggtctcc      60

<210> SEQ ID NO 43
<211> LENGTH: 58
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43

```
ggagaccgtg acggtgcaga tgaacttcag ggtcaggtgc agatgaactt cagggtca      58
```

<210> SEQ ID NO 44
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44

```
tgaccctgaa gttcatctgc acctgaccct gaagttcatc tgcaccgtca cggtctcc      58
```

<210> SEQ ID NO 45
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45

```
ggagaccgtg acggtgcaga tgaacttcag ggtcaggtgc agatgaactt cagggtcaat      60
actgtcattc gttaccatgt catagcatg                                        89
```

<210> SEQ ID NO 46
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46

```
catgctatga catgtcggac agtattgacc ctgaagttca tctgcacctg accctgaagt      60
tcatctgcac cgtcacggtc tcc                                              83
```

<210> SEQ ID NO 47
<211> LENGTH: 89
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47

```
ggagaccgtg acggtgcaga tgaacttcag ggtcaatact gtcattcgtt accatgtcat      60
agcatgggtg cagatgaact tcagggtca                                        89
```

<210> SEQ ID NO 48
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48

```
tgaccctgaa gttcatctgc acccatgcta tgacatgtcg gacagtattg accctgaagt      60
tcatctgcac cgtcacggtc tcc                                              83
```

<210> SEQ ID NO 49
<211> LENGTH: 89

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
ggagaccgtg acatactgtc attcgttacc atgtcatagc atgggtgcag atgaacttca     60
gggtcaggtg cagatgaact tcagggtca                                      89

<210> SEQ ID NO 50
<211> LENGTH: 83
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
tgaccctgaa gttcatctgc acctgaccct gaagttcatc tgcacccatg ctatgacatg     60
tcggacagta tgtcacggtc tcc                                            83

<210> SEQ ID NO 51
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ggagaccgtg acggtgcaga tgaacttcag ggtcaggtgc agatgaactt cagggtcagg     60
tgcagatgaa cttcagggtc a                                              81

<210> SEQ ID NO 52
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
tgaccctgaa gttcatctgc acctgaccct gaagttcatc tgcacctgac cctgaagttc     60
atctgcaccg tcacggtctc c                                              81

<210> SEQ ID NO 53
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: Phosphorylated base

<400> SEQUENCE: 53
gaggaaauga acaaguagau aaau                                           24

<210> SEQ ID NO 54
<211> LENGTH: 26
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 54
auuuaucuac uuguucauuu ccucca                                          26

<210> SEQ ID NO 55
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
ggagaccgtg acatttatct acttgttcat ttcctccaaa tataattcac ttctccaatt     60
gtcctcttct aatactgtat catctgctcc t                                    91

<210> SEQ ID NO 56
<211> LENGTH: 91
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
aggagcagat gatacagtat tagaagagga caattggaga agtgaattat atttggagga     60
aatgaacaag tagataaatg tcacggtctc c                                    91

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57
cggtggtgca gatgaacttc agggtca                                         27

<210> SEQ ID NO 58
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 58
acccugaagu ucaucugcac caccg                                           25

<210> SEQ ID NO 59
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
cgguggugca gaugaacuuc aggguca                                         27

<210> SEQ ID NO 60
```

```
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60
ggagaccgtg accggtggtg cagatgaact tcagggtca                              39

<210> SEQ ID NO 61
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
tgaccctgaa gttcatctgc accaccggtc acggtctcc                              39
```

AUTO-RECOGNIZING THERAPEUTIC RNA/DNA CHIMERIC NANOPARTICLES (NP)

CROSS-REFERENCE TO RELATED APPLICATION

This application is a 35 U.S.C. §371 U.S. national entry of International Application PCT/US2012/065945 (WO 2013/075140) having an International filing date of Nov. 19, 2012 which claims the benefit of U.S. Provisional Application No. 61/561,257, filed Nov. 17, 2011, and 61/698,113, filed Sep. 7, 2012, the contents of which are incorporated herein by reference in their entirety.

STATEMENT OF RIGHTS TO INVENTIONS MADE UNDER FEDERALLY SPONSORED RESEARCH

This work was supported by the National Institutes of Health. The government has certain rights in the invention.

SEQUENCE LISTING

The instant application contains a Sequence Listing which has been filed electronically in ASCII format and is hereby incorporated by reference in its entirety. Said ASCII copy, created on Jan. 6, 2017, is named 1420378 398US9 SL.txt and is 16,469 bytes in size.

BACKGROUND OF THE INVENTION

In the past several years, there has been a tremendous increase of interest in using RNA interference (RNAi) for biomedical applications. RNAi is a posttranscriptional sequence specific process of gene silencing employing double-stranded RNAs (dsRNAs) and a set of specific proteins and enzymes. To briefly explain the mechanism, the RNaseIII-like enzyme, Dicer, processes a dsRNAs into shorter duplexes (21-23 bp). These duplexes, referred to as short interfering RNAs (siRNAs), are then loaded into a RNA-induced silencing complex (RISC) and one of the siRNA strands, called passenger or sense, is discarded. The other strand, called guide or antisense, is used by RISC to recognize the target mRNA for cleavage and translation prevention. RNAi has become a powerful technique for selective suppression of particular genes of interest in different species showing potential for use as cancer and HIV therapeutics. Synthetic siRNAs against particular genes of interest can be exogenously introduced into cells to activate RNAi. Moreover, introduction of synthetic asymmetric Dicer substrates slightly longer than siRNAs (25 bp) tremendously increases the potency of silencing. This can be explained by the involvement of Dicer in the process of loading the RISC complex with siRNAs. Despite the potential for siRNA, there is a need for novel approaches that overcome several challenges associated with the clinical delivery of RNAi.

As described herein, the present invention splits the functionality of Dicer substrates siRNA duplexes into two R/DNA hybrids, which upon simultaneous presence inside the same diseased cell will recognize each other through toehold interaction and re-associate releasing active siRNAs. This novel approach will overcome several challenges associated with the clinical delivery of RNAi, such as intravascular degradation (will be reduced for R/DNA hybrids), tissue specificity (DNA chemistry is more parsimonious than RNA and amenable to chemical modifications with different features for targeting or delivery), pharmacodynamics (fluorescent tags can be activated upon R/DNA hybrid re-association assisting in Förster resonance energy transfer (FRET) imaging of delivery and response). Moreover, all these additional functionalities can be introduced through chemical modifications of the DNA strands in the R/DNA hybrids thus, not interfering with the processivity of the released siRNAs. Additionally, the number of these functionalities can be at least as large as twice the number of DNA strands entering into the composition of the duplex hybrids or more complex hybrid nanostructures.

SUMMARY OF THE INVENTION

The invention provides R/DNA chimeric polyfunctional nanoparticles which are able to reassemble to produce functionalized dsRNA.

In one aspect, the invention generally features an R/DNA chimeric polyfunctional nanoparticles (R/DNA NP) having at least two chimeric nanoparticles wherein the first chimeric nanoparticle having a first DNA oligonucleotide and a complementary first RNA oligonucleotide, and the second chimeric nanoparticle having a second DNA oligonucleotide and a complementary second RNA oligonucleotide, where the first DNA oligonucleotide has a 5' toehold sequence and the second DNA oligonucleotide has a 3' toehold sequence. In embodiments, the first RNA is complementary to the second RNA and when duplexed form an siRNA.

In embodiments, the R/DNA NP contain another pair of chimeric nanoparticles having complementary 5' and 3' toehold sequences.

In embodiments, the first RNA oligonucleotide comprises at least two RNA oligonucleotides. In related embodiments, the second RNA oligonucleotide comprises at least two RNA oligonucleotides corresponding to the at least two RNA oligonucleotides that make up the first RNA oligonucleotide. In embodiments, the duplexed form of the complementary RNA oligonucleotides is an siRNA.

In embodiments, the first chimeric nanoparticle and the second chimeric nanoparticle each comprises at least one additional RNA that is complementary to each other and to the DNA oligonucleotides. In related embodiments, the duplexed form of the at least one additional RNAs is an siRNA.

In embodiments the 5' toehold comprises from 5 to 50 nucleotides. In another embodiment the 5' toehold comprises from 12 to 30 nucleotides.

In embodiments the 3' toehold comprises from 5 to 50 nucleotides. In another embodiment the 3' toehold comprises from 12 to 30 nucleotides.

In embodiments at least one oligonucleotide comprises at least one modified nucleotide. In some embodiments the modified nucleotide is selected from the group consisting of locked nucleic acids (LNAs), 2' Fluoro amidites, and 2'OMe RNA amidites.

In embodiments, the siRNA inhibits a target RNA. In general, the target RNA is one which produces a therapeutically beneficial result when inhibited. In embodiments, the target RNA comprises an RNA that encodes a protein involved in a disease process or a portion thereof.

In related embodiments, the target RNA comprises an RNA that encodes an apoptosis inhibitor protein or a portion thereof (e.g., Survivin, BCL-2, FLIP, STAT3, and XIAP).

In related embodiments, the target RNA is a pathogenic RNA genome, an RNA transcript derived from the genome of the pathogenic agent, or a portion thereof. In some embodiments, the target RNA is a viral RNA genome or a portion thereof (e.g., an HIV genome).

In any of the above aspects and embodiments, the first chimeric nanoparticle can comprise a first functional moiety.

In any of the above aspects and embodiments, the second chimeric nanoparticle can comprise a second functional moiety.

In related embodiments, the first and/or second functional moiety is a recognition domain. In embodiments, the recognition domain binds to a recognition target. The recognition target can be located on or in a target cell.

In embodiments, the target cell is a diseased cell (e.g., a neoplastic cell, a cell infected with a pathogen, or a cell having a genetic disorder).

In embodiments, the recognition domain specifically binds to a nucleic acid molecule, polypeptide, or fragment thereof.

In embodiments, fluorescent tags, domains facilitating cellular uptake, split functionality domains, split lipase, and split GFP. In some embodiments, the functional moieties can also be RNA-fluorophore complexes that emit a signal upon association. See Paige, J. S. et al., *Science* 333:642-646 (2011).

In embodiments, the recognition domain is an aptamer. In embodiments, the aptamer binds a cell membrane polypeptide or cell membrane structure. The cell membrane polypeptide or cell membrane structure can be a disease specific membrane protein or structure (e.g., cancer specific membrane protein or structure, a specific membrane protein or structure associated with infection by a pathogenic agent, and the like). In embodiments, the aptamer binds a molecule in the cell. For example, the aptamer can bind a nucleic acid molecule in the target cell or a portion thereof (e.g., DNA molecule, RNA molecule, or fragment thereof).

In some embodiments, the R/DNA NPs contain at least one of the sequences described herein (in the description and the figures).

In another aspect, the invention features methods for using the R/DNA NPs described herein.

In aspects, the invention features methods for inhibiting or reducing the expression of a target gene in a cell. In embodiments, the methods involve contacting the cell with a therapeutically effective amount of at least one of the R/DNA NPs described herein. In embodiments, the cell is in a subject.

In aspects, the invention features methods for killing a pathogen infected cell. In embodiments, the methods involve contacting the cell with a therapeutically effective amount of at least one of the R/DNA NPs described herein. In embodiments, the cell is in a subject.

In aspects, the invention features methods for inhibiting replication of a pathogen in a cell. In embodiments, the methods involve contacting the cell with a therapeutically effective amount of at least one of the R/DNA NPs described herein. In embodiments, the cell is in a subject.

In aspects, the invention features methods for reducing pathogenic burden in a subject. In embodiments, the methods involve administering a therapeutically effective amount of a therapeutically effective amount of at least one of the R/DNA NPs described herein. In embodiments, the subject is at risk of developing a pathogenic infection. In embodiments, the subject is diagnosed with having a pathogenic infection.

In aspects, the invention features methods for treating or preventing a pathogenic infection in a subject. In embodiments, the methods involve administering a therapeutically effective amount of a therapeutically effective amount of at least one of the R/DNA NPs described herein. In embodiments, the methods reduce the pathogenic burden, thereby treating or preventing the pathogenic infection. In embodiments, the methods induce death in infected cell, thereby treating or preventing the pathogenic infection.

In any of the above aspects and embodiments, the subject can be a mammal (e.g., human).

In any of the above aspects and embodiments, the pathogen can be a virus, bacteria, fungus, or parasite. In some embodiments, the pathogen is a virus (e.g., HIV).

In any of the above aspects and embodiments, the methods can involve further contacting the cell with a therapeutically effective amount of a second therapeutic agent or administering a therapeutically effective amount of the second therapeutic agent to the subject. The second therapeutic agent can treat the pathogenic infection or the symptoms associated with pathogenic infection. For example, the second therapeutic agent can be an anti-viral agent, an anti-bacterial agent, an anti-fungal agent, or an anti-parasitic agent. Such agents are well known in the art, and it is within the purview of a physician to select and determine the appropriate dosage of the second therapeutic agent. See, e.g., *Drug Information Handbook: A Comprehensive Resource for All Clinicians and Healthcare Professionals*, 20$^{th}$ Ed., C. F. Lacy et al. (eds.) (Lexi-Comp 2011); *Johns Hopkins ABX Guide: Diagnosis & Treatment of Infectious Diseases*, 2$^{nd}$ Ed., J. G. Bartlett et al. (eds.) (Jones & Bartlett Publishers 2010); and *Mandell, Douglas, and Bennett's Principles and Practice of Infectious Diseases: Expert Consult Premium Edition*, 7$^{th}$ Ed., G. L. Mandell (ed.) (Churchill Livingstone 2009); *The Sanford Guide to Antimicrobial Therapy 2012*, 42$^{nd}$ Ed., D. N. Gilbert et al. (eds.) (Antimicrobial Therapy 2012); *Clinical Infectious Disease* 2013, 11$^{th}$ Ed., C. G. Weber (ed.) (Pacific Primary Care Software 2012), the contents of which are hereby incorporated by reference in their entirety.

In aspects, the invention features methods for killing a neoplastic cell. In embodiments, the methods involve contacting the cell with a therapeutically effective amount of at least one of the R/DNA NPs described herein. In embodiments, the cell is in a subject.

In aspects, the invention features methods for treating a subject having a neoplasia. In embodiments, the methods involve administering a therapeutically effective amount of a therapeutically effective amount of at least one of the R/DNA NPs described herein.

In embodiments, the neoplastic cell is a cancer cell which is present in a solid tumor. In embodiments, the cancer is selected from the group consisting of breast cancer, prostate cancer, melanoma, glioblastomas, colon cancer, ovarian cancer, and non-small cell lung cancer.

In related embodiments, the methods involve contacting the cell with a therapeutically effective amount of a second therapeutic agent or administering a therapeutically effective amount of the second therapeutic agent to the subject. In some embodiments, the second therapeutic agent is an anti-cancer agent. Anti-cancer agents are well known in the art, and any such agent is suitable for use in the present invention. See, e.g., *Anticancer Drugs: Design, Delivery and Pharmacology* (*Cancer Etiology, Diagnosis and Treatments*) (eds. Spencer, P. & Holt, W.) (Nova Science Publishers, 2011); *Clinical Guide to Antineoplastic Therapy: A Chemotherapy Handbook* (ed. Gullatte) (Oncology Nursing Society, 2007); *Chemotherapy and Biotherapy Guidelines and Recommendations for Practice* (eds. Polovich, M. et al.) (Oncology Nursing Society, 2009); *Physicians' Cancer Chemotherapy Drug Manual 2012* (eds. Chu, E. & DeVita, Jr., V. T.) (Jones & Bartlett Learning, 2011); *DeVita, Hellman, and Rosenberg's Cancer: Principles and Practice of Oncology* (eds. DeVita, Jr., V. T. et al.) (Lippincott Williams & Wilkins, 2011); and *Clinical Radiation Oncology* (eds. Gunderson, L. L. & Tepper, J. E.) (Saunders) (2011), the contents of which are hereby incorporated by references in their entirety. For example, nonlimiting examples of anti-cancer agents include Abiraterone Acetate, Afatinib, Aldesleukin, Alemtuzumab, Alitretinoin, Altretamine, Amifostine, Aminoglutethimide Anagrelide, Anastrozole, Arsenic Trioxide, Asparaginase, Azacitidine, Azathioprine, Bendamustine, Bevacizumab, Bexarotine, Bicalutamide, Bleomycin, Bortezomib, Busulfan, Capecitabine, Carboplatin, Carmustine, Cetuximab, Chlorambucil, Cisplatin, Cladribine, Crizotinib, Cyclophosphamide, Cytarabine, Dacarbazine, Dactinomycin, Dasatinib, Daunorubicin, Denileukin diftitox, Decitabine, Docetaxel, Dexamethasone, Doxifluridine, Doxorubicin, Epirubicin, Epoetin Alpha, Epothilone, Erlotinib, Estramustine, Etinostat, Etoposide, Everolimus, Exemestane, Filgrastim, Floxuridine, Fludarabine, Fluorouracil, Fluoxymesterone, Flutamide, folate linked alkaloids, Gefitinib, Gemcitabine, Gemtuzumab ozogamicin, GM-CT-01, Goserelin, Hexamethylmelamine, Hydroxyureas, Ibritumomab, Idarubicin, Ifosfamide, Imatinib, Interferon alpha, Interferon beta, Irinotecan, Ixabepilone, Lapatinib, Leucovorin, Leuprolide, Lenalidomide, Letrozole, Lomustine, Mechlorethamine, Megestrol, Melphalan, Mercaptopurine, Methotrexate, Mitomycin, Mitoxantrone, Nelarabine, Nilotinib, Nilutamide, Octreotide, Ofatumumab, Oprelvekin, Oxaliplatin, Paclitaxel, Panitumumab, Pemetrexed, Pentostatin, polysaccharide galectin inhibitors, Procarbazine, Raloxifene, Retinoic acids, Rituximab, Romiplostim, Sargramostim, Sorafenib, Streptozocin, Sunitinib, Tamoxifen, Temsirolimus, Temozolamide, Teniposide, Thalidomide, Thioguanine, Thiotepa, Tioguanine, Topotecan, Toremifene, Tositumomab, Trametinib, Trastuzumab, Tretinoin, Valrubicin, VEGF inhibitors and traps, Vinblastine, Vincristine, Vindesine, Vinorelbine, Vintafolide (EC145), Vorinostat, or a salt thereof.

In any of the above aspects and embodiments, the pathogen can be any known virus, bacteria, fungus, or parasite known in the art. See, e.g., *Clinical Infectious Disease* 2013, 11$^{th}$ Ed., C. G. Weber (ed.) (Pacific Primary Care Software 2012).

Exemplary bacterial pathogens include, but are not limited to, *Aerobacter, Aeromonas, Acinetobacter, Actinomyces israelli, Agrobacterium, Bacillus, Bacillus antracis, Bacteroides, Bartonella, Bordetella, Bortella, Borrelia, Brucella, Burkholderia, Calymmatobacterium, Campylobacter, Citrobacter, Clostridium, Clostridium perfringers, Clostridium tetani, Cornyebacterium, corynebacterium diphtheriae, corynebacterium* sp., *Enterobacter, Enterobacter aerogenes, Enterococcus, Erysipelothrix rhusiopathiae, Escherichia, Francisella, Fusobacterium nucleatum, Gardnerella, Haemophilus, Hafnia, Helicobacter, Klebsiella, Klebsiella pneumoniae, Lactobacillus, Legionella, Leptospira, Listeria, Morganella, Moraxella, Mycobacterium, Neisseria, Pasteurella, Pasturella multocida, Proteus, Providencia, Pseudomonas, Rickettsia, Salmonella, Serratia, Shigella, Staphylococcus, Stentorophomonas, Streptococcus, Streptobacillus moniliformis, Treponema, Treponema pallidium, Treponema pertenue, Xanthomonas, Vibrio,* and *Yersinia*.

Exemplary viruses include, but are not limited to, Retroviridae (e.g., human immunodeficiency viruses, such as HIV-1 (also referred to as HDTV-III, LAVE or HTLV-III/LAV, or HIV-III; and other isolates, such as HIV-LP; Picornaviridae (e.g., polio viruses, hepatitis A virus; enteroviruses, human Coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronoviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g. influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus; Poxyiridae (variola viruses, vaccinia viruses, pox viruses); and Iridoviridae (e.g. African swine fever virus); and unclassified viruses (e.g. the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of pathogenic fungi include, without limitation, *Alternaria, Aspergillus, Basidiobolus, Bipolaris, Blastoschizomyces, Candida, Candida albicans, Candida krusei, Candida glabrata* (formerly called *Torulopsis glabrata*), *Candida parapsilosis, Candida tropicalis, Candida pseudotropicalis, Candida guilliermondii, Candida dubliniensis,* and *Candida lusitaniae, Coccidioides, Cladophialophora, Cryptococcus, Cunninghamella, Curvularia, Exophiala, Fonsecaea, Histoplasma, Madurella, Malassezia, Plastomyces, Rhodotorula, Scedosporium, Scopulariopsis, Sporobolomyces, Tinea,* and *Trichosporon*.

Parasites can be classified based on whether they are intracellular or extracellular. An "intracellular parasite" as used herein is a parasite whose entire life cycle is intracellular. Examples of human intracellular parasites include *Leishmania, Plasmodium, Trypanosoma cruzi, Toxoplasma gondii, Babesia,* and *Trichinella spiralis*. An "extracellular parasite" as used herein is a parasite whose entire life cycle is extracellular. Extracellular parasites capable of infecting humans include *Entamoeba histolytica, Giardia lamblia, Enterocytozoon bieneusi, Naegleria* and *Acanthamoeba* as well as most helminths. Yet another class of parasites is defined as being mainly extracellular but with an obligate intracellular existence at a critical stage in their life cycles. Such parasites are referred to herein as "obligate intracellular parasites". These parasites may exist most of their lives or only a small portion of their lives in an extracellular environment, but they all have at lest one obligate intracellular stage in their life cycles. This latter category of parasites includes *Trypanosoma rhodesiense* and *Trypanosoma gambiense, Isospora, Cryptosporidium, Eimeria, Neospora, Sarcocystis,* and *Schistosoma*. In one aspect, the invention relates to the prevention and treatment of infection resulting from intracellular parasites and obligate intracellular parasites which have at least in one stage of their life cycle that is intracellular. In some embodiments, the invention is directed to the prevention of infection from obligate intracellular parasites which are predominantly intracellular. An exemplary and non-limiting list of parasites for some aspects of the invention include *Plasmodium* spp. such as *Plasmodium falciparum, Plasmodium malariae, Plasmodium ovale,* and *Plasmodium vivax* and *Toxoplasma gondii*. Blood-borne and/or tissues parasites include *Plasmodium* spp., *Babesia microti, Babesia divergens, Leishmania tropica, Leishmania* spp., *Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*. Blood-borne and/or tissues parasites include *Plasmodium, Babesia microti, Babesia divergens, Leishmania tropica, Leishmania, Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*.

The invention also features compositions (including pharmaceutical compositions) containing at least one of the R/DNA NPs described herein. In embodiments, the composition also contains a pharmaceutically acceptable excipient, carrier, or diluent.

In embodiments, the compositions are used for one of at least one of the methods described herein.

In embodiments, the compositions further contain at least one additional therapeutic agent. In some embodiments, the second therapeutic agent treats or reduces the symptoms associated with infection by a pathogenic agent. In some embodiments, the second therapeutic agent is an anti-cancer agent.

The invention further features kits containing the R/DNA NPs and/or compositions described herein. In embodiments, the kits are used for at least one of the methods described herein. In related embodiments, the kits further contain instructions for using the kits in at least one of the methods described herein.

In some embodiments, the kits contain at least one additional therapeutic agent. In embodiments, the second therapeutic agent treats or reduces the symptoms associated with infection by a pathogenic agent. In embodiments, the second therapeutic agent is an anti-cancer agent.

Computationally designed therapeutic R/DNA chimeric polyfunctional nanoparticles (R/DNA NP) are described which represent a means for triggering the RNAi pathway as well as other functionalities inside targeted or diseased cells. Therapeutic R/DNA NP are at least a pair of RNA/DNA duplexes where the two DNA and the two RNAs are complements of each other. The DNA molecules have toehold sequences that are complementary. The toehold sequences in each R/DNA NP causes the molecules to undergo re-association which results in a DNA/DNA duplex and an RNA/RNA duplex. The RNA/RNA duplex is designed to be an siRNA which inhibits a target RNA. The target RNA can be any transcript the silencing of which would have a therapeutic effect. Accordingly, the R/DNA NPs can be used in any situation where siRNAs are used or contemplated to be used. The R/DNA NP molecules can also have moieties that bind to various molecules. For example, the moieties can bind to cell surface proteins that are only present on cells of interest (e.g., diseased cells, neoplastic cells, or cells infected with a virus, e.g., HIV infected cells). Thus, the particles are targeted to and enter the specific cells in which a target gene is intended to be inhibited (e.g. disease cells including neoplastic cells, infected cells, etc.). Following re-association the siRNA becomes activated and results in the inhibition of the target gene resulting in a therapeutically desirable effect (e.g., death of a neoplastic or infected cell).

Additional objects and advantages of the invention will be set forth in part in the description which follows, and in part will be obvious from the description, or may be learned by practice of the invention. The objects and advantages of the invention will be realized and attained by means of the elements and combinations disclosed herein, including those pointed out in the appended claims. It is to be understood that both the foregoing general description and the following detailed description are exemplary and explanatory only and are not restrictive of the invention as claimed. The accompanying drawings, which are incorporated in and constitute a part of this specification, illustrate several embodiments of the invention and, together with the description, serve to explain the principles of the invention.

DEFINITIONS

By "therapeutic R/DNA chimeric polyfunctional nanoparticles" or "R/DNA NP" is meant a pair of RNA/DNA hybrid molecules in which the DNA and RNA molecules are complementary. The DNA molecule of the first R/DNA NP has a 3' toehold sequence and the DNA molecule of the second R/DNA NP has a 5' toehold sequence. The 3' and 5' toehold sequences are complementary to each other. When the two R/DNA NPs are mixed the toehold sequences form a duplex which results in the re-association of the two R/DNA NPs. The end result of the re-association is a DNA/DNA duplex and an RNA/RNA duplex wherein the RNA/RNA duplex is designed to operate as an siRNA that inhibits a target RNA.

By "toehold" is meant single stranded stretches of nucleic acids. The R/DNA NPs contain complementary toeholds where the binding of the complementary toeholds results in re-association between the two R/DNA NPs. Toeholds described herein can be from 5 to 50 nucleotides in length and preferably from 12 to 30 nucleotides in length.

By "target RNA" or "target human RNA" is meant an RNA that encodes a polypeptide that has a functionality whose inhibition would be therapeutically beneficial.

By "agent" is meant any small molecule chemical compound, antibody, nucleic acid molecule, or polypeptide, or fragments thereof.

By "ameliorate" is meant decrease, suppress, attenuate, diminish, arrest, or stabilize the development or progression of a disease.

By "alteration" is meant a change (increase or decrease) in the expression levels or activity of a gene or polypeptide as detected by standard art known methods such as those described herein. As used herein, an alteration includes a 10% change in expression levels, preferably a 25% change, more preferably a 40% change, and most preferably a 50% or greater change in expression levels. "

By "analog" is meant a molecule that is not identical, but has analogous functional or structural features. For example, a polypeptide analog retains the biological activity of a corresponding naturally-occurring polypeptide, while having certain biochemical modifications that enhance the analog's function relative to a naturally occurring polypeptide. Such biochemical modifications could increase the analog's protease resistance, membrane permeability, or half-life, without altering, for example, ligand binding. An analog may include an unnatural amino acid.

In this disclosure, "comprises," "comprising," "containing" and "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition or disorder that damages or interferes with the normal function of a cell, tissue, or organ.

By "effective amount" is meant the amount of a required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The invention provides a number of targets that are useful for the development of highly specific drugs to treat or a disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "inhibits neoplasia" is meant decreases the propensity of a cell to develop into neoplasia or slows, decreases, or stabilizes the growth or proliferation of a neoplasia.

By "inhibitory nucleic acid" is meant a double-stranded RNA, siRNA, shRNA, or antisense RNA, or a portion thereof, or a mimetic thereof, that when administered to a mammalian cell results in a decrease (e.g., by 10%, 25%, 50%, 75%, or even 90-100%) in the expression of a target gene. Typically, a nucleic acid inhibitor comprises at least a portion of a target nucleic acid molecule, or an ortholog thereof, or comprises at least a portion of the complementary strand of a target nucleic acid molecule. For example, an inhibitory nucleic acid molecule comprises at least a portion of any or all of the nucleic acids delineated herein.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. Preferably, the preparation is at least 75%, more preferably at least 90%, and most preferably at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "marker" is meant any protein or polynucleotide having an alteration in expression level or activity that is associated with a disease or disorder.

By "neoplasia" is meant any disease that is caused by or results in inappropriately high levels of cell division, inappropriately low levels of apoptosis, or both. For example, cancer is a neoplasia. Examples of cancers include, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (Hodgkin's disease, non-Hodgkin's disease), Waldenstrom's macroglobulinemia, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, nile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma). Lymphoproliferative disorders are also considered to be proliferative diseases.

By "neoplastic cell" is meant a cell that is a component of a neoplasia.

As used herein, "obtaining" as in "obtaining an agent" includes synthesizing, purchasing, or otherwise acquiring the agent.

"Primer set" means a set of oligonucleotides that may be used, for example, for PCR. A primer set would consist of at least 2, 4, 6, 8, 10, 12, 14, 16, 18, 20, 30, 40, 50, 60, 80, 100, 200, 250, 300, 400, 500, 600, or more primers.

By "recognition domain" is meant a chemical structure that binds to a recognition target.

By "recognition target" is meant a structure that is present on the surface of a target cell that is bound by a recognition domain.

By "reduces" is meant a negative alteration of at least 10%, 25%, 50%, 75%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "siRNA" is meant a double stranded RNA. Optimally, an siRNA is 18, 19, 20, 21, 22, 23 or 24 nucleotides in length and has a 2 base overhang at its 3' end. These dsRNAs can be introduced to an individual cell or to a whole animal; for example, they may be introduced systemically via the bloodstream. Such siRNAs are used to downregulate mRNA levels or promoter activity.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide, non-coding RNA, or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 .mu.g/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196: 180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, more preferably 80% or 85%, and more preferably 90%, 95% or even 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

By "subject" is meant a mammal, including, but not limited to, a human or non-human mammal, such as a bovine, equine, canine, ovine, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

(FIG. 40A) FRET experiments: cells were co-transfected with cognate hybrids labeled with Alexa488 and Alexa546 and images were taken on the next day. (FIG. 40B) Dequenching experiments: cells were co-transfected with cognate duplexes, having one duplex labeled with Alexa488 and IowaBlack FQ. Images were taken on the next day. (FIG. 40C-D) Localization of auto-recognizing R/DNA hybrids with commonly used markers for endosomal compartments (FIG. 40C) EEA1 and (FIG. 40D) Rab7.

Figure 1:
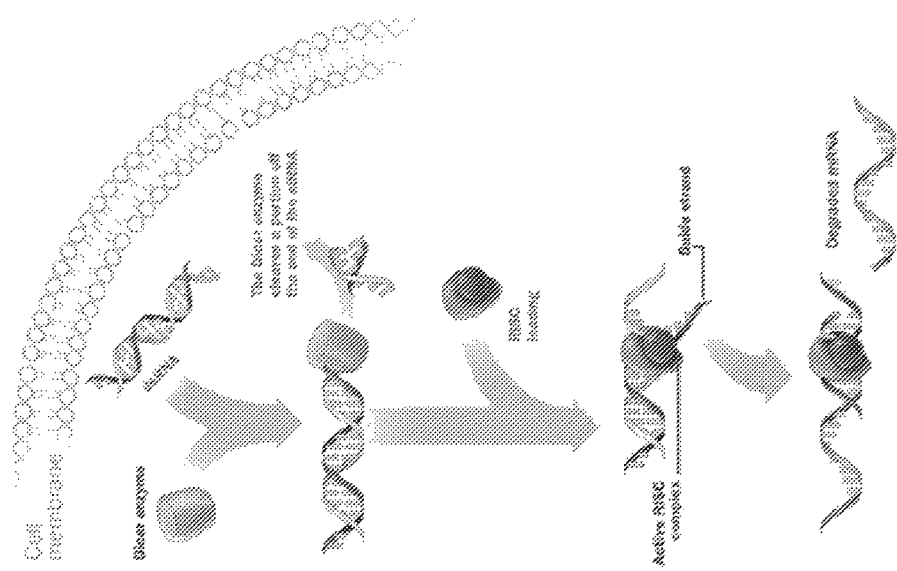
FIG. 1 is a schematic showing the RNAi pathway.

Image numbers in a-d correspond to: differential interference contrast (DIC) images (1), Alexa488 emission (2), Alexa546 emission (3), bleed-through corrected FRET image (4), 3D chart representation of zoomed fragment indicated by a white box of bleed-through corrected FRET image with the yellow star indicating the correspondence (5), EAA1 antibody staining (6), and Rab7 antibody staining (7). Images (1+2+3), (1+4), (1+2), (1+3+6), (1+3+7) are superpositions of two or three different images.

Figure 41:
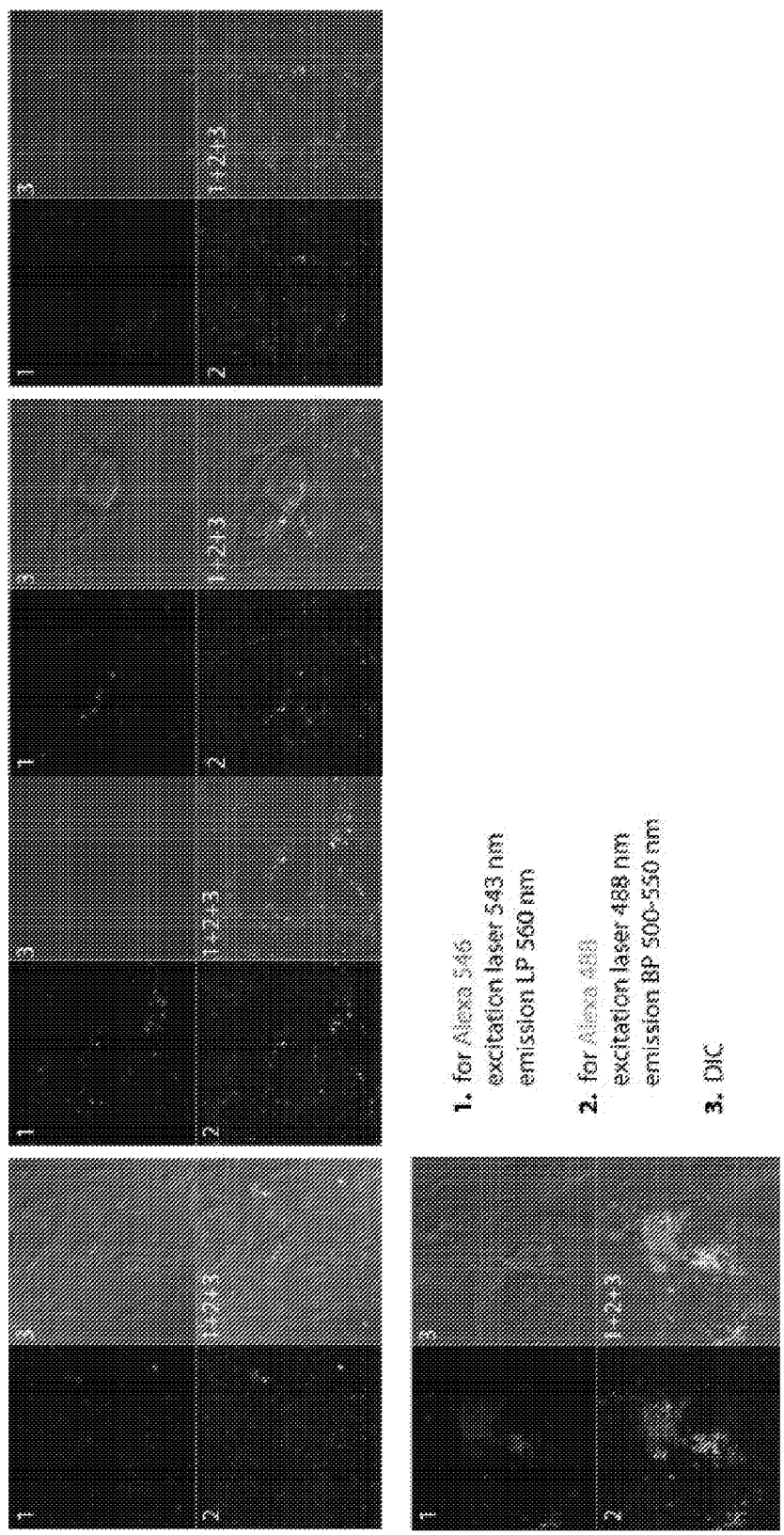

FIG. 41 shows the re-association of auto-recognizing R/DNA hybrids in human breast cancer cells (MDA-MB-231) visualized by confocal fluorescence microscopy (N=5). Cells were co-transfected with cognate hybrids labeled with Alexa488 and Alexa546 and images were taken on the next day. Image numbers correspond to: Alexa546 emission (1) Alexa488 emission (2), DIC (3).

Figure 42:
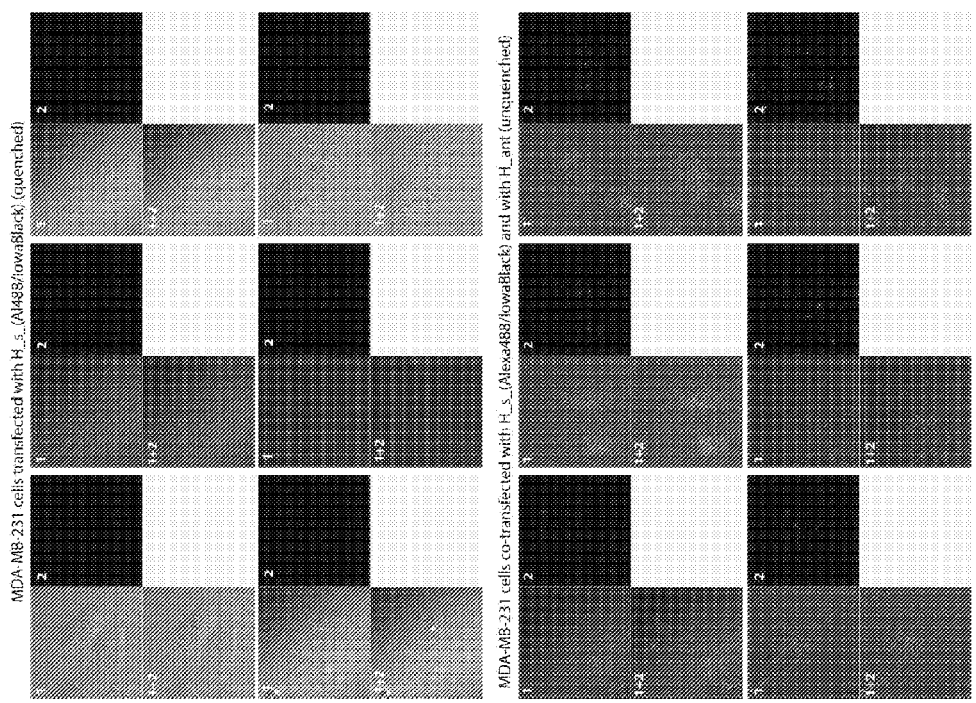

FIG. 42 is a set of photographs showing the dequenching re-association experiments (N=6) of auto-recognizing R/DNA hybrids in human breast cancer cells (MDA-MB-231) visualized by confocal fluorescence microscopy: cells were co-transfected with cognate hybrids, having one hybrid labeled with Alexa488 and IowaBlack FQ. As the control (upper panel), N=6, cells were transfected with only quenched duplex. Images were taken on the next day. Image numbers correspond to: DIC (1), Alexa488 emission (2).

FIGS. 43A-43C GFP knockdown assays for human breast cancer cells (MDA-MB-231/GFP) which stably express enhanced GFP (eGFP). Three days after the transfection of cells with auto-recognizing R/DNA hybrids programmed to release siRNAs against eGFP (H_s and H_ant), (FIG. 43A) eGFP expression was observed by fluorescence microscopy and (FIG. 43B) eGFP expression was statistically analyzed with flow cytometry experiments. As the control, siRNA duplexes against eGFP were used. Please note that the individual R/DNA hybrids cause no decrease in eGFP production (supporting FIG. S8). (FIG. 43C) Dependency of toehold lengths in auto-recognizing R/DNA hybrids co-transfected on two different days show their ability to knockdown eGFP expression. R/DNA hybrids containing antisense (H_ant) were transfected one day prior to hybrids with sense (H_s). Three days after, eGFP expression was analyzed.

Figure 44:
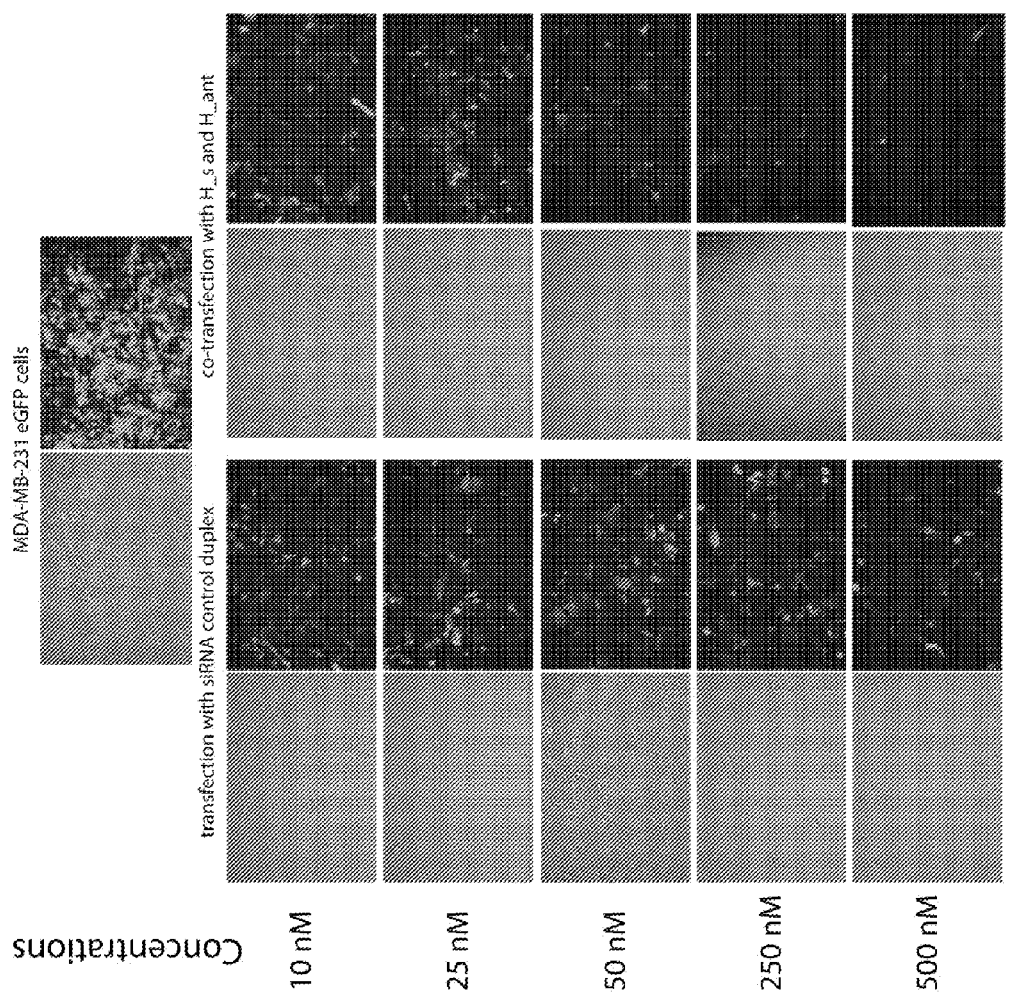

FIG. 44 is a set of photographs showing GFP knockdown assays for human breast cancer cells (MDA-MB-231/GFP) which stably express enhanced GFP (eGFP). Three days after the transfection of cells with different equimolar concentrations of auto-recognizing R/DNA hybrids programmed to release siRNA against eGFP (H_s and H_ant), eGFP expression was observed by fluorescence microscopy. As the control, siRNA duplex against eGFP was used.

FIGS. 45A & 45B are photographs and a graph showing the result of GFP knockdown assays for human breast cancer cells (MDA-MB-231/GFP) which stably express enhanced GFP (eGFP). (a) Three days after the transfection of cells with single R/DNA hybrids, eGFP expression was observed by fluorescence microscopy and statistically analyzed by flow cytometry experiments. Please note that individual R/DNA hybrids cause no decrease in eGFP production. (b) As negative controls, unrelated to eGFP silencing, auto-recognizing R/DNA hybrids designed against HIV-1 were used. Three days after the transfection of cells with R/DNA hybrids designed to release siRNAs against HIV, no eGFP expression was observed by fluorescence microscopy and flow cytometry experiments. Auto-recognizing R/DNA hybrids and siRNA against eGFP were used as the positive control.

Figure 46:
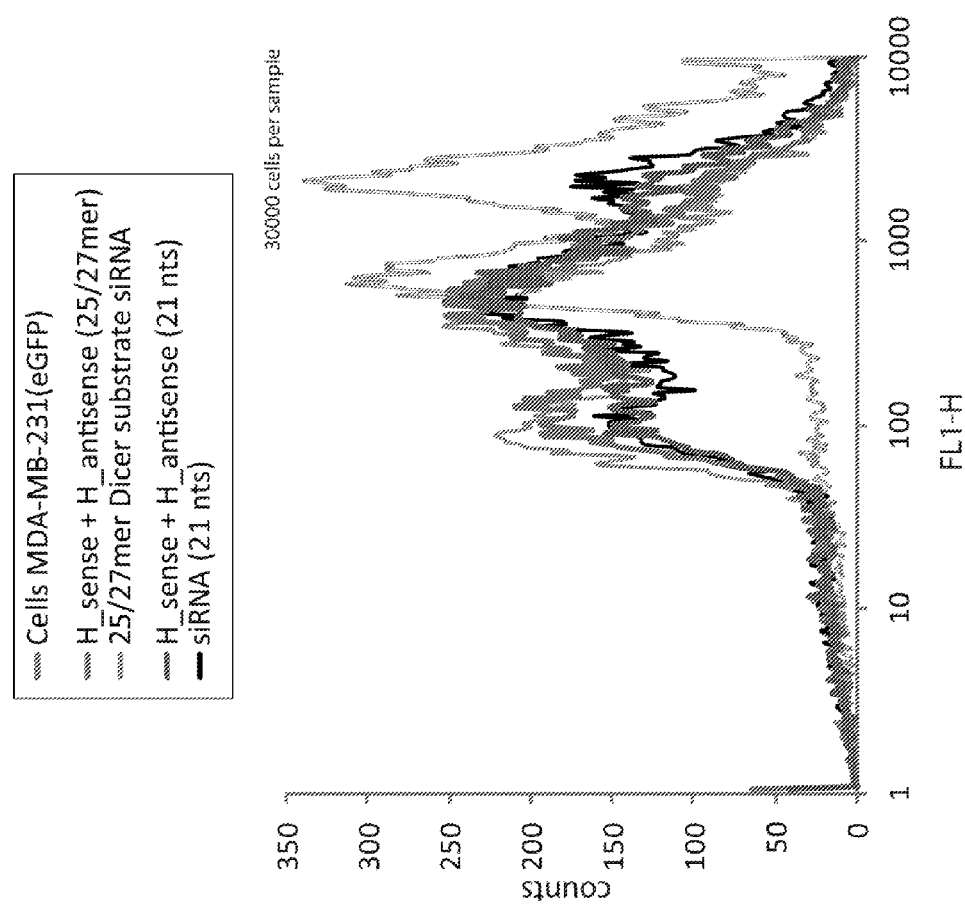

FIG. 46 shows the use of classical size siRNAs (21 nts) with R/DNA hybrids demonstrates comparable silencing efficiency of GFP knockdown compared to the elongated (25/27 mer) hybrids. Statistical analysis of eGFP expression was performed with flow cytometry. R/DNA hybrids were co-transfected on the same day and three days after, eGFP expression was analyzed.

FIGS. 47A and 47B show the use of internally segmented interfering RNAs with R/DNA hybrids leads to a higher efficiency of GFP knockdown compared to the regular hybrids. (a) Schematic representation of auto-recognizing R/DNA hybrids having internally segmented interfering RNAs (H_segmented_s). (b) Statistical analysis of eGFP expression with flow cytometry. R/DNA hybrids were co-transfected on the same day and three days after, eGFP expression was analyzed.

Figure 48:
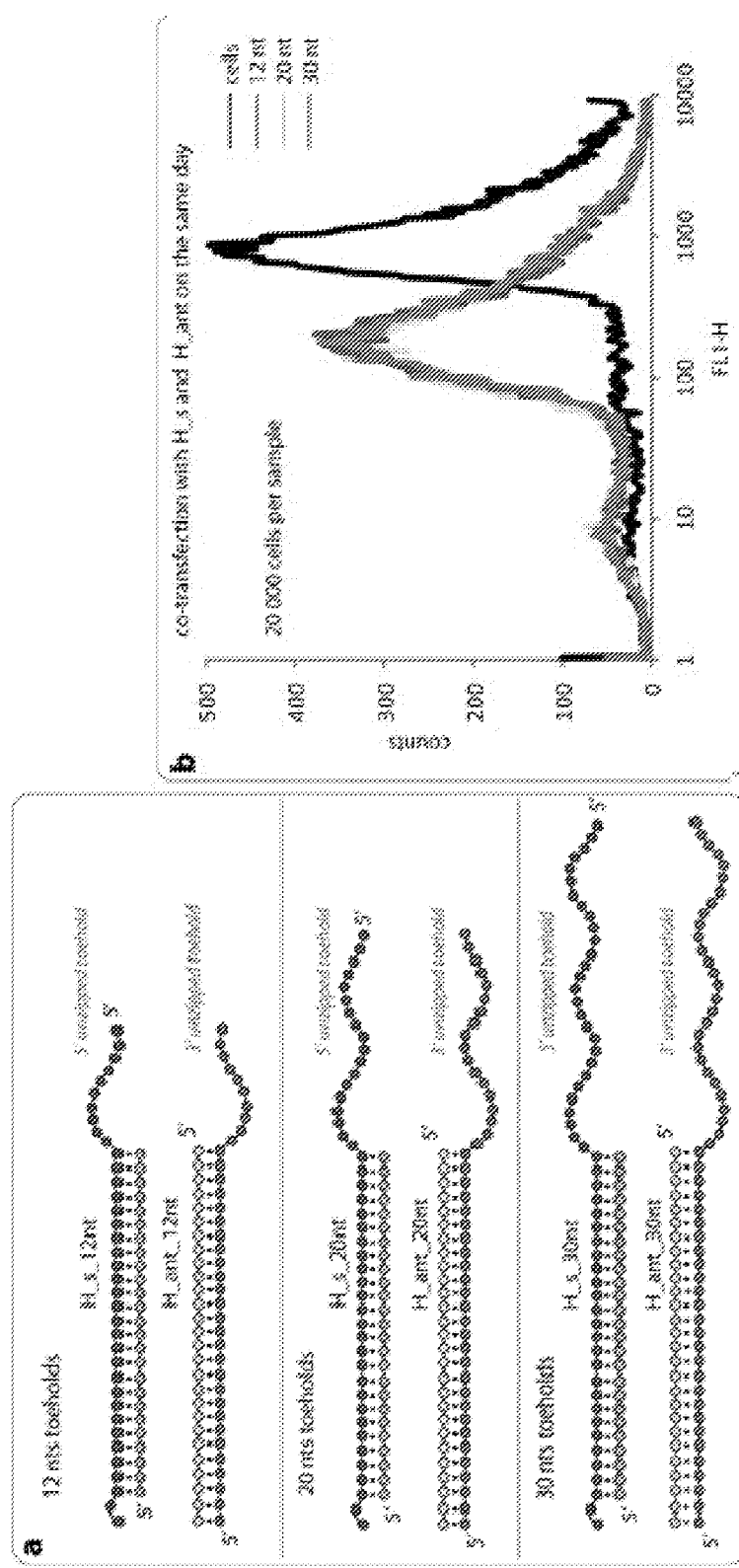

FIG. 48 shows the dependency of toehold lengths in auto-recognizing R/DNA hybrids co-transfected on the same day on their ability to knockdown eGFP expression. (a) Schematic representation of auto-recognizing R/DNA hybrids having different lengths of unzipped toeholds. (b) Statistical analysis of eGFP expression with flow cytometry. R/DNA hybrids (H_s and H_ant) were co-transfected on the same day. Three days after, eGFP expression was analyzed.

Figure 49:
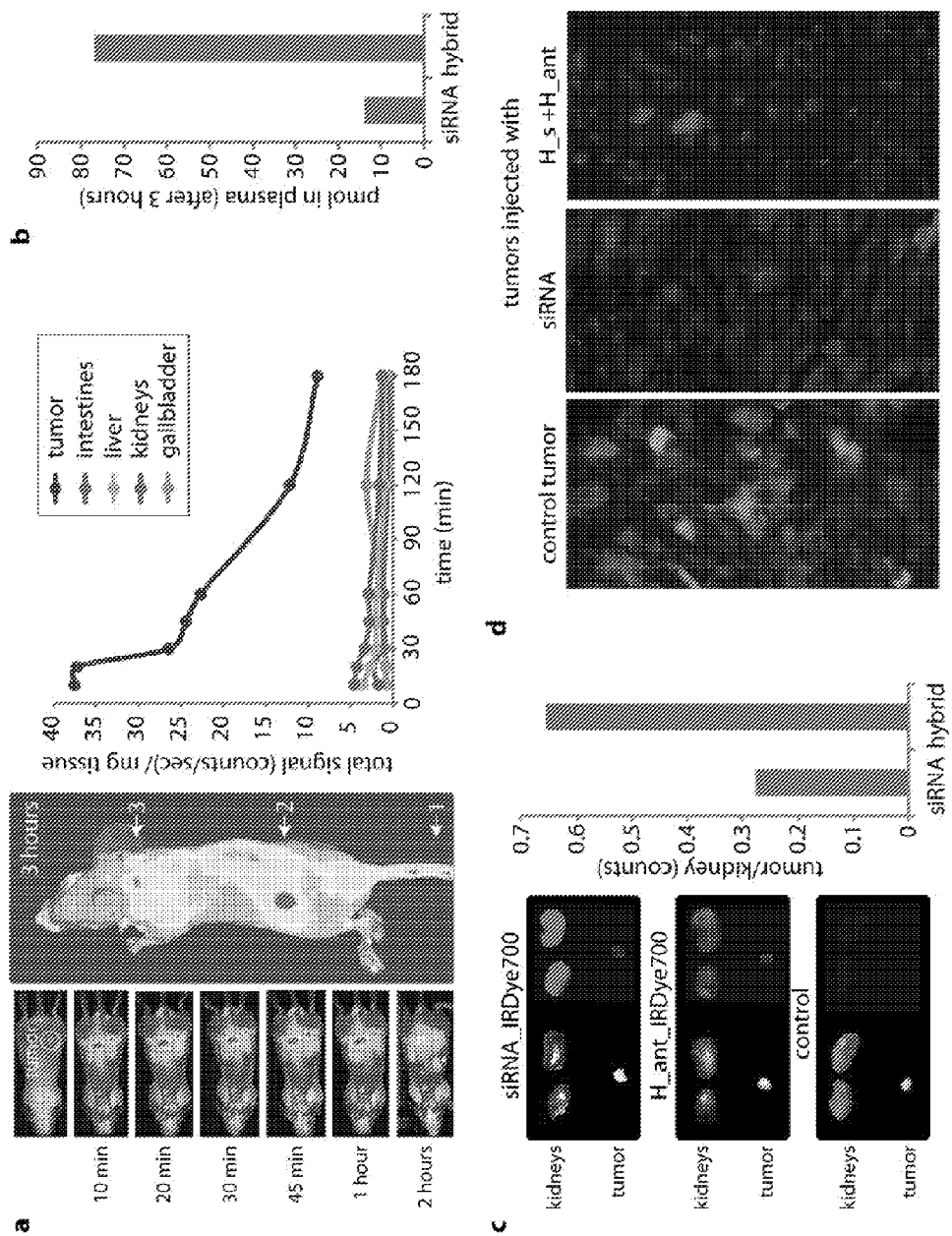

FIG. 49 shows the result of in vivo studies of auto-recognizing R/DNA hybrids in tumor xenograft mouse model. (a) Pharmacokinetic profile of fluorescently labeled R/DNA hybrids in tumor-bearing mice three hours post tail-vein injection. A relatively high level of hybrid accumulation occurs in tumor tissue. In three hours image, fluorescent maximums (in red) correspond to the places of injection (1), tumor (2), and blood withdrawal (3). (b) The amounts of the fluorescent probe (R/DNA hybrids and Dicer substrate siRNAs labeled with IRDye700) in the mouse blood-stream were measured three hours post-injection. (c) Ex vivo fluorescent imaging and analysis of mouse kidneys and tumors indicate a relatively higher tumor uptake for the R/DNA hybrids compared to Dicer substrate siRNAs. (d) Ex vivo fluorescent imaging of tumors after five days post-injections in vivo demonstrate comparable levels of eGFP silencing caused by siRNA and auto-recognizing R/DNA hybrids.

Figure 50:
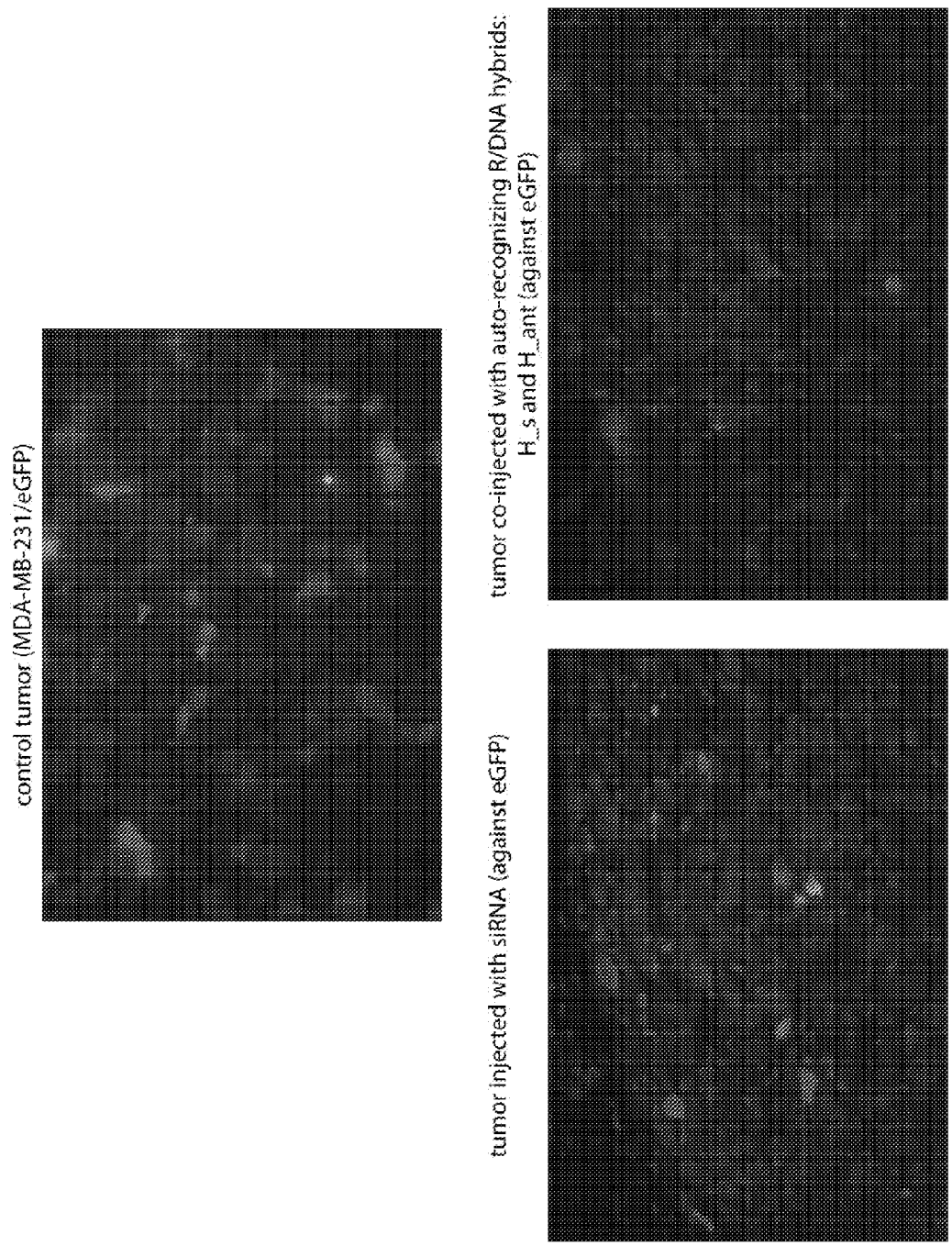

FIG. 50 is a set of photographs showing ex vivo fluorescent imaging of tumors after five days post-injections in vivo demonstrate comparable levels of eGFP silencing caused by siRNA and auto-recognizing R/DNA hybrids. Tumors were removed from mice, fixed overnight at 4° C. in 4% PFA and processed to paraffin. 5 µm sections were mounted on slides followed by deparaffinization and rehydration through graded ethanol to dH$_2$O then PBS. Proteinase K (DAKO) pretreatment was performed for 5 min at RT. Sections were blocked in NGS and incubated ON at 4° C. with anti GFP antibody (abcam #ab6556, diluted 1:1000). For fluorescent labeling, sections were incubated with Goat a/Rabbit IgG Alexa 488 (Invitrogen/Molecular Probes), counterstained with DAPI then cover-slipped with Prolong Gold a/Fade reagent (Invitrogen). Images were captured using Nikon's Eclipse 80i microscope, with a QImaging Retiga-2000R camera and Nikon's NIS-Elements AR Imaging Software. For DAB labeling, sections were incubated in Biotinylated Goat a/Rabbit IgG (Vector Labs) then ABC Elite reagent (Vector Labs), followed by DAB. A Hematoxylin counter-stain was performed and slides were coverslipped with Permount. Whole-slide digital images were captured using Aperio's ScanScope digital slide scanner.

Figure 51:
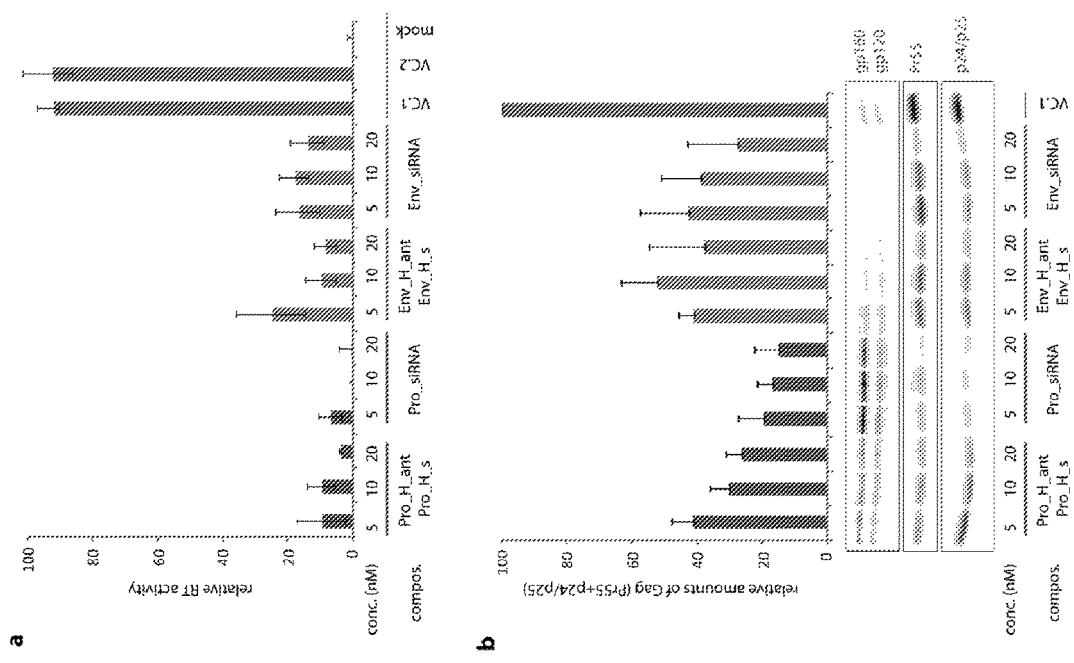

FIG. 51 shows that HIV-1 expression and production is inhibited by siRNAs and recombined R/DNA hybrids. (a) HeLa cells were transfected with pNL4-3, with and without siRNAs. Virus supernatant was harvested and RT activity was measured; data are shown normalized to virus controls (VC.1 and VC.2) without siRNAs. Error bars denote SD; N=4. (b) At 48 h posttransfection, HeLa cells were metabolically labeled with [$^{35}$S]MetCys for 4 h. Cell lysates were radioimunoprecipitated. Positions of envelope glycoprotein precursor, gp160, and surface glycoprotein gp120; Pr55Gag (Pr55), CA-SP1 (p25) and CA (p24) are indicated. Quantification of total cell-associated Gag: Pr55+p25+24. Total Gag in virus control (VC) without siRNAs set at 100. Error bars denote SD; N=3.

Figure 52:
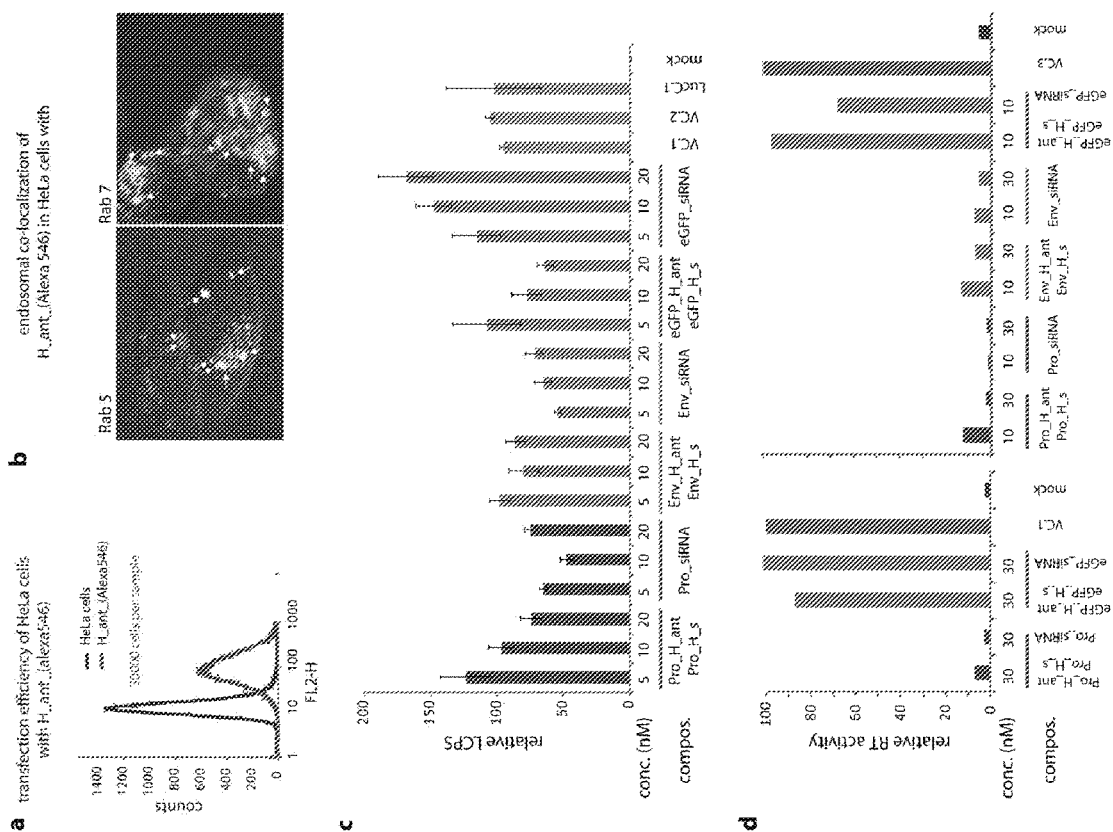

FIGS. 52A-52D show the transfection efficiencies measured by flow cytometry (FIG. 51A) and Rab5/7 (endosomal) co-localization (FIG. 51B) in HeLa cells with auto-recognizing R/DNA hybrids. Transfection efficiencies were statistically analyzed by flow cytometry (FIG. 52A) and co-localization was visualized by confocal fluorescence microscopy (FIG. 52B). Cytotoxicity of siRNAs (LCPS=luciferase counts per second) in HIV-1-expressing HeLa cells (FIG. 52C) is minimal between 5 and 20 nM. Cells are co-transfected with pNL4-3 and psiCHECK™-1 (Promega), with and without siRNAs. At 48 h post transfection, cells were lysed and *Renilla* luciferase was measured. eGFP siRNA was used as a control. VC. Virus control. LucC. Luciferase control. Error bars denote SD; N=4. (FIG. 52D) Effect on RT production. eGFP siRNA was used as a negative control. eGFP siRNAs were co-transfected with pNL4-3 plasmid and RT levels were measured in the supernatant after 48 h. VC. Virus control.

Figure 53:
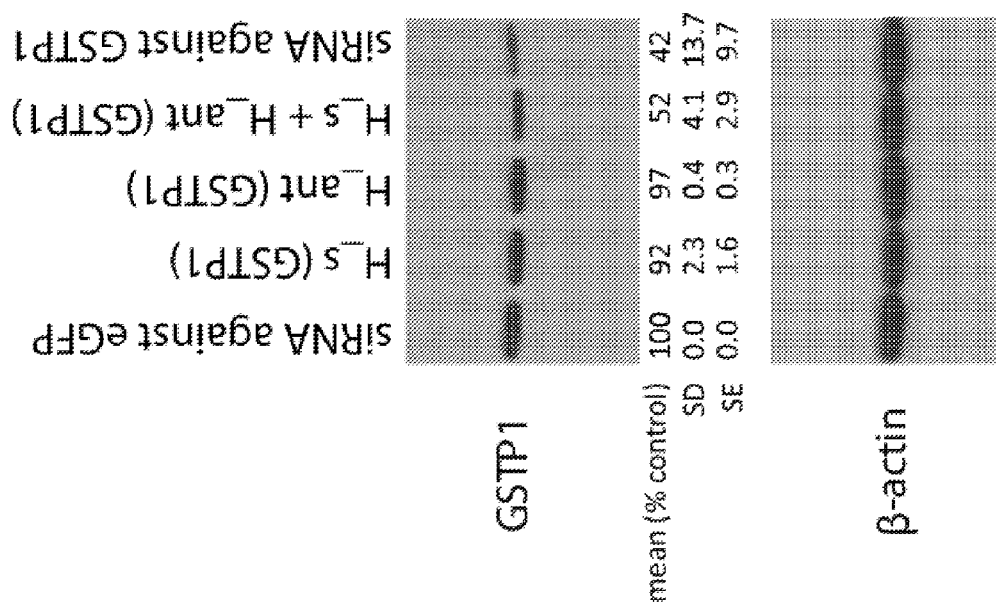

FIG. 53 shows the relative decrease in GSTP1 protein expression (with corresponding standard deviation (SD) and standard error (SE) calculated from three repetitions) in A549 lung adenocarcinoma cells after R/DNA treatment as shown by Western blot. In the case of H_s+H_ant (GSTP1), auto-recognizing R/DNA hybrids containing RNA sense strand were transfected first and after 24 hours of incubation at 37° C., a complement R/DNA hybrid containing RNA anti-sense strand of GSTP1 siRNA were transfected. Cells were collected and processed for immunoblotting using standard protocol 24 h later. Anti-GSTP1 antibody was from Cell Signaling Technology, and β-actin antibody from Abcam.

Figure 54:
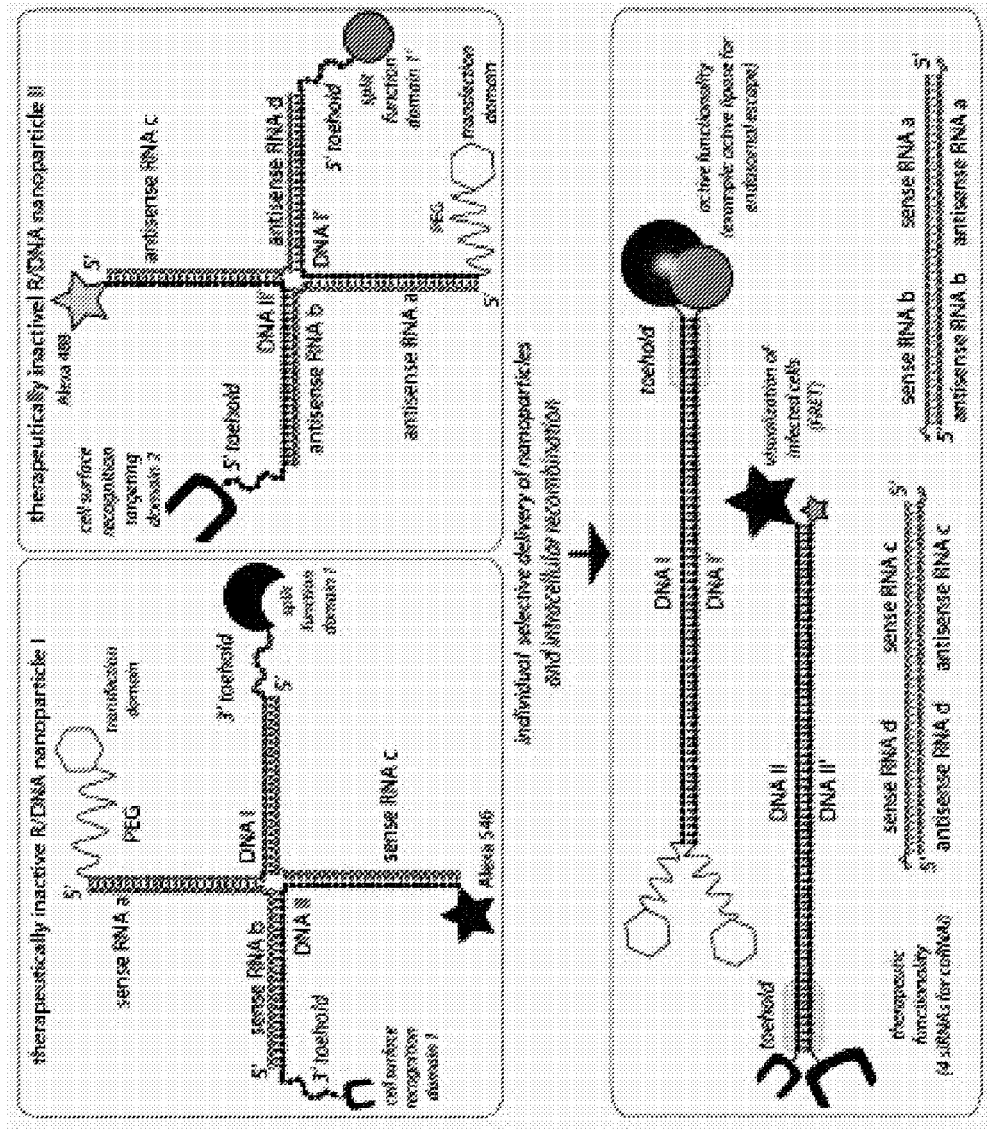

FIG. 54 is a schematic representation of two cognate auto-recognizing therapeutics R/DNA NP before (upper panel) and after (lower panel) intracellular recombination.

Figure 55:
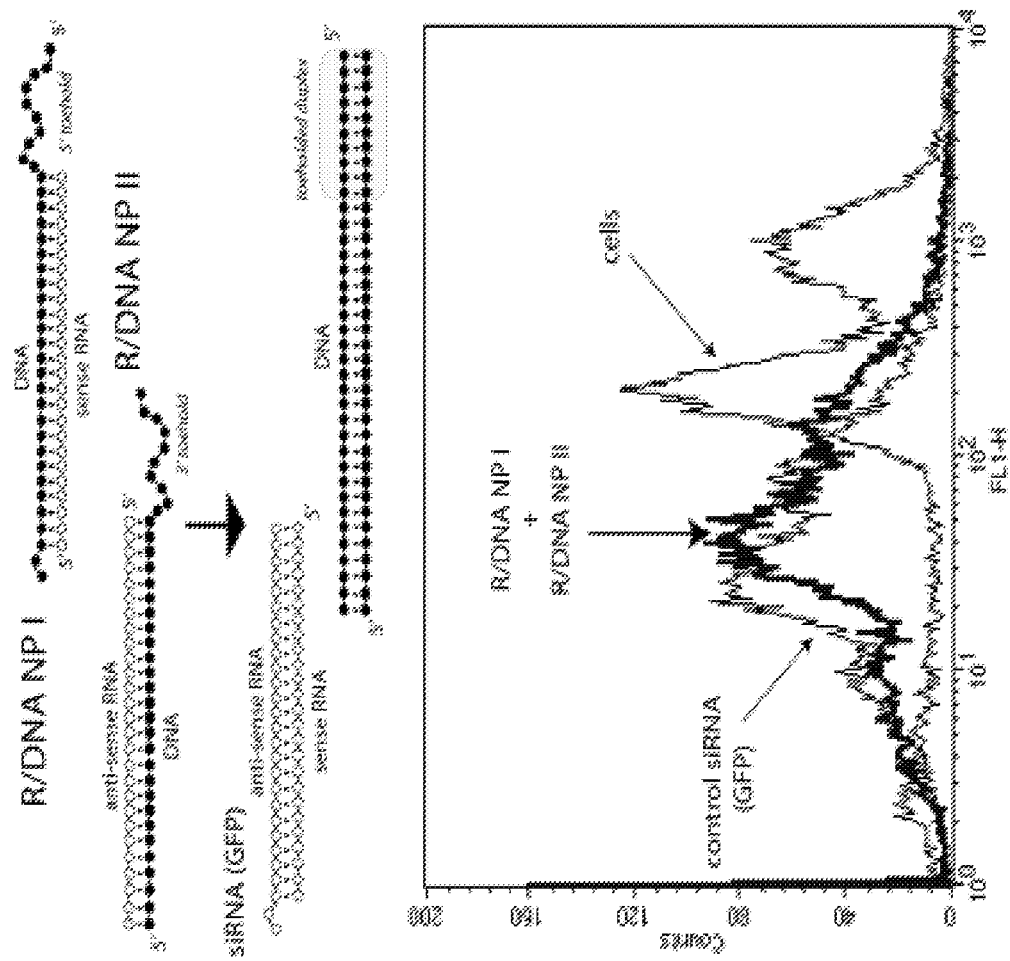

FIG. 55 is a schematic showing recombination of auto-recognizing R/DNA duplexes releasing siRNA designed against GFP gene (upper panel) and FACS data demonstrating silencing of GFP expression inside the human cells triggered by re-association of the auto-recognizing R/DNA duplexes.

Figure 56:
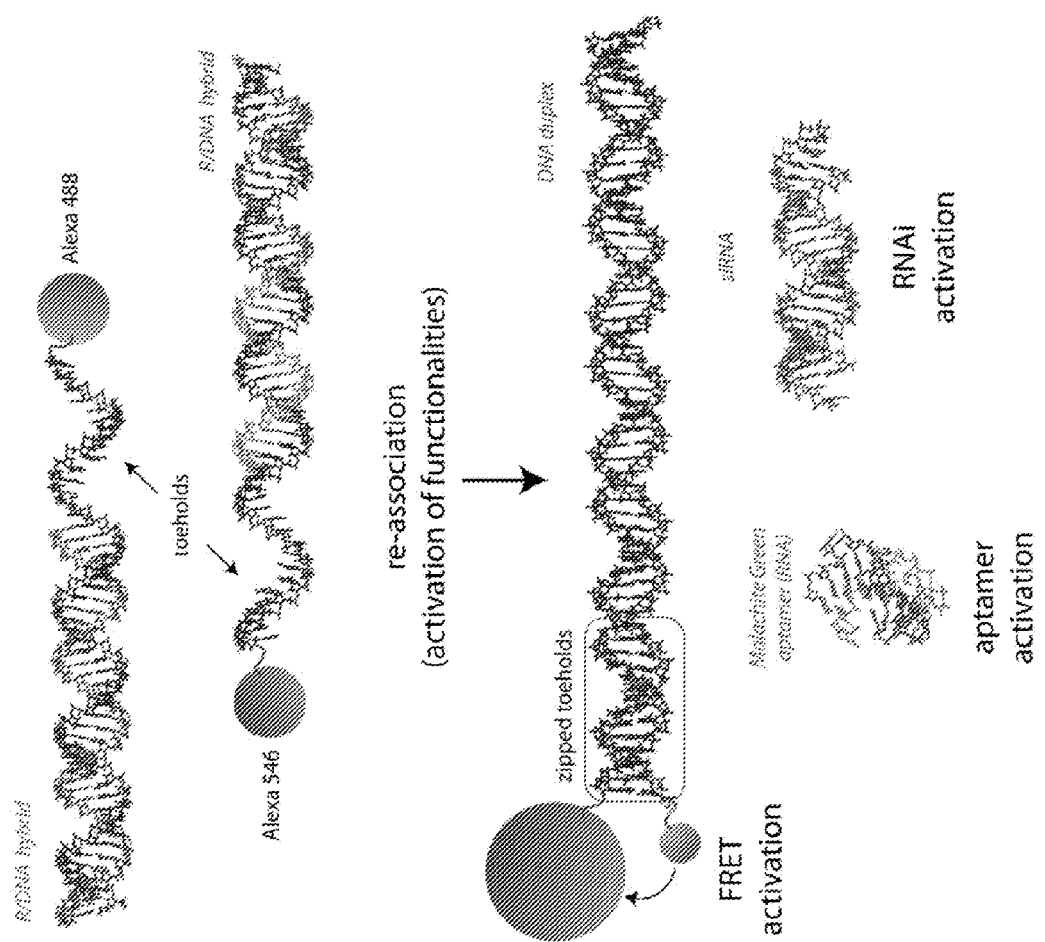

FIG. 56 is a schematic showing an exemplary auto-recognizing RNA/DNA hybrids releasing multiple functionalities (FRET response, siRNA and RNA aptamer) during re-association.

FIGS. 57A-57C show the release of multiple functionalities (FRET, siRNA, MG aptamer) upon re-association of auto-recognizing RNA/DNA hybrids. FIG. 57A is a schematic of hybrid re-association and native PAGE demonstrating the release of siRNA and MG aptamer upon re-association. FIG. 57B is the static and kinetics fluorescent experiments showing activation of MG aptamer during the release. MG by itself is non-fluorescent (blue curve) and the presence of either one of the hybrids does not activate its fluorescence (green curve). However, re-association of two cognate hybrids leads to the release of individual MG aptamer strands, their assembly and further MG uptake leading to the significant increase of its fluorescence (magenta curve). FIG. 57C upper panel: Activation of FRET during re-association. Emission spectra of control DNA duplexes showing no FRET (blue curve) and re-associated auto-recognizing R/DNA hybrids with increased Alexa546 emission signal (red curve). FIG. 57C lower panel: FRET time traces during re-association of auto-recognizing R/DNA hybrids labeled with Alexa488 and Alexa546.

Figure 58:
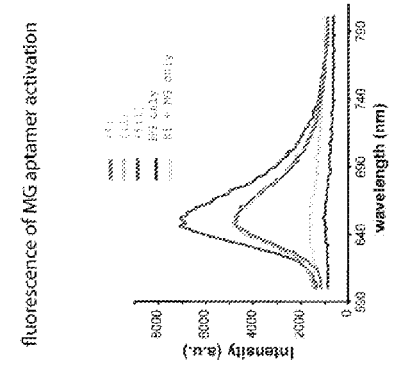
Figure 58:
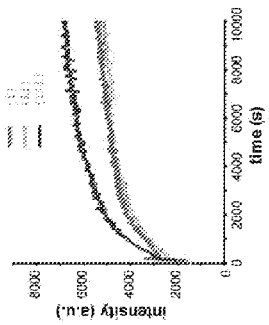
Figure 58:
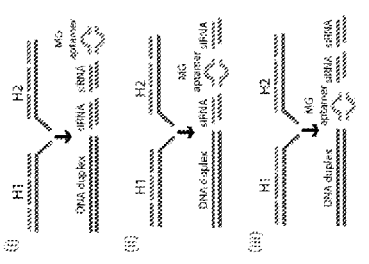
Figure 58:
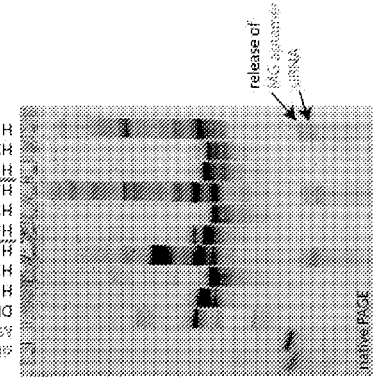

FIG. 58 shows the release of multiple functionalities (two siRNAs, MG aptamer) upon re-association of auto-recognizing RNA/DNA hybrids. MG aptamer was positioned in three different places (three sets of hybrids were tested) thus, the activation of MG fluorescence in all three cases proves the release of all functionalities (despite the position with respect to the ssDNA toeholds). Left panel: Schematic of hybrid re-association and total SYBR Gold staining native PAGE demonstrating the release of siRNAs and MG aptamer upon re-association. Right panel: Static and kinetics fluorescent experiments showing activation of MG aptamer during the release.

FIG. 59A-59D show the re-association, localization of auto-recognizing R/DNA hybrids in human breast cancer cells (MDA-MB-231) visualized by confocal fluorescence microscopy and further release of siRNAs tracked by GFP knockdown assays for human breast cancer cells (MDA-MB-231/GFP) which stably express enhanced GFP (eGFP). FIG. 59A is a schematic of different size hybrids re-association compared in these experiments. FRET experiments (FIG. 59B): cells were co-transfected with cognate hybrids labeled with Alexa488 and Alexa546 and images were taken on the next day. FIG. 59C is a gel showing total SYBR Gold staining native PAGE demonstrating the release of siRNAs. GFP knockdown assays (FIG. 59D): three days after the transfection of cells with auto-recognizing R/DNA hybrids programmed to release one (hybrids (i)), two (hybrids (ii)), and three (hybrids (iii)) siRNAs against eGFP. eGFP expression was observed by fluorescence microscopy and statistically analyzed with flow cytometry experiments. As the control, siRNA duplexes against eGFP were used. Image numbers in FIG. 59B correspond to: Alexa488 emission (1), Alexa546 emission (2), bleed-through corrected FRET image (3), differential interference contrast (DIC) image with corrected FRET overlap (4), 3D chart representation of zoomed fragment indicated by a white box of bleed-through corrected FRET image with the yellow star indicating the correspondence (5).

DETAILED DESCRIPTION OF THE INVENTION

Using RNA interference (RNAi) as a therapeutic agent it is routinely possible to knock down the expression of target genes in diseased cells. One of the ways to initiate the RNAi machinery is through the direct exogenous introduction to the cells of small interfering RNA (siRNA) duplexes. The invention described herein provides for a strategy based on therapeutic RNA/DNA hybrids which can be generally used for triggering the RNAi pathway as well as other functionalities inside the diseased cells. Individually, each of the hybrids is functionally inactive and the therapeutic siRNA representation can only be activated by the re-association of at least two cognate hybrids simultaneously present in the same cell. The invention features a method for siRNA release where cognate hybrids are co-delivered to the cell either on the same or on two different days. The invention provides for nucleic acids based "smart" nanoparticles for biomedical applications.

The invention is based on a novel strategy to design and engineer programmable auto-recognizing R/DNA hybrids capable of undergoing triggered release of embedded functionalities upon their re-association inside cells. The R/DNA hybrids have significantly higher stabilities in blood serum compared to the siRNA and that the use of the R/DNA hybrid approach allows (i) introduction of additional functionalities without direct interference of siRNA processivity, (ii) activation of split functionalities (e.g., FRET) in vitro and intracellularly, (ii) tracking of the delivery and re-association of these hybrids in real-time inside cells, (iii) the triggered release of siRNAs in cell culture and in vivo, (iv) pro-longed effect of gene silencing compared to the siRNA. Additionally, this approach may permit (i) higher control over targeting specificity (e.g. if two hybrids are decorated with two different tissue specific recognition moieties), (ii) increasing the number of functionalities by introducing a branched hybrid structure, (iii) increasing the retention time in biological fluids by fine-tuning chemical stability through substituting the DNA strands with chemical analogs (e.g. locked nucleic acids (LNA), peptide nucleic acids (PNA), etc.), (iv) conditional release of siRNAs or other functionalities. Moreover, the thermal stabilities of toehold interactions can be fine-tuned by altering their lengths and compositions. The invention opens new routes for further developments in nucleic acids based nanoparticles for a broad array of nanotechnological and biomedical applications.

The certain aspects the invention features compositions and methods that are useful for inhibiting gene expression in a subject. The invention features a therapeutic R/DNA chimeric polyfunctional nanoparticles (R/DNA NP) which are a pair of RNA/DNA duplexes where the first DNA molecule has a 5' toehold sequence and the second DNA molecule has a 3' toehold sequence wherein the 5' and 3' toehold sequences are complementary. When the two R/DNA NPs are mixed the toehold sequences form a duplex which results in the re-association of the two R/DNA NPs.

The product of re-association is a DNA/DNA duplex and an RNA/RNA duplex where the RNA duplex is designed to function as an siRNA to target a specific target RNA. The R/DNA NPs also have moieties attached which specifically bind target molecules. In one embodiment the target molecules are cell surface proteins present on cells that express a target gene. Therefore, the R/DNA NPs allow for the targeting of specific target genes in a specific cells.

The invention may be used to target medically important genes or genes in medically important cells. For example, in one embodiment, R/DNA NPs could be used to reduce viral burden in a subject by targeting virally infected cells. In specific embodiments the R/DNA NPs inhibit apoptosis inhibitors in virally infected cells thereby specifically killing the virally infected cells. In particular embodiments the virus is HIV. In other embodiments, R/DNA NPs could be used to target neoplastic cells. In additional embodiments, R/DNA NPs could inhibit a target gene in a neoplasia resulting in the death or apoptosis of the neoplasia. Thus R/DNA NPs could be used to treat any disease that is amenable to gene silencing approaches.

The invention also provides methods of treating HIV infected subjections by administering an effective amount of R/DNA NPs that targets HIV infected cells and results in the destruction of the targeted apoptosis inhibitors resulting in the death of the HIV infected cells thereby eradicating HIV from the subject.

The invention further features methods of treating a subject having neoplasia by administering an effective amount of R/DNA NPs that targets neoplastic cells and results in the knock-down of target genes that results in the death or apoptosis of the neoplastic cells.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration of a therapeutically effective amount of the compounds herein, such as a compound of the formulae herein to a subject (e.g., animal, human) in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The compounds herein may be also used in the treatment of any other disorders in which viruses, particularly HIV may be implicated.

In one embodiment, the invention provides a method of monitoring treatment progress. The method includes the step of determining a level of diagnostic marker for virus infected cells, particularly HIV infected cells (e.g., any target delineated herein modulated by a compound herein, a protein or indicator thereof, etc.) or diagnostic measurement (e.g., screen, assay) in a subject suffering from or susceptible to a disorder or symptoms thereof associated with viruses, particularly HIV, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this invention; this pre-treatment level of Marker can then be compared to the level of Marker in the subject after the treatment commences, to determine the efficacy of the treatment.

Pharmaceutical Therapeutics

The present disclosure provides R/DNA NPs that decrease the expression or activity of target proteins in diseased cells. For example, in one non-limiting embodiment, the disclosure provides pharmaceutical compositions comprising a R/DNA NPs that inhibits the expression or activity of an apoptosis inhibitor in the diseased cell. In a further embodiment, the diseased cell is a neoplastic cell or a virally infected cell. However, the pharmaceutical applications described herewith are applicable to the treatment of any disease state that is or is contemplated to be amenable to gene silencing. For therapeutic uses, the compositions or agents identified using the methods disclosed herein may be administered systemically, for example, formulated in a pharmaceutically-acceptable carrier. Preferable routes of administration include, for example, subcutaneous, intravenous, interperitoneally, intramuscular, or intradermal injections that provide continuous, sustained levels of the drug in the patient. Treatment of human patients or other animals will be carried out using a therapeutically effective amount of R/DNA NPs in a physiologically-acceptable carrier. Suitable carriers and their formulation are described, for example, in Remington's Pharmaceutical Sciences by E. W. Martin. The amount of the therapeutic agent to be administered varies depending upon the manner of administration, the age and body weight of the patient, and the clinical symptoms of disease progression. Generally, amounts will be in the range of those used for other agents used in the treatment of the disease, although in certain instances lower amounts will be needed because of the increased specificity of the compound. A compound is administered at a dosage that controls the clinical or physiological symptoms of cancer progression or metastasis as determined by a diagnostic method known to one skilled in the art, or using any that assay that measures the transcriptional activation of a gene associated with the disease.

Formulation of Pharmaceutical Compositions

The administration of a R/DNA NPs of the disclosure or analog thereof for the treatment of a disease may be by any suitable means that results in a concentration of the R/DNA NPs that, combined with other components, is effective in ameliorating, reducing, eradicating, or stabilizing the disease. In one embodiment, administration of the R/DNA NPs reduces the expression or activity of a target gene. In another embodiment, the R/DNA NPs is administered to a subject for the prevention or treatment of a disease associated with disease.

Methods of administering such R/DNA NPs are known in the art. The disclosure provides for the therapeutic administration of an agent by any means known in the art. The compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York). Suitable formulations include forms for oral administration, depot formulations, formulations for delivery by a patch, and semi-solid dosage forms to be topically or trans-dermally delivered.

Pharmaceutical compositions according to the disclosure may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively, constant, effective level in the body with concomitant minimization of undesirable side effects associated with fluctuations in the plasma level of the active substance (saw-tooth kinetic pattern); (iv) formulations that localize action by, e.g., spatial placement of a controlled release composition adjacent to or in the central nervous system or cerebrospinal fluid; (v) formulations that allow for convenient dosing, such that doses are administered, for example, once every one or two weeks; and (vi) formulations that target tumor cells by using carriers or chemical derivatives to deliver the therapeutic agent to a particular cell type whose function is perturbed in cancer. For some applications, controlled release formulations obviate the need for frequent dosing during the day to sustain the plasma level at a therapeutic level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the therapeutic is formulated with appropriate excipients into a pharmaceutical composition that, upon administration, releases the therapeutic in a controlled manner. Examples include single or multiple unit tablet or capsule compositions, oil solutions, suspensions, emulsions, microcapsules, microspheres, molecular complexes, nanoparticles, patches, and liposomes.

Parenteral Compositions

The pharmaceutical composition may be administered parenterally by injection, infusion or implantation (subcutaneous, intravenous, intramuscular, intraperitoneal, or the like) in dosage forms, formulations, or via suitable delivery devices or implants containing conventional, non-toxic pharmaceutically acceptable carriers and adjuvants. The formulation and preparation of such compositions are well known to those skilled in the art of pharmaceutical formulation. Formulations can be found in Remington: The Science and Practice of Pharmacy, supra. Compositions for parenteral use may be provided in unit dosage forms (e.g., in single-dose ampoules), or in vials containing several doses and in which a suitable preservative may be added (see below). The composition may be in the form of a solution, a suspension, an emulsion, an infusion device, or a delivery device for implantation, or it may be presented as a dry powder to be reconstituted with water or another suitable vehicle before use. Apart from the active therapeutic (s), the composition may include suitable parenterally acceptable carriers and/or excipients. The active therapeutic (s) may be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents.

As indicated above, the pharmaceutical compositions according to the disclosure may be in the form suitable for sterile injection. To prepare such a composition, the suitable active therapeutic(s) are dissolved or suspended in a parenterally acceptable liquid vehicle.

Controlled Release Parenteral Compositions

Controlled release parenteral compositions may be in the form of suspensions, microspheres, microcapsules, magnetic microspheres, oil solutions, oil suspensions, or emulsions. Alternatively, the active drug may be incorporated in biocompatible carriers, liposomes, nanoparticles, implants, or infusion devices. Materials for use in the preparation of microspheres and/or microcapsules are, e.g., biodegradable/bioerodible polymers such as polygalactin, poly-(isobutyl cyanoacrylate), poly(2-hydroxyethyl-L-glutam-nine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly (lactic acid), poly(glycolic acid) or poly(ortho esters) or combinations thereof).

Inhibitory Nucleic Acids

The R/DNA NPs molecules described herein operate by forming inhibitory nucleic acid molecules once in target cells. Such inhibitory nucleic acids include single and double stranded nucleic acid molecules (e.g., DNA, RNA, and analogs thereof) that bind a nucleic acid molecule that encodes target RNA (e.g., antisense oligonucleotide molecules, siRNA, shRNA) as well as nucleic acid molecules that bind directly to a target polypeptide to modulate its biological activity (e.g., aptamers).

Ribozymes

Catalytic RNA molecules or ribozymes that include an antisense target RNA sequence of the present disclosure can be used to inhibit expression of target RNAs in vivo. The inclusion of ribozyme sequences within antisense RNAs confers RNA-cleaving activity upon them, thereby increasing the activity of the constructs. The design and use of target RNA-specific ribozymes is described in Haseloff et al., Nature 334:585-591. 1988, and U.S. Patent Application Publication No. 2003/0003469 A1, each of which is incorporated by reference.

Accordingly, the disclosure also features a catalytic RNA molecule that includes, in the binding arm, an antisense RNA having between eight and nineteen consecutive nucleobases. In preferred embodiments of this disclosure, the catalytic nucleic acid molecule is formed in a hammerhead or hairpin motif. Examples of such hammerhead motifs are described by Rossi et al., Aids Research and Human Retroviruses, 8:183, 1992. Example of hairpin motifs are described by Hampel et al., "RNA Catalyst for Cleaving Specific RNA Sequences," filed Sep. 20, 1989, which is a continuation-in-part of U.S. Ser. No. 07/247,100 filed Sep. 20, 1988, Hampel and Tritz, Biochemistry, 28:4929, 1989, and Hampel et al., Nucleic Acids Research, 18: 299, 1990. These specific motifs are not limiting in the disclosure and those skilled in the art will recognize that all that is important in an enzymatic nucleic acid molecule of this disclosure is that it has a specific substrate binding site which is complementary to one or more of the target gene RNA regions, and that it have nucleotide sequences within or surrounding that substrate binding site which impart an RNA cleaving activity to the molecule.

Small hairpin RNAs consist of a stem-loop structure with optional 3' UU-overhangs. While there may be variation, stems can range from 21 to 31 bp (desirably 25 to 29 bp), and the loops can range from 4 to 30 bp (desirably 4 to 23 bp). For expression of shRNAs within cells, plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

siRNA

Short twenty-one to twenty-five nucleotide double-stranded RNAs are effective at down-regulating gene expression (Zamore et al., Cell 101: 25-33; Elbashir et al., Nature 411: 494-498, 2001, hereby incorporated by reference). The therapeutic effectiveness of an siRNA approach in mammals was demonstrated in vivo by McCaffrey et al. (Nature 418: 38-39, 2002). Given the sequence of a target gene, siRNAs may be designed to inactivate that gene. Such siRNAs, for example, could be administered directly to an affected tissue, or administered systemically. The nucleic acid sequence of an Parl gene can be used to design small interfering RNAs (siRNAs). The 21 to 25 nucleotide siRNAs may be used, for example, as therapeutics to inhibit disease related genes.

The inhibitory nucleic acid molecules of the present disclosure may be employed as double-stranded RNAs for RNA interference (RNAi)-mediated knock-down of target RNA expression. In therapeutic embodiments, the target RNA is a disease related gene. For example, in a non-limiting embodiment, the target RNA is a gene that is involved in cancer development or progression. In another embodiment, target RNA expression is reduced in a virus infected cell. In another embodiment, the target RNA encodes apoptosis inhibitor proteins and the cells are infected with HIV. RNAi is a method for decreasing the cellular expression of specific proteins of interest (reviewed in Tuschl, ChemBioChem 2:239-245, 2001; Sharp, Gene Dev 15:485-490, 2000; Hutvagner and Zamore, Curr Opin Genet Devel 12:225-232, 2002; and Hannon, Nature 418: 244-251, 2002). The introduction of siRNAs into cells either by transfection of dsRNAs or through expression of siRNAs using a plasmid-based expression system is increasingly being used to create loss-of-function phenotypes in mammalian cells.

In one embodiment of the disclosure, a double-stranded RNA (dsRNA) molecule is made that includes between eight and nineteen consecutive nucleobases of a nucleobase oligomer of the disclosure. The dsRNA can be two distinct strands of RNA that have duplexed, or a single RNA strand that has self-duplexed (small hairpin (sh)RNA). Typically, dsRNAs are about 21 or 22 base pairs, but may be shorter or longer (up to about 29 nucleobases) if desired. dsRNA can be made using standard techniques (e.g., chemical synthesis or in vitro transcription). Kits are available, for example, from Ambion (Austin, Tex.) and Epicentre (Madison, Wis.). Methods for expressing dsRNA in mammalian cells are described in Brummelkamp et al. Science 296:550-553, 2002; Paddison et al. Gene Dev 16:948-958, 2002. Paul et al. Nat Biotechnol 20:505-508, 2002; Sui et al. Proc Natl Acad Sci USA 99:5515-5520, 2002; Yu et al. Proc Natl Acad Sci USA 99:6047-6052, 2002; Miyagishi et al. Nat Biotechnol 20:497-500, 2002; and Lee et al. Nat Biotechnol 20:500-505, 2002, each of which is hereby incorporated by reference. In certain embodiments, the sense strand of the double stranded siRNA is split into two smaller oligonucleotides, also referred to as three stranded siRNA.

Small hairpin RNAs consist of a stem-loop structure with optional 3' UU-overhangs. While there may be variation, stems can range from 21 to 31 bp (desirably 25 to 29 bp), and the loops can range from 4 to 30 bp (desirably 4 to 23 bp). For expression of shRNAs within cells, plasmid vectors containing either the polymerase III H1-RNA or U6 promoter, a cloning site for the stem-looped RNA insert, and a 4-5-thymidine transcription termination signal can be employed. The Polymerase III promoters generally have well-defined initiation and stop sites and their transcripts lack poly(A) tails. The termination signal for these promoters is defined by the polythymidine tract, and the transcript is typically cleaved after the second uridine. Cleavage at this position generates a 3' UU overhang in the expressed shRNA, which is similar to the 3' overhangs of synthetic siRNAs. Additional methods for expressing the shRNA in mammalian cells are described in the references cited above.

The invention encompasses stabilized R/DNA NPs having modifications that protect against 3' and 5' exonucleases as well as endonucleases. Such modifications desirably maintain target affinity while increasing stability in vivo. In various embodiments, R/DNA NPs of the invention include chemical substitutions at the ribose and/or phosphate and/or base positions of a given nucleobase sequence. For example, R/DNA NPs of the invention include chemical modifications at the 2' position of the ribose moiety, circularization of the aptamer, 3' capping and 'spiegelmer' technology. R/DNA NPs having A and G nucleotides sequentially replaced with their 2'-OCH3 modified counterparts are particularly useful in the methods of the invention. Such modifications are typically well tolerated in terms of retaining affinity and specificity. In various embodiments, R/DNA NPs include at least 10%, 25%, 50%, or 75% modified nucleotides. In other embodiments, as many as 80-90% of the R/DNA NPs' nucleotides contain stabilizing substitutions. In other embodiments, 2'-OMe containing R/DNA NPs are synthesized. Such R/DNA NPs are desirable because they are inexpensive to synthesize and natural polymerases do not accept 2'-OMe nucleotide triphosphates as substrates so that 2'-OMe nucleotides cannot be recycled into host DNA. Using methods described herein, R/DNA NPs will be selected for increased in vivo stability. In one embodiment, R/DNA NPs having 2'-F and 2'-OCH$_3$ modifications are used to generate nuclease resistant aptamers. In other embodiments, the nucleic acids of the invention have one or more locked nucleic acids (LNA). LNA refers to a modified RNA nucleotide. The ribose of the LNA is modified with an extra bridge connecting the 2' oxygen and the 4' carbon which locks the ribose into the North or 3'-endo conformation. See e.g., Kaur, H. et al., *Biochemistry*, vol. 45, pages 7347-55; and Koshkin, A. A., et al., *Tetrahedron*, vol. 54, pages 3607-3630. In other embodiments, one or more nucleic acids of the invention incorporate a morpolino structure where the nucleic acid bases are bound to morpholine rings instead of deoxyribose rings and are linked through phosphorodiamidate groups instead of phosphates. See eg., Summerton, J. and Weller, D., *Antisense & Nucleic Acid Drug Development*, vol. 7, pages 187-195. Yet other modifications, include (PS)-phosphate sulfur modifications wherein the phosphate backbone of the nucleic acid is modified by the substitution of one or more sulfur groups for oxygen groups in the phosphate backbone. Other modifications that stabilize nucleic acids are known in the art and are described, for example, in U.S. Pat. No. 5,580,737; and in U.S. Patent Application Publication Nos. 20050037394, 20040253679, 20040197804, and 20040180360.

Delivery of Nucleotide-Base Oligomers

Naked inhibitory nucleic acid molecules, or analogs thereof, are capable of entering mammalian cells and inhibiting expression of a gene of interest. Nonetheless, it may be desirable to utilize a formulation that aids in the delivery of oligonucleotides or other nucleobase oligomers to cells to deliver the claimed R/DNA NPs (see, e.g., U.S. Pat. Nos. 5,656,611, 5,753,613, 5,785,992, 6,120,798, 6,221,959, 6,346,613, and 6,353,055, each of which is hereby incorporated by reference).

Dosage

Human dosage amounts can initially be determined by extrapolating from the amount of compound used in mice, as a skilled artisan recognizes it is routine in the art to modify the dosage for humans compared to animal models. In certain embodiments it is envisioned that the dosage may vary from between about 1 mg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, 5000 mg/Kg body weight. In other embodiments, it is envisaged that higher does may be used, such doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient.

Therapeutic Methods

The present disclosure provides methods of treating diseases, particularly neoplasia and viral infections by specifically inhibiting or reducing one or more target genes in specific target cells. The methods comprise administering a therapeutically effective amount of R/DNA NPs to a subject wherein the R/DNA NPs bind and enter a target cell. Once inside the target cell, the R/DNA NPs recombine through toehold sequences present in the DNA oligonucleotides. The re-association release functional RNA molecules. In one embodiment, the RNA molecules are complementary and form a duplex that is an siRNA. The release siRNA inhibits a target gene resulting in the treatment of the disease cell. The method includes the step of administering to the subject a therapeutic amount or an amount of a compound herein sufficient to treat the disease or symptom thereof, under conditions such that the disease is treated.

The methods herein include administering to the subject (including a subject identified as in need of such treatment) an effective amount of a compound described herein, or a composition described herein to produce such effect. Identifying a subject in need of such treatment can be in the judgment of a subject or a health care professional and can be subjective (e.g. opinion) or objective (e.g. measurable by a test or diagnostic method).

The therapeutic methods of the disclosure, which include prophylactic treatment, in general comprise administration of a therapeutically effective amount of the agent herein, such as a compound of the formulae herein to a subject (e.g., animal, human) in need thereof, including a mammal, particularly a human. Such treatment will be suitably administered to subjects, particularly humans, suffering from, having, susceptible to, or at risk for a cancer progression or metastasis or symptom thereof. Determination of those subjects "at risk" can be made by any objective or subjective determination by a diagnostic test or opinion of a subject or health care provider (e.g., genetic test, enzyme or protein marker, Marker (as defined herein), family history, and the like). The agent herein may be also used in the treatment of any other disorders in which transcriptional activity may be implicated.

In one embodiment, the disclosure provides a method of monitoring treatment progress. The method includes the step of determining a level of diagnostic marker (Marker) (e.g., a marker indicative of neoplasia or viral infection) or diagnostic measurement (e.g., screen, assay) in a subject suffering from or susceptible to a disease, in which the subject has been administered a therapeutic amount of a compound herein sufficient to treat the disease or symptoms thereof. The level of Marker determined in the method can be compared to known levels of Marker in either healthy normal controls or in other afflicted patients to establish the subject's disease status. In one embodiment, the Marker is indicative of neoplasia or viral infection. In preferred embodiments, a second level of Marker in the subject is determined at a time point later than the determination of the first level, and the two levels are compared to monitor the course of disease or the efficacy of the therapy. In certain preferred embodiments, a pre-treatment level of Marker in the subject is determined prior to beginning treatment according to this disclosure; this pre-treatment level of Marker can then be compared to the level of Marker in the subject after the treatment commences, to determine the efficacy of the treatment.

Kits

The disclosure provides kits for the treatment or prevention of disease. In one embodiment, the kit includes a therapeutic or prophylactic composition containing an effective amount of an agent of the invention (e.g., R/DNA NPs) in unit dosage form. In some embodiments, the kit comprises a sterile container which contains a therapeutic or prophylactic compound; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments.

If desired an agent of the disclosure is provided together with instructions for administering it to a subject having or at risk of developing a disease. The instructions will generally include information about the use of the composition for the treatment or prevention of the disease (e.g., neoplasia or viral infection). In other embodiments, the instructions include at least one of the following: description of the compound; dosage schedule and administration for treatment or prevention of the disease or symptoms thereof; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

Combination Therapies

Compositions and methods of the disclosure may be used in combination with any conventional therapy known in the art. In one embodiment, a composition of the disclosure (e.g., a composition comprising a R/DNA NPs) having anti-HIV activity may be used in combination with any anti-viral known in the art. In other embodiments, a composition comprising R/DNA NPs having anti-neoplastic activity may be used as an adjuvant to surgery or in combination with one or more anti-neoplastic chemotherapeutic. In certain embodiments the one or more chemotherapeutics is selected from abiraterone acetate, altretamine, anhydrovinblastine, auristatin, bexarotene, bicalutamide, BMS184476,2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvincaleukoblastine, docetaxol, doxetaxel, cyclophosphamide, carboplatin, carmustine (BCNU), cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

Recombinant Polypeptide Expression

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Example 1

Design of Self-Recognizing Hybrid Duplexes

Figure 2:
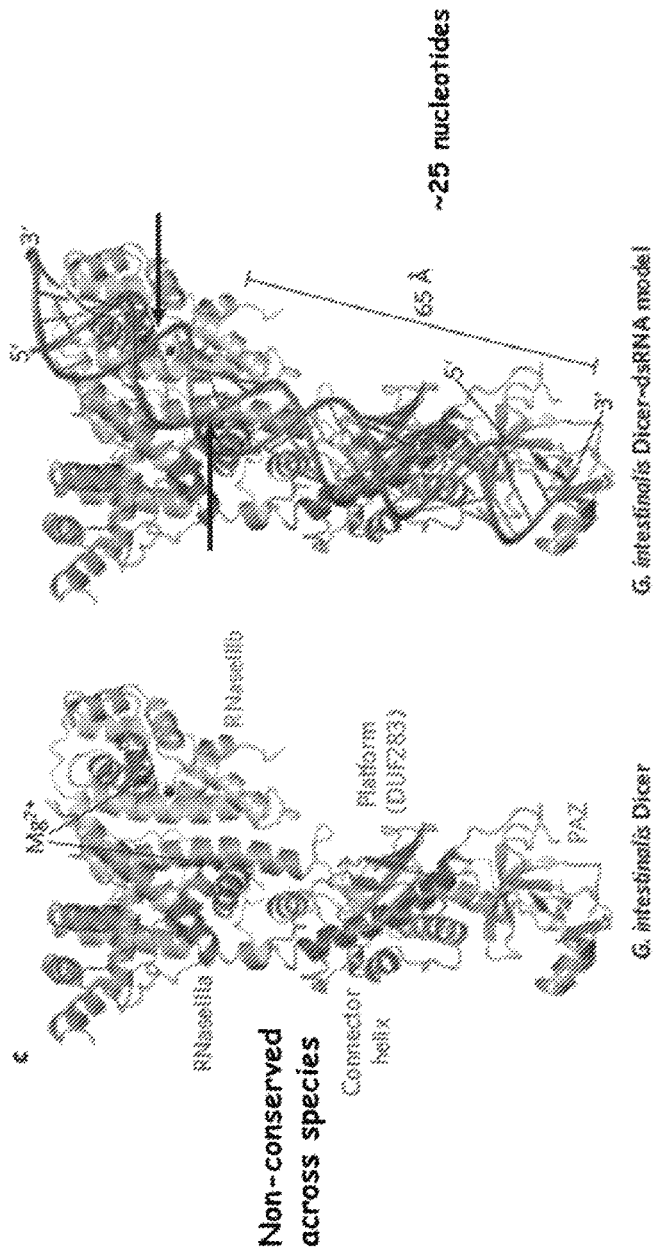
FIG. 2 shows the structural characteristics of the Dicer enzyme.
Figure 3:
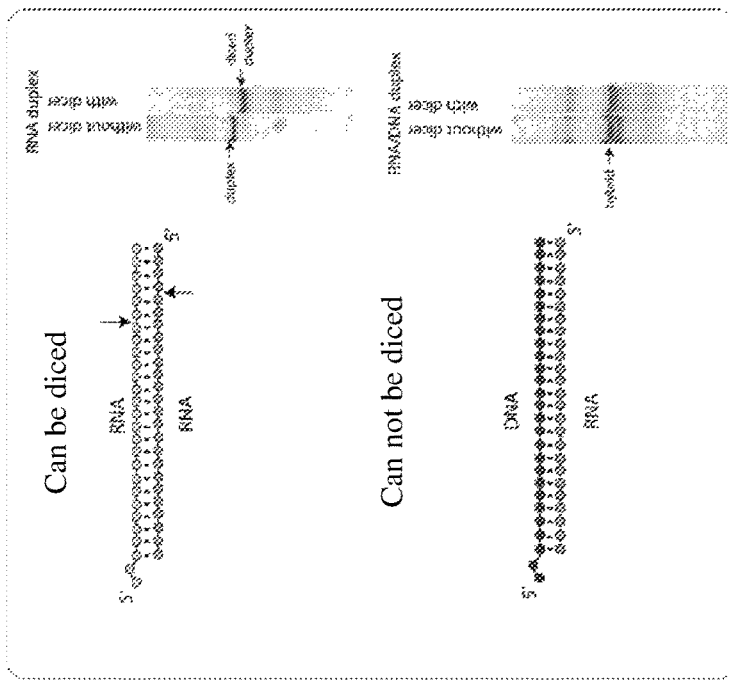
FIG. 3 is a schematic showing that Dicer can cleave double stranded RNA but not DNA/RNA hybrids.
Figure 4:
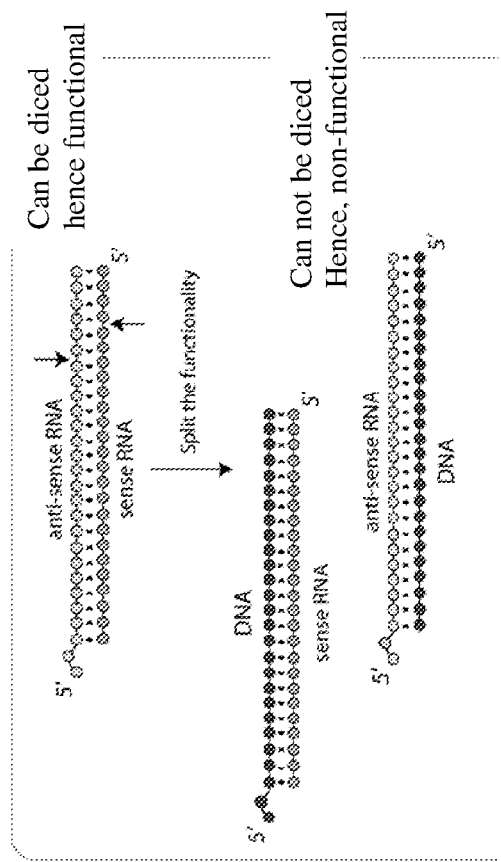
FIG. 4 is a schematic that illustrates the first step in the design of self-recognizing hybrid duplexes.
Figure 5:
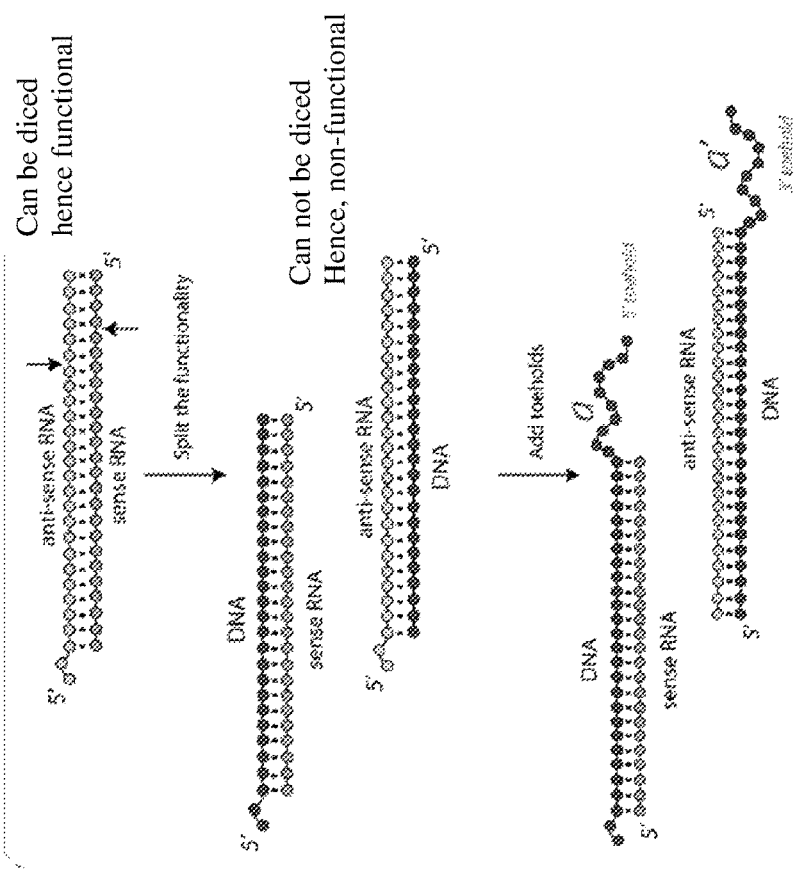
FIG. 5 is a schematic that illustrates the second step in the design of self-recognizing hybrid duplexes—the addition of toehold sequences.
Figure 6:
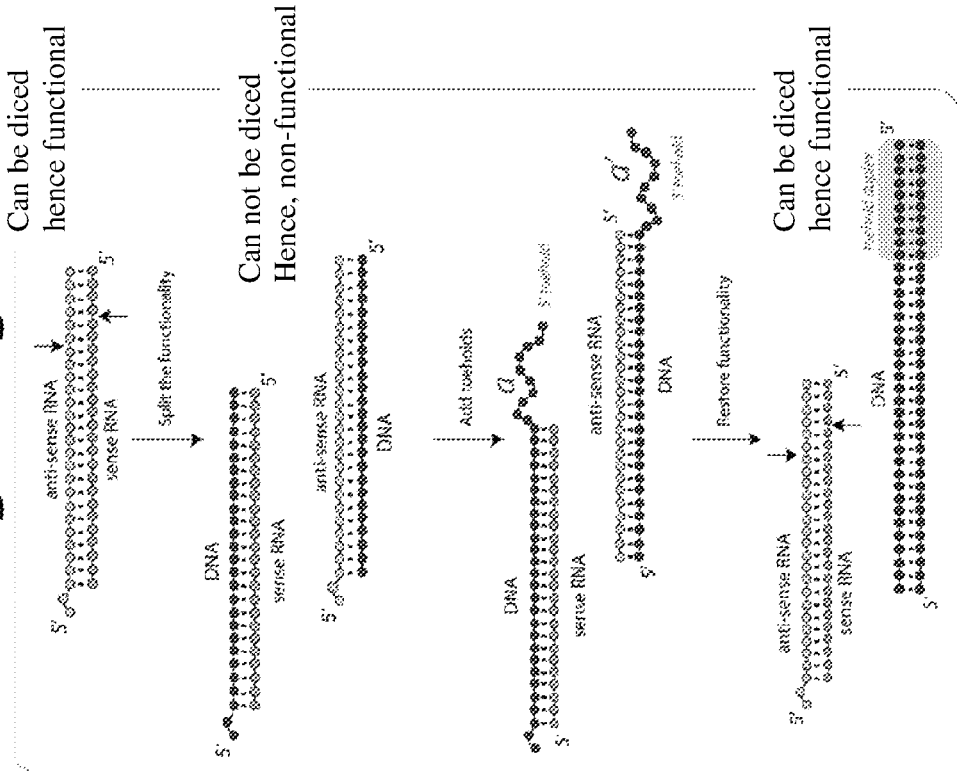
FIG. 6 is a schematic that illustrates the operation of the designed self-recognizing hybrid duplexes.
Figure 7:
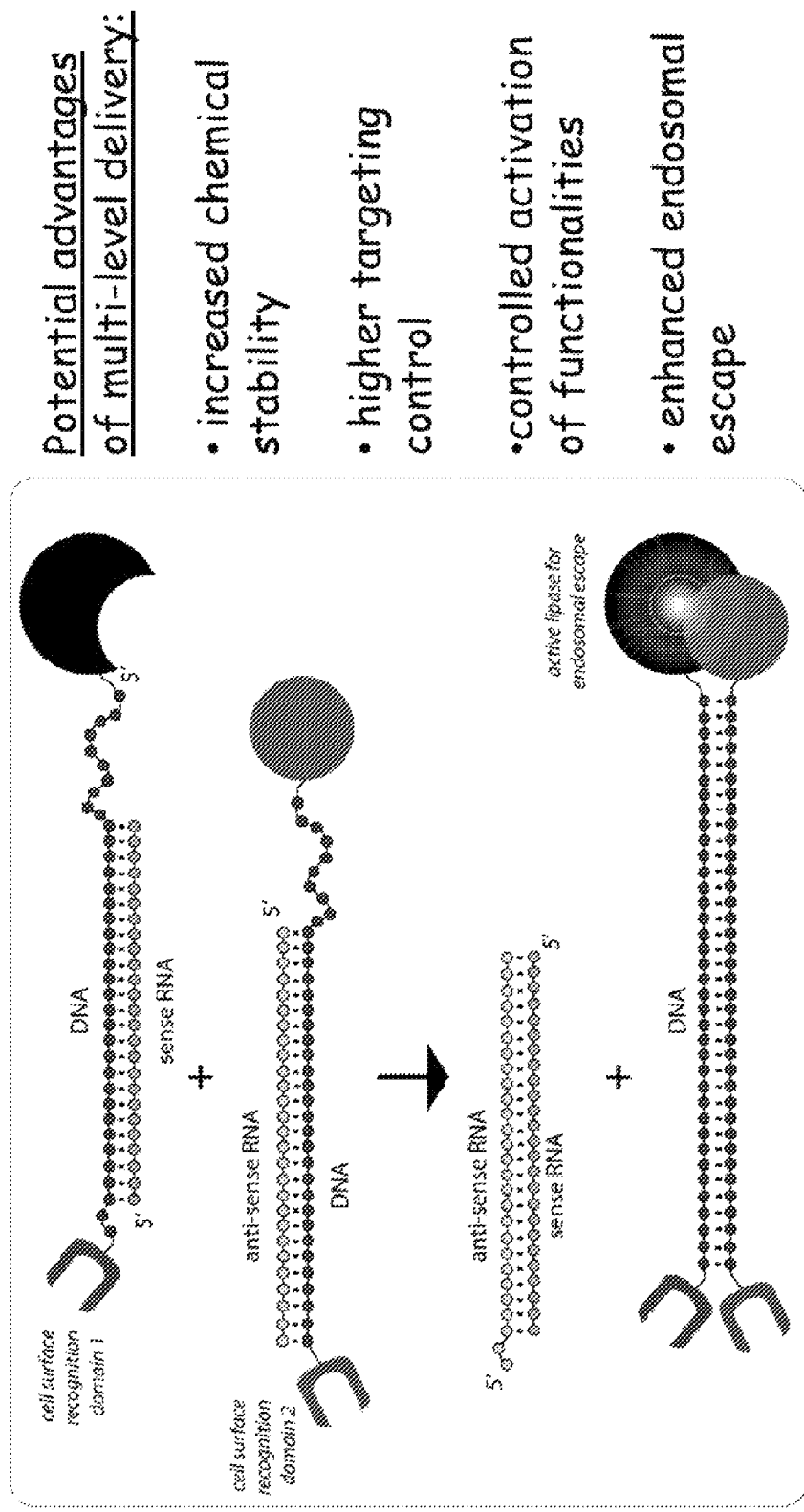
FIG. 7 is a schematic that illustrates the operation of auto-activated therapeutics.
Figure 8:
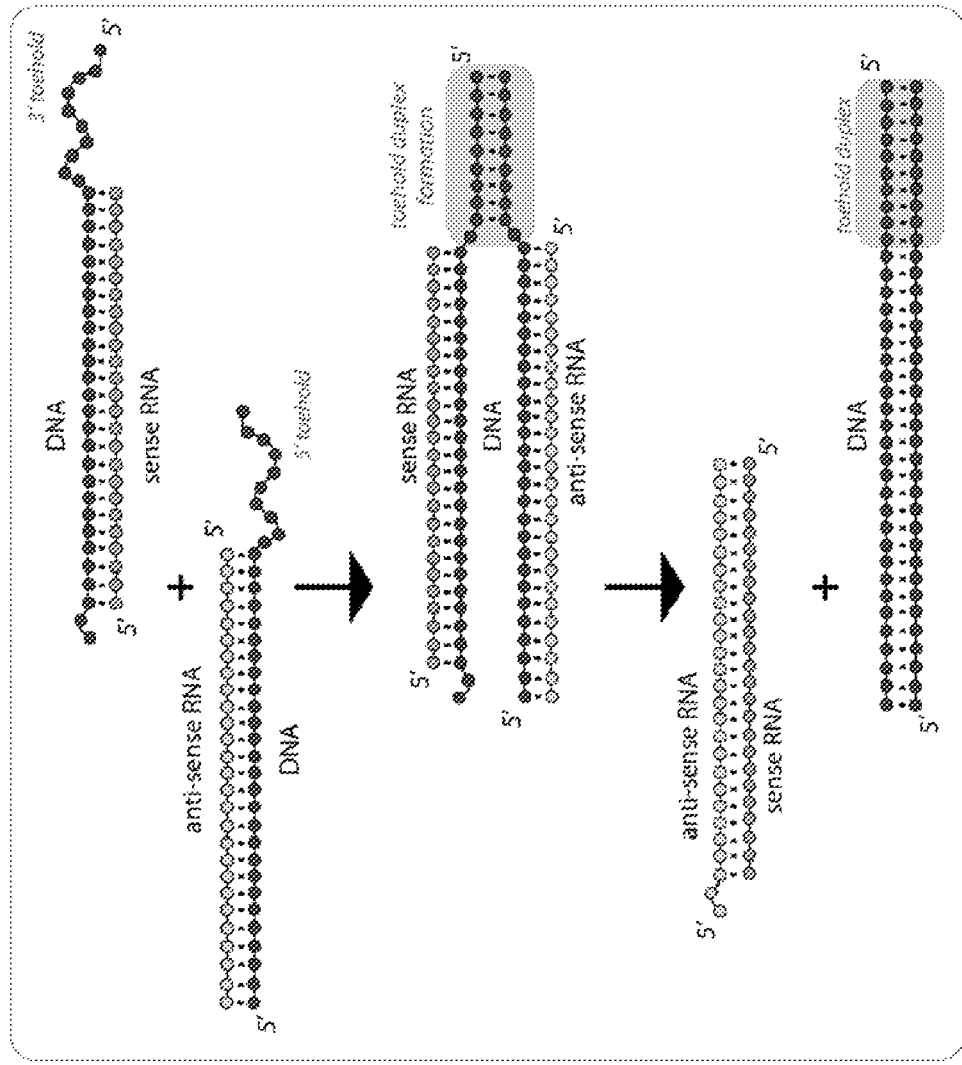
FIG. 8 is a schematic that illustrates how the presence of the complementary toehold sequences in each of the self-recognizing hybrids form toehold duplexes which result in the formation of an RNA duplex.
Figure 9:
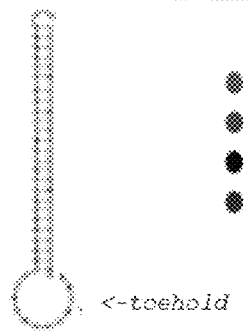
FIG. 9 illustrates the use of rationale design to produce the self-recognizing particles.
Figure 9:
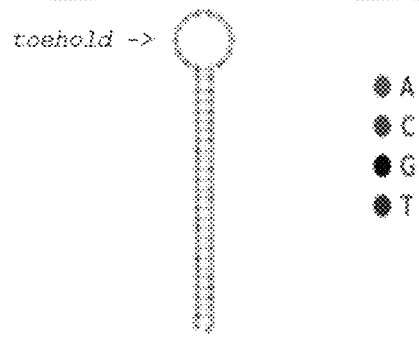
Figure 9:
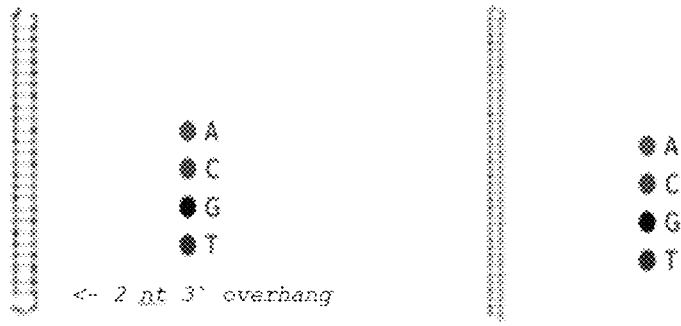
Figure 10:
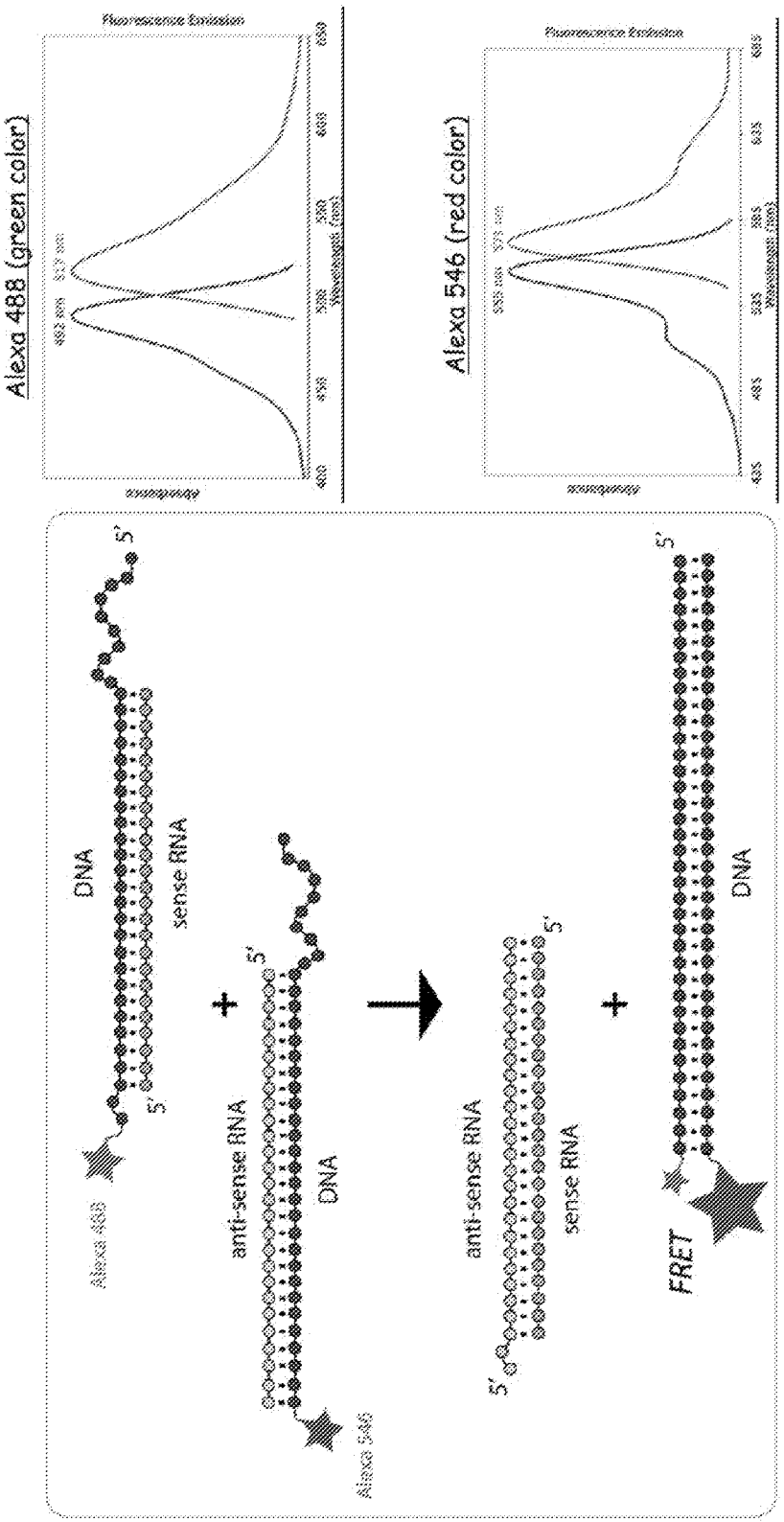
FIG. 10 shows the in vitro formation of hybrid re-association as measured by FRET.
Figure 11:
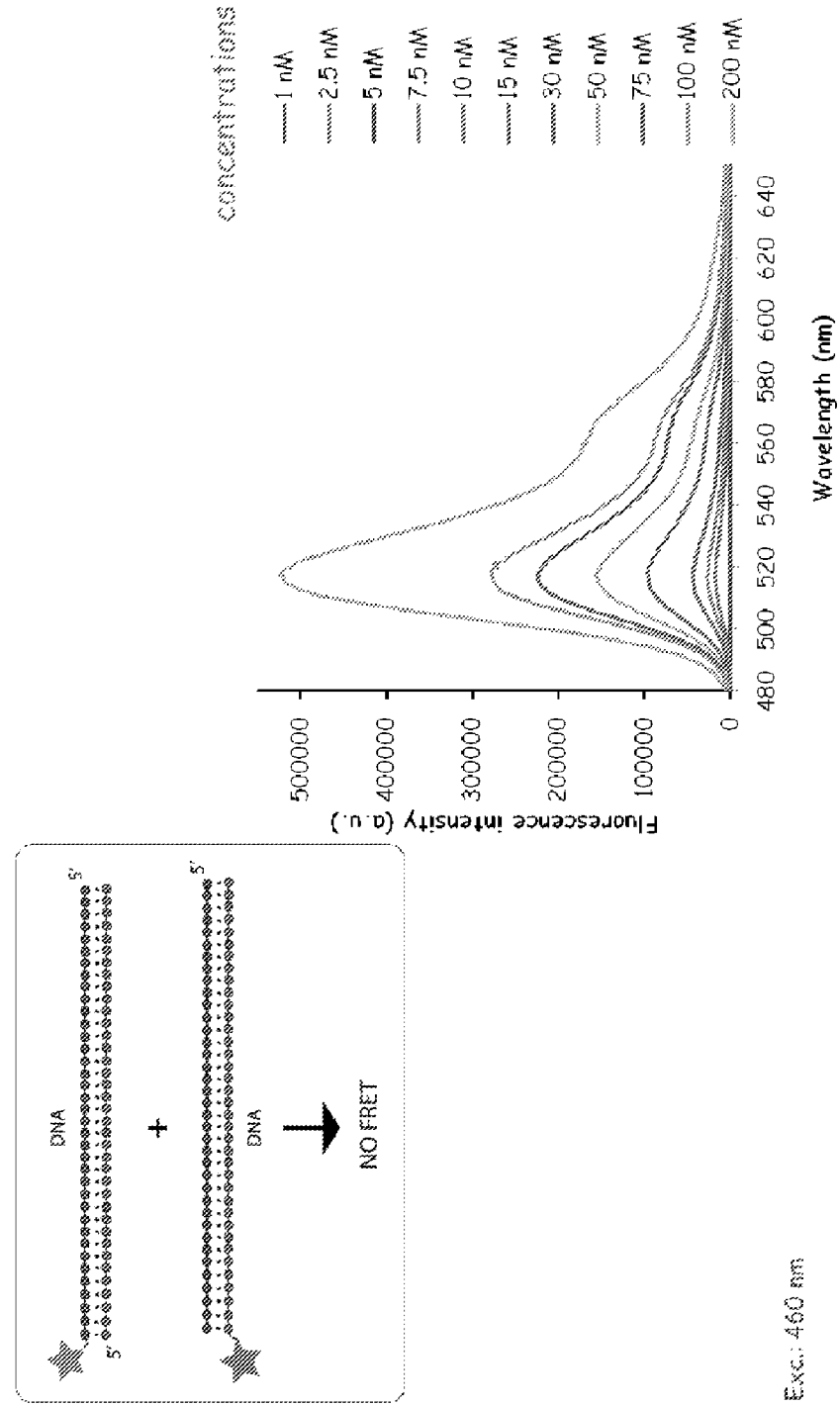
FIG. 11 shows the affinity of hybrid re-association using the negative control—duplexes without toeholds.
Figure 12:
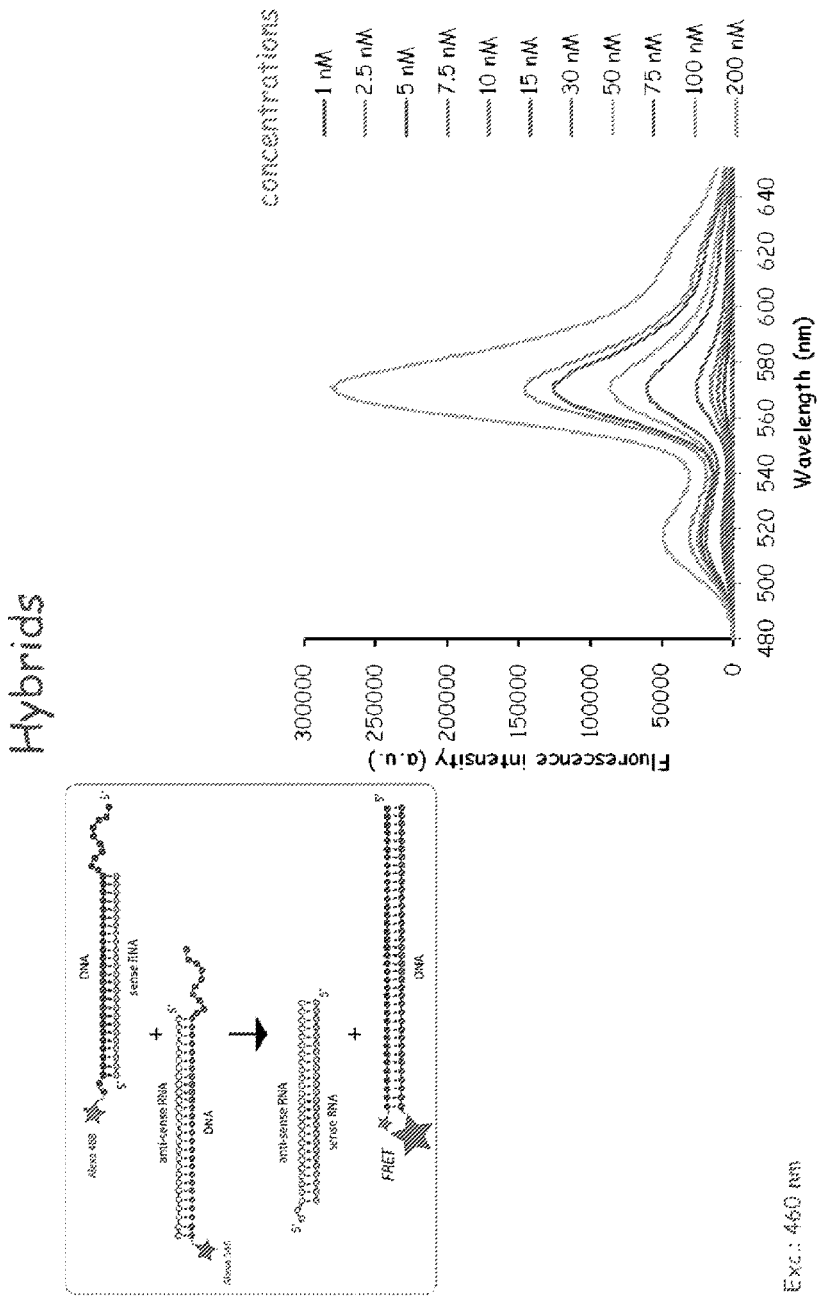
FIG. 12 shows the affinity of hybrid re-association using duplexes with toeholds.
Figure 13:
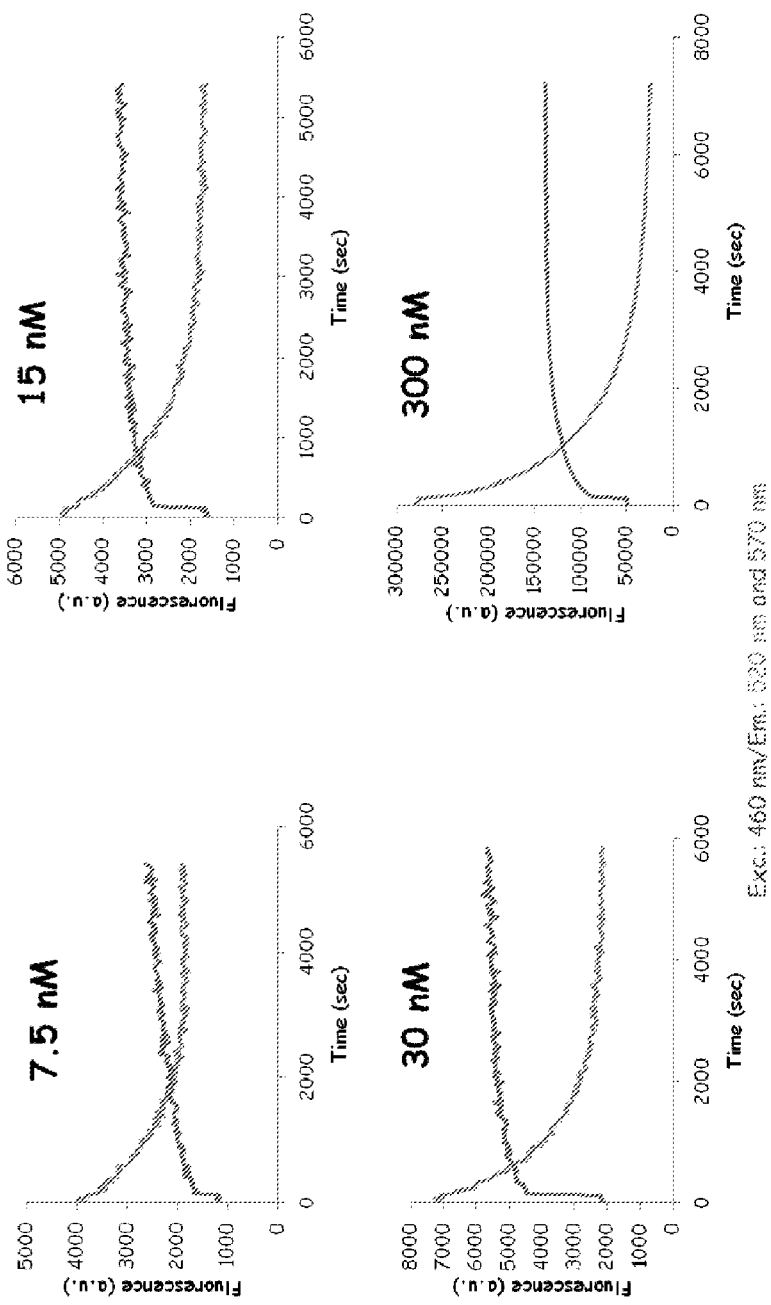
FIG. 13 are a set of graphs that show the kinetics of hybrid recombination.
Figure 14:
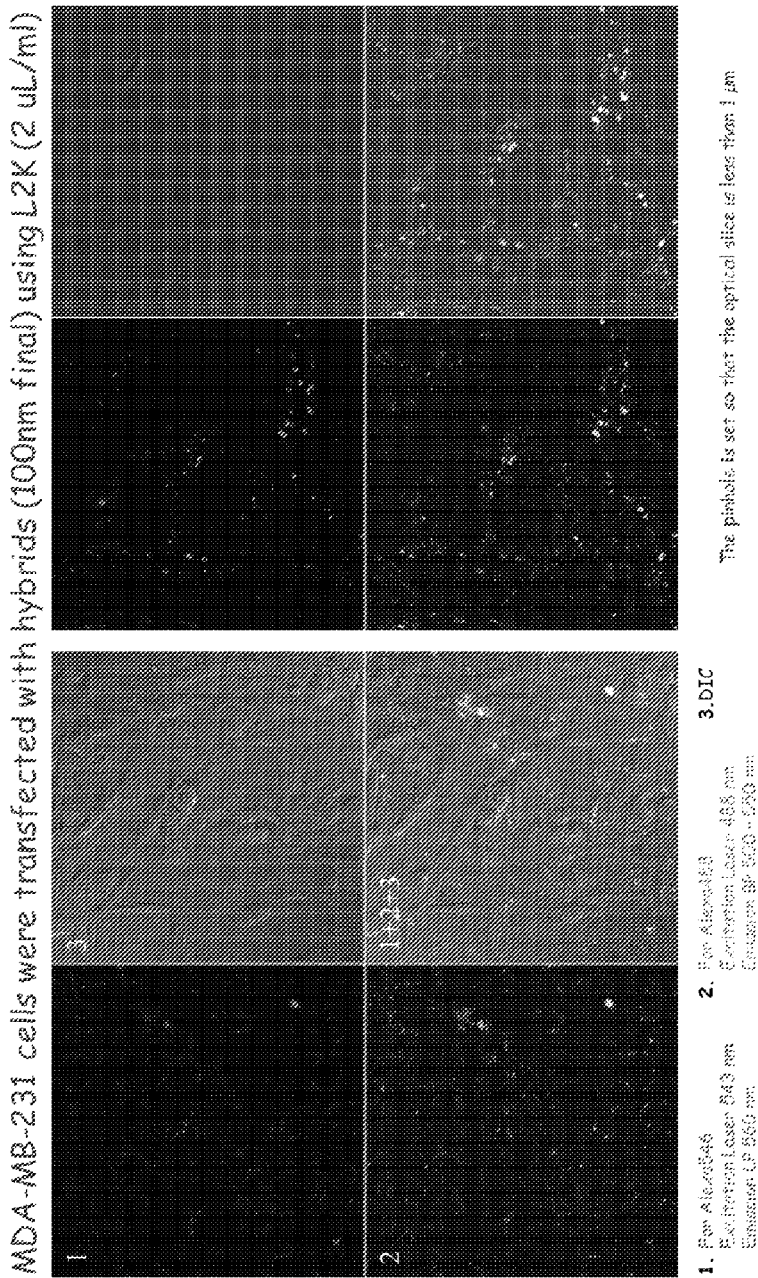
FIG. 14 shows the tracking of re-association of hybrids in vivo.
Figure 15:
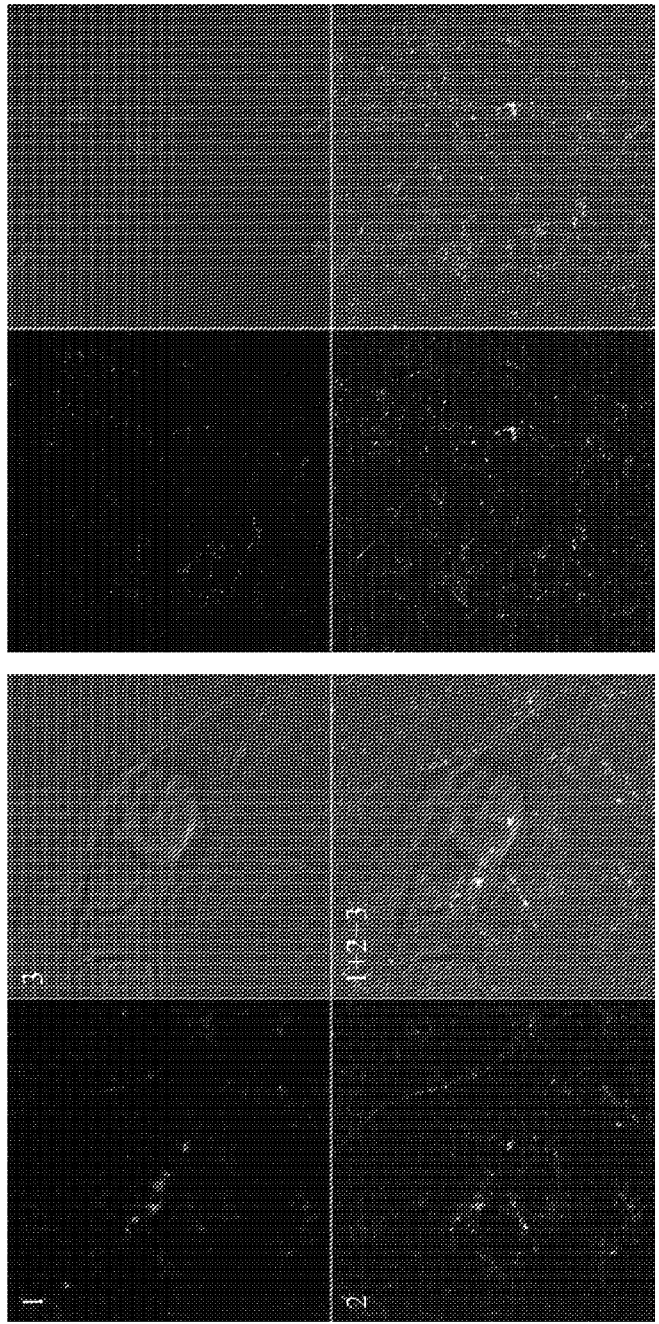
FIG. 15 shows the tracking of re-association of hybrids in living cells.
Figure 16:
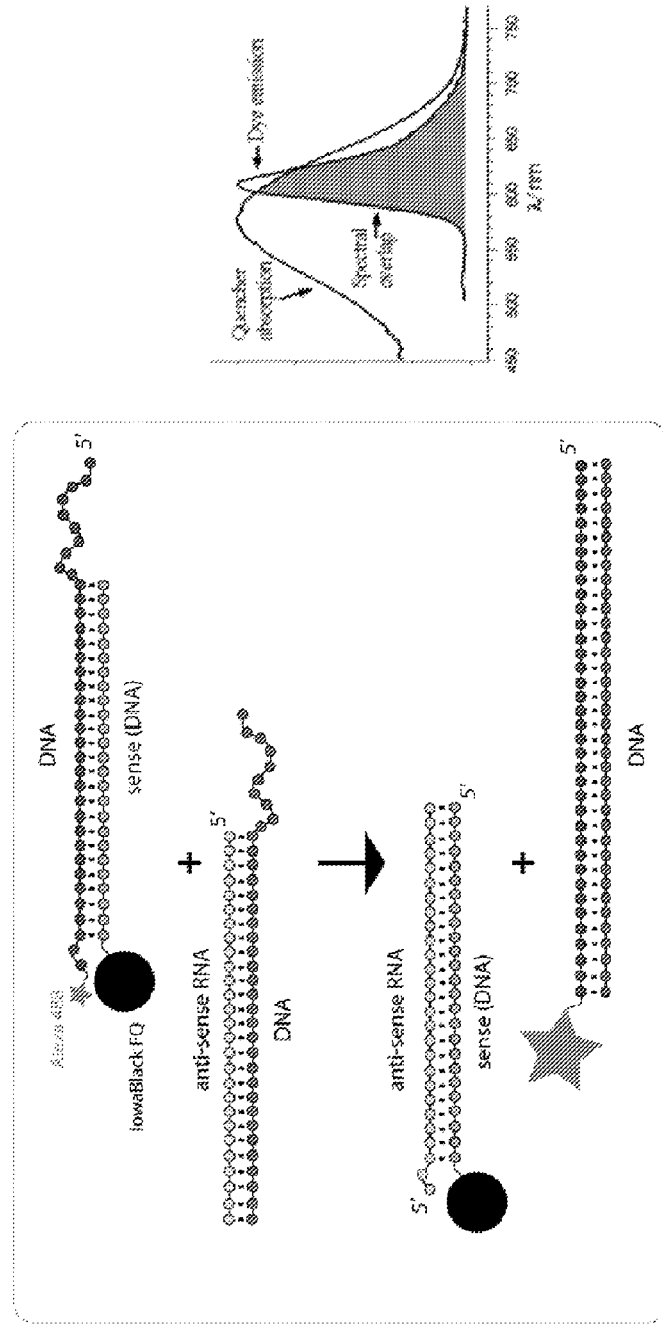
FIG. 16 illustrates how re-association can be monitored in vitro through de-quenching (FRET).
Figure 17:
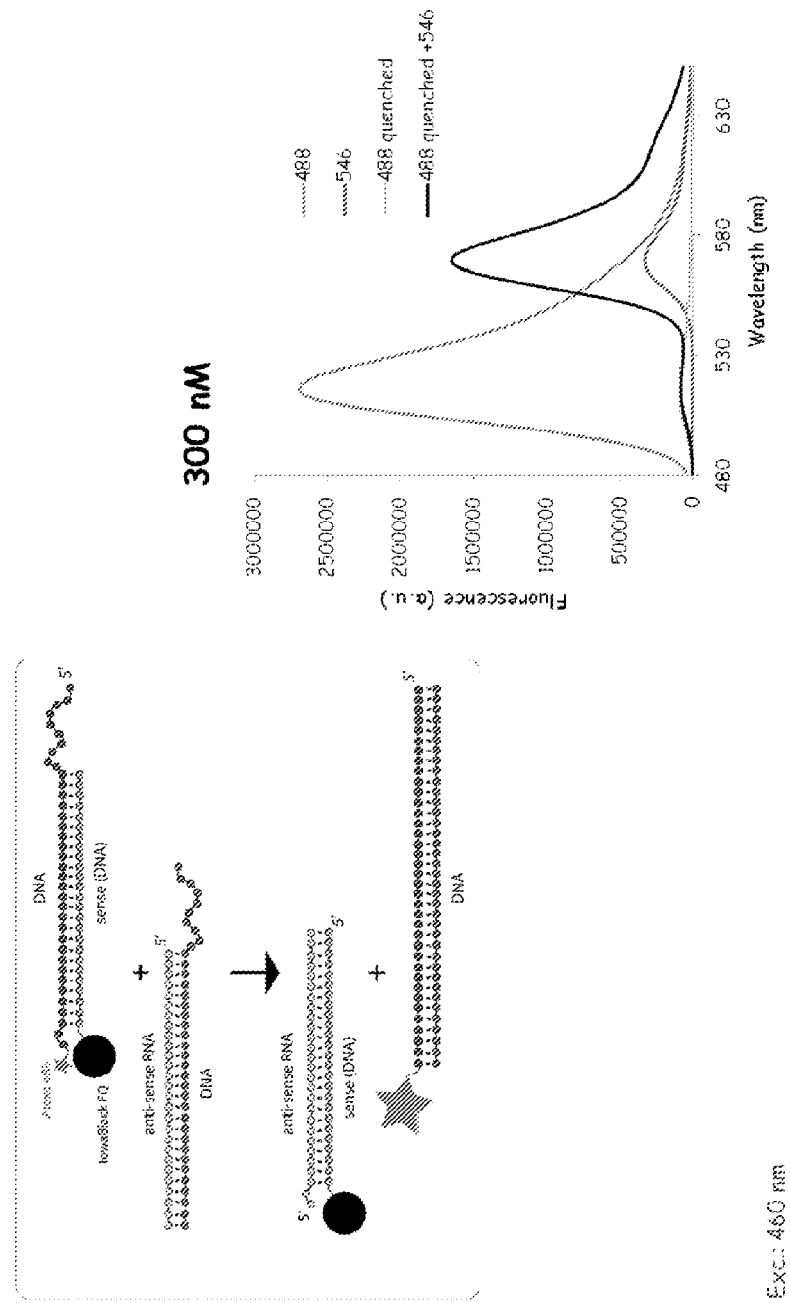
FIG. 17 is an illustrative example of tracking re-association in vitro.
Figure 18:
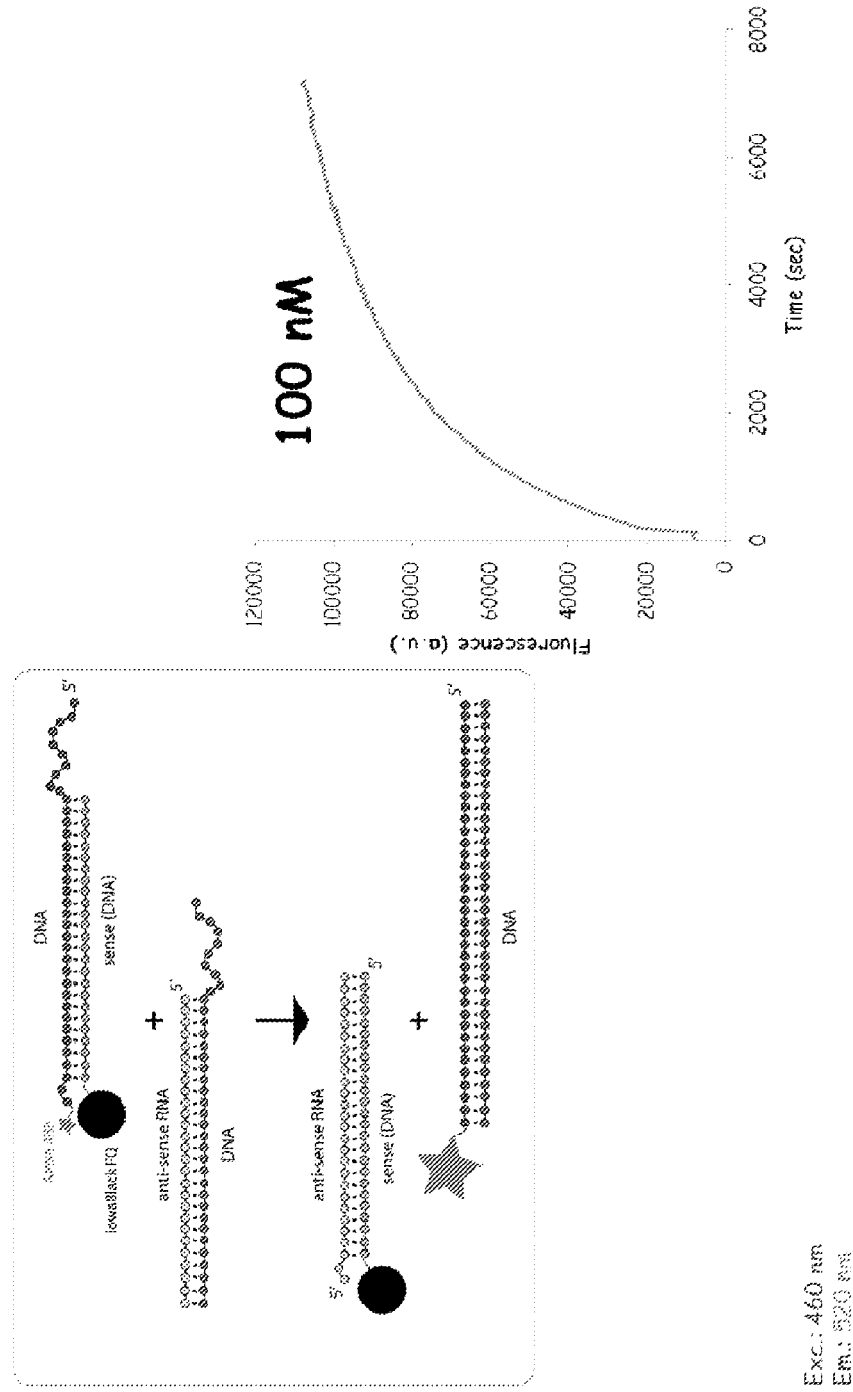
FIG. 18 is an illustrative example of the kinetics of hybrid de-quenching.
Figure 19:
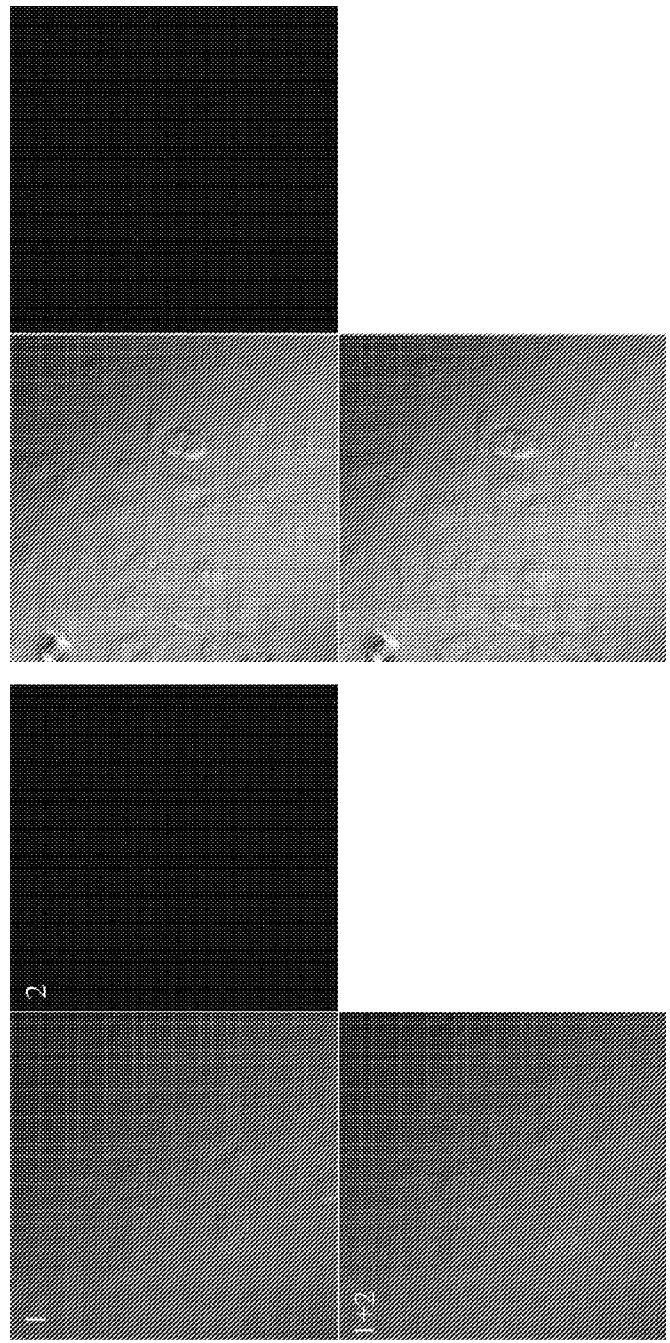
FIG. 19 shows the tracking of re-association of hybrids inside living cells through de-quenching.
Figure 20:
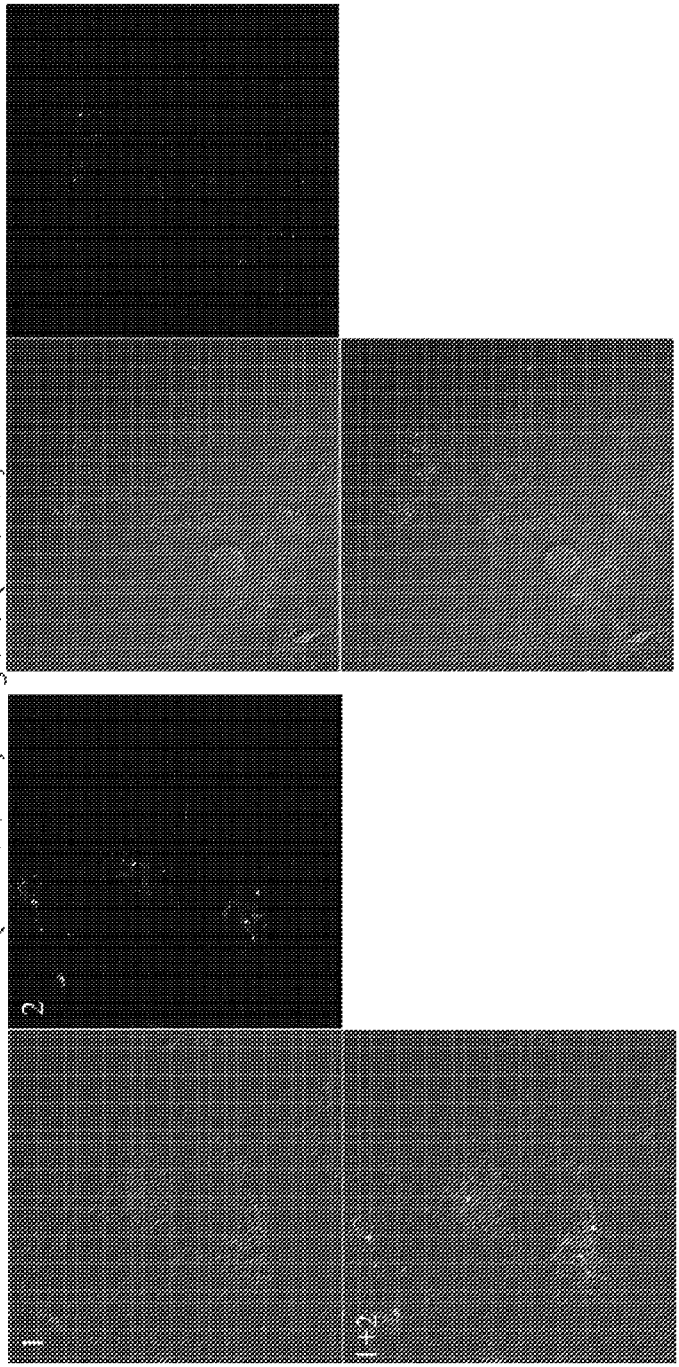
FIG. 20 shows the tracking of the re-association of hybrids inside living cells through de-quenching.
Figure 21:
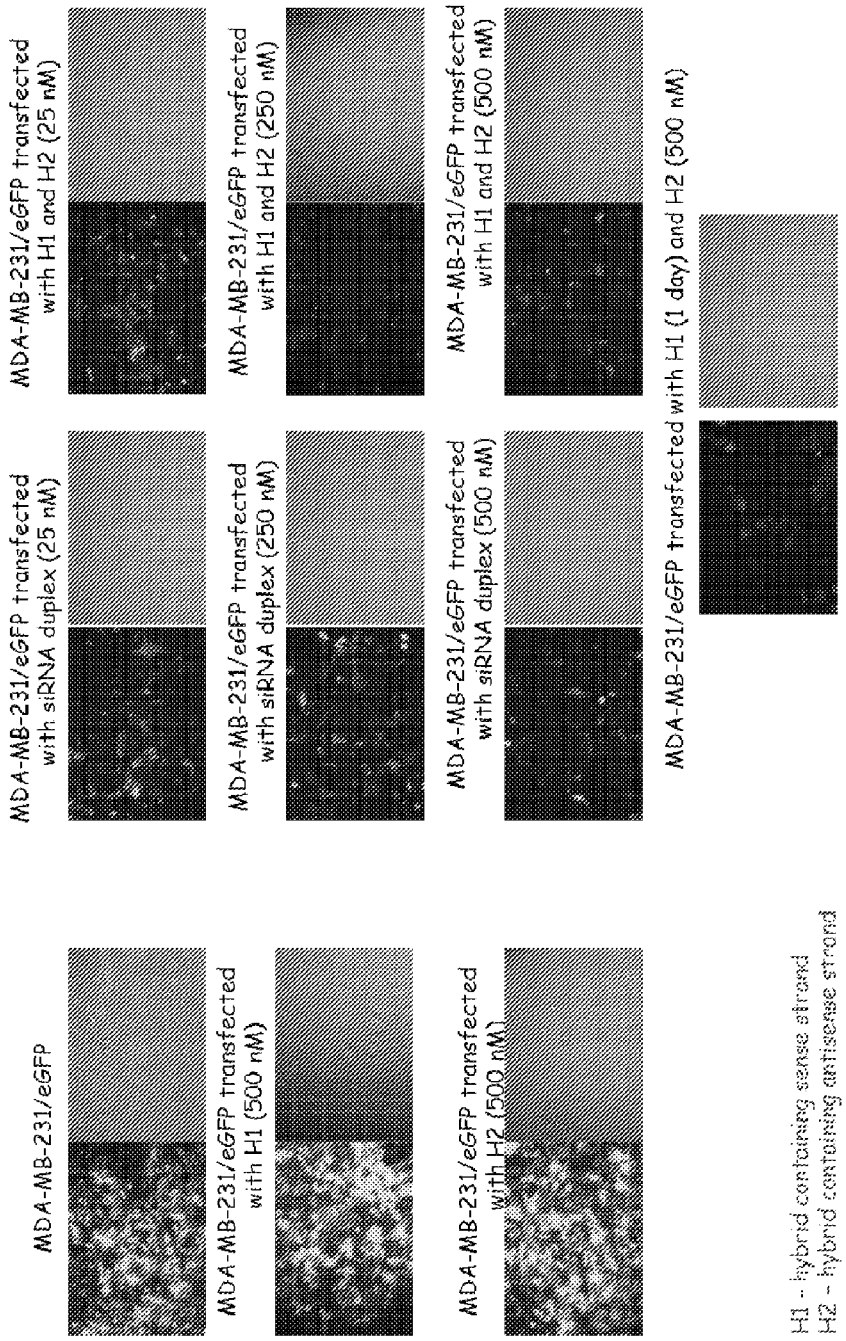
FIG. 21 shows that the self-recognizing particles are able to silence target gene expression at levels comparable to pre-formed siRNA duplexes.
Figure 22:
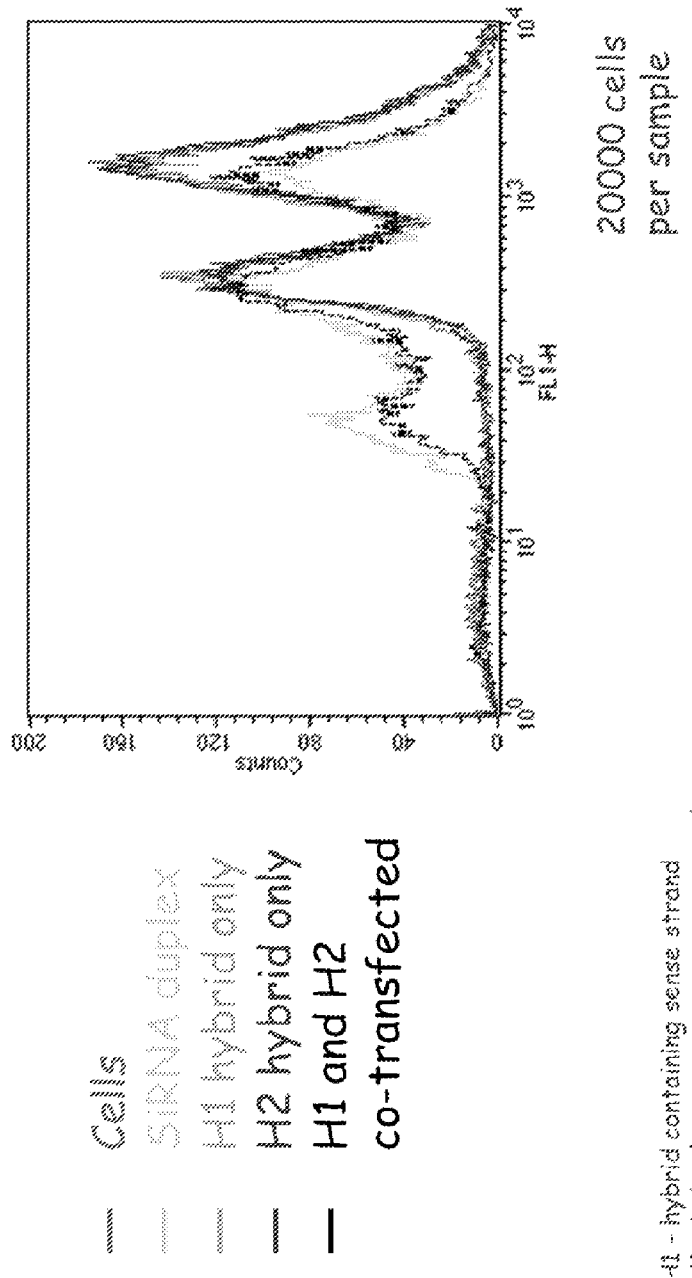
FIG. 22 shows that same day co-transfection of hybrids results in levels of target gene silencing comparable to those seen with pre-formed siRNA duplexes.
Figure 23:
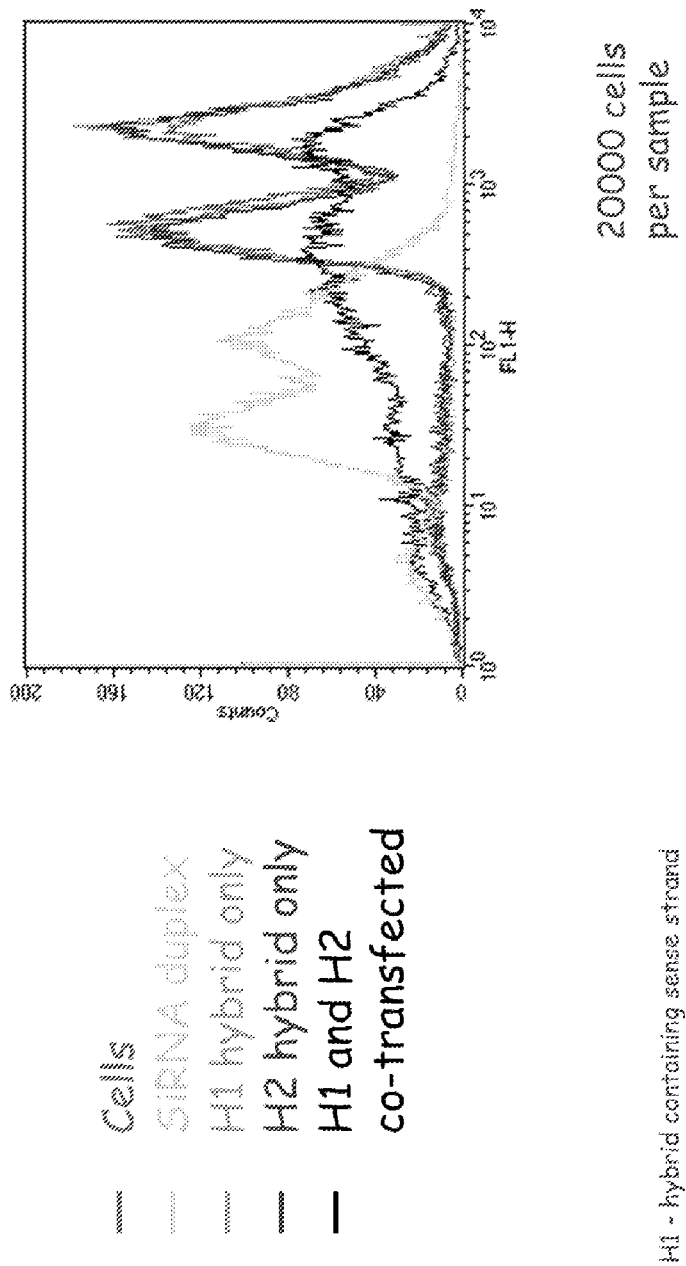
FIG. 23 is an example of the same day co-transfection of hybrids.
Figure 24:
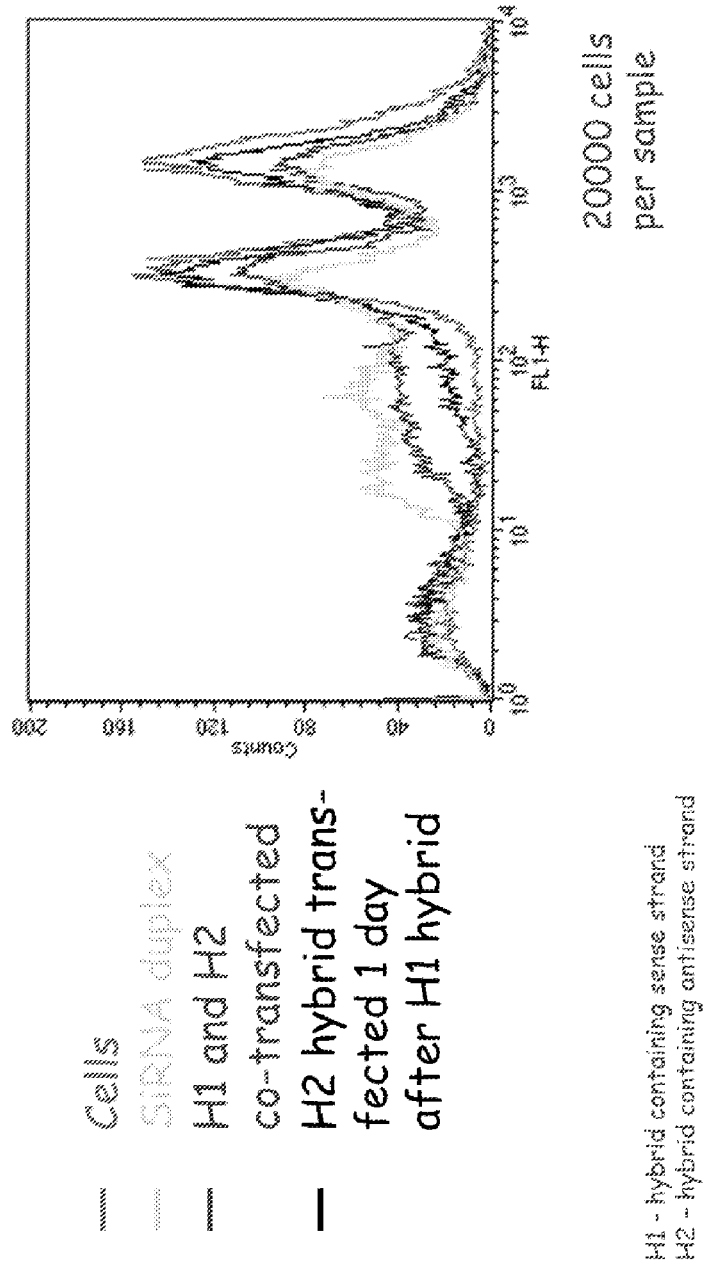
FIG. 24 shows that hybrid co-transfection on two different days results in target gene silencing.
Figure 25:
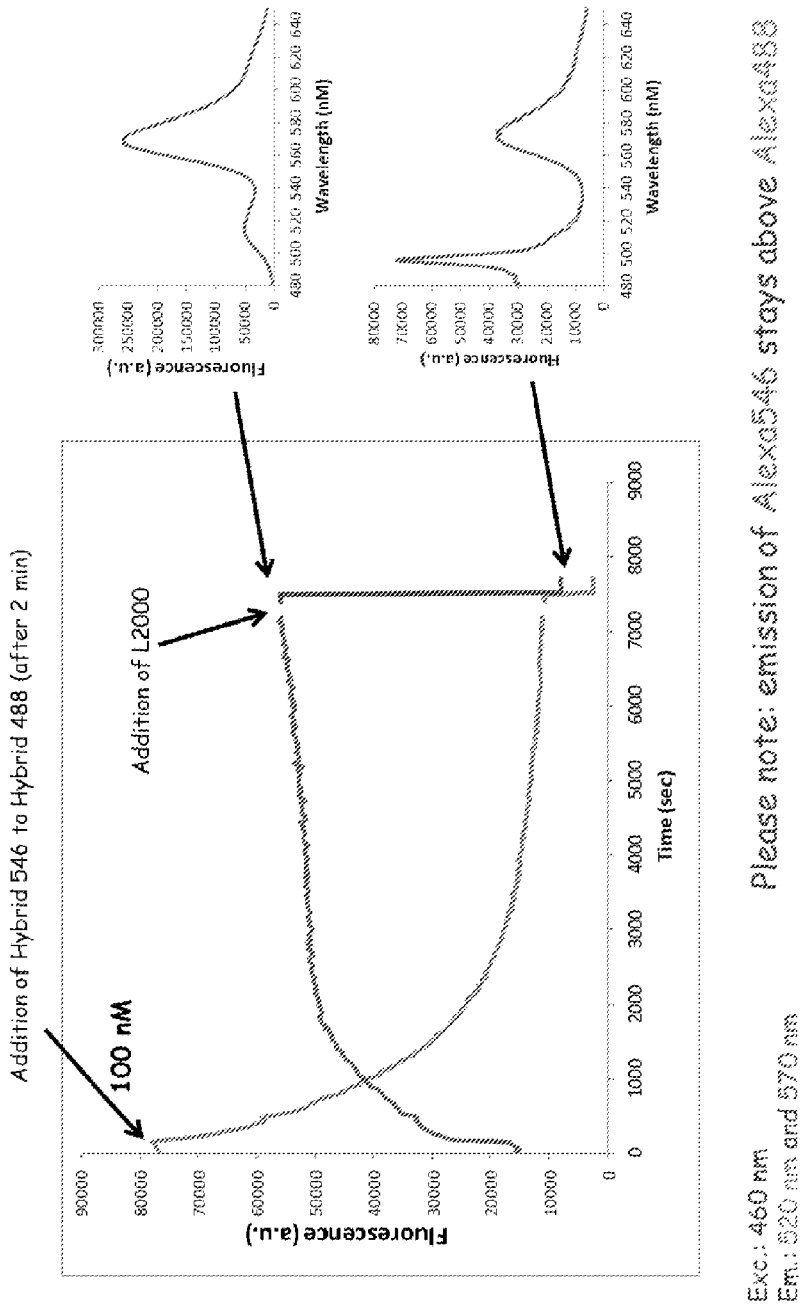
FIG. 25 shows that lipofectamine 2000 partially quenches fluorescence.
Figure 26:
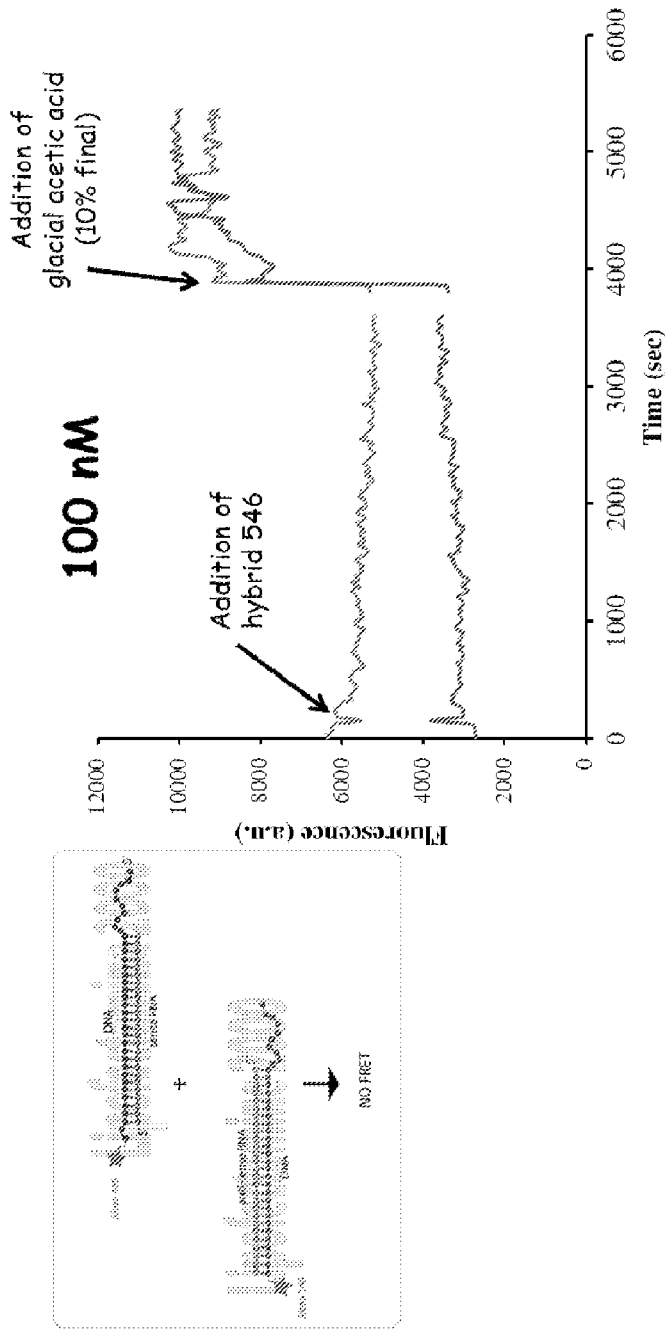
FIG. 26 shows that lipofectamine 2000 prevents hybrid recombination.
Figure 27:
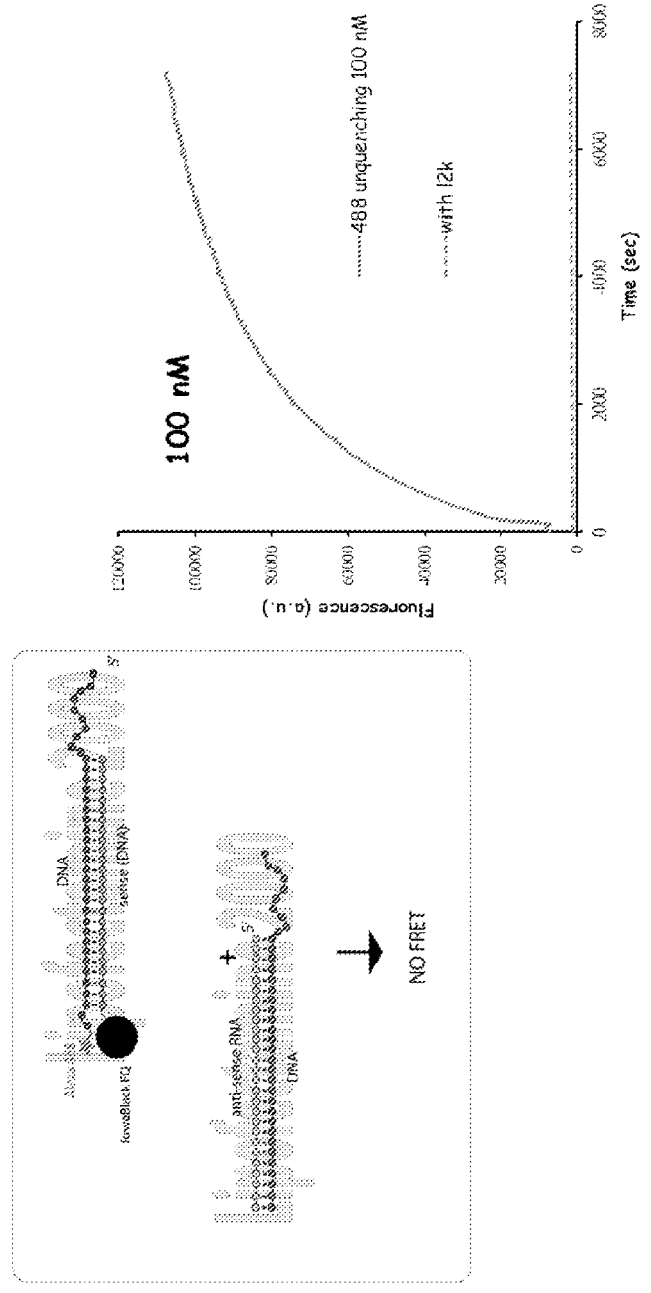
FIG. 27 shows that pre-formed lipofectamine 2000/hybrids exhibited no recombination.
Figure 28:
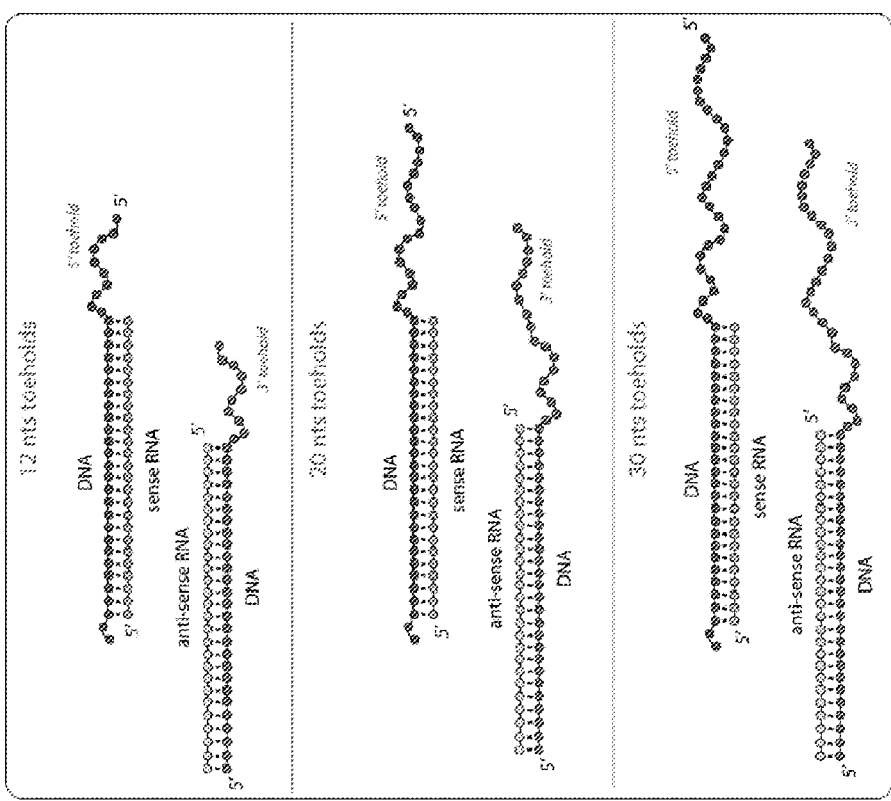
FIG. 28 is a schematic showing the design of hybrids with variable toehold lengths.
Figure 29:
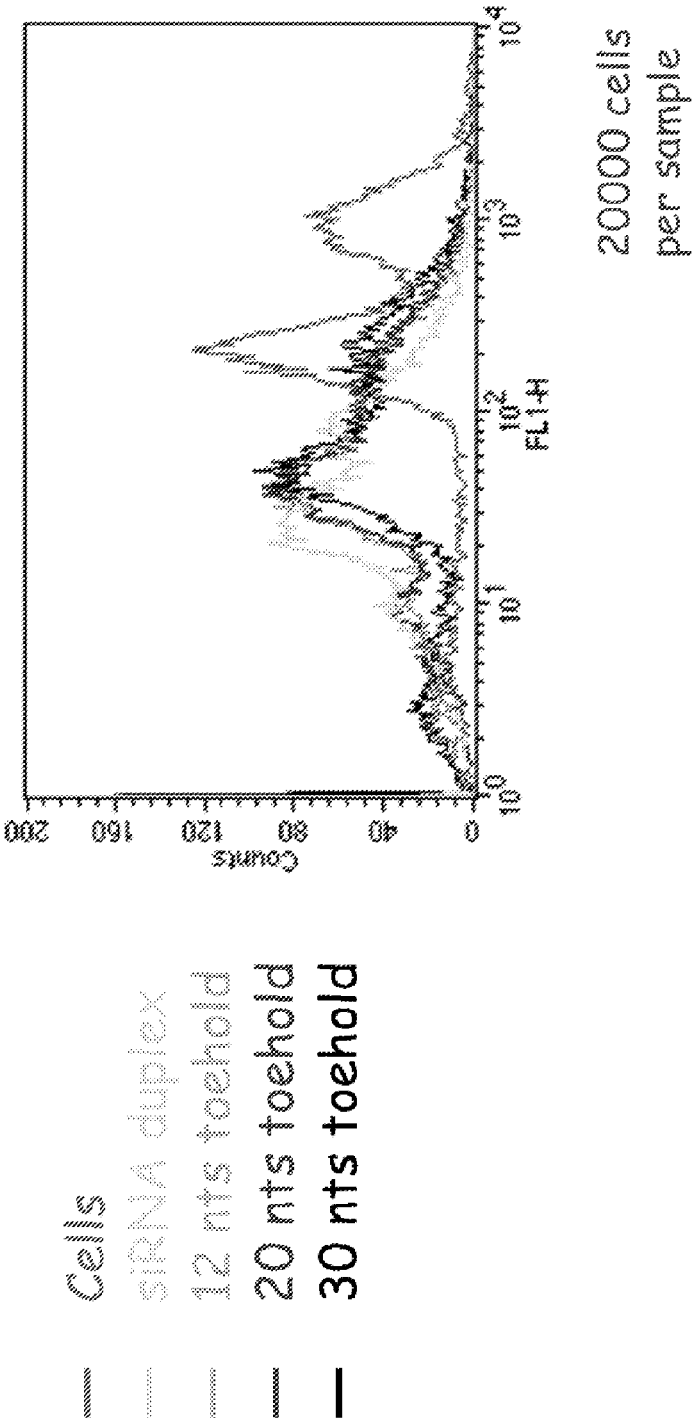
FIG. 29 shows the effects of variable toehold lengths on silencing in same day transfections.
Figure 30:
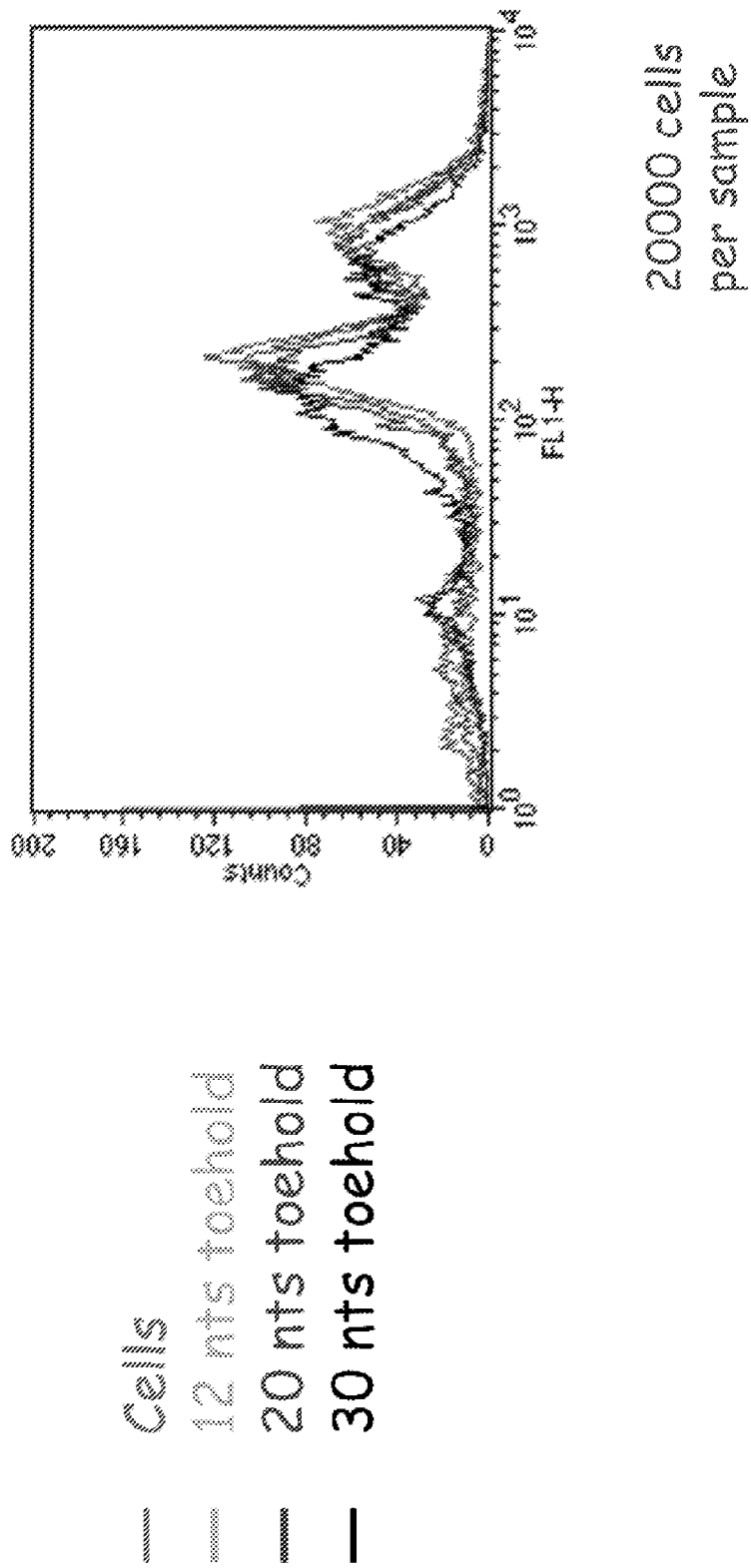
FIG. 30 shows the effects of variable toehold lengths on silencing in different day transfections.
Figure 31:
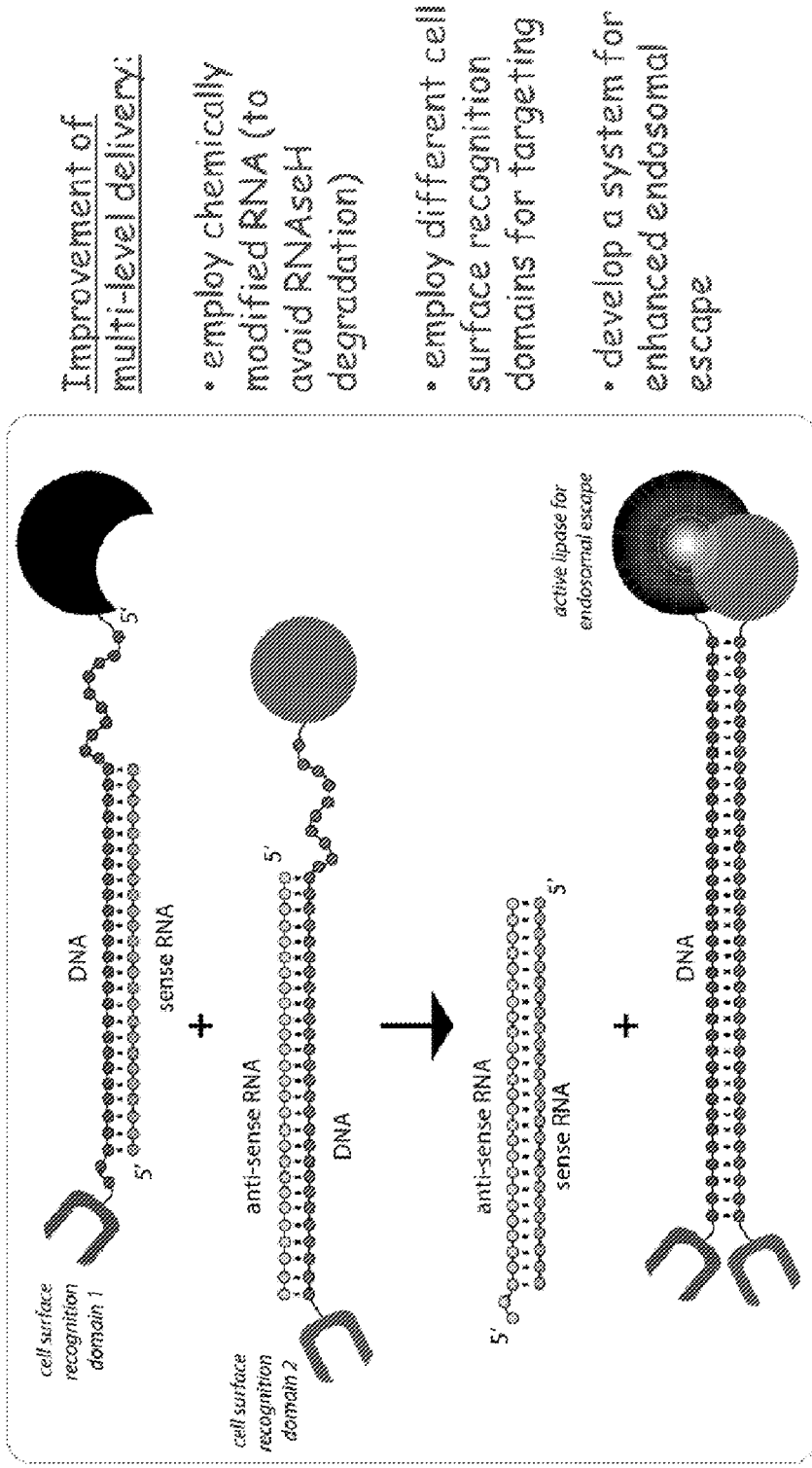
FIG. 31 shows the design of improved hybrids that increase multi-level delivery.

The RNAi pathway and the involvement of the Dicer enzymes are shown in FIGS. 1-3. The steps involved in the design of self-recognizing R/DNA hybrids are shown in FIGS. 4-6. The operation of self-recognizing R/DNA hybrids are shown in FIGS. 7-9. The in vitro formation of hybrid re-association and the affinities and kinetics of formation are shown in FIGS. 10-13. The formation of hybrids in vivo is shown in FIGS. 14 and 15. The re-association of R/DNA hybrids can be tracked, both in vitro and in vivo, by de-quenching (FRET) as shown in FIGS. 16-20. As shown in FIGS. 21-24 the R/DNA hybrids are able to silence target gene expression at levels comparable to pre-formed siRNA duplexes. Lipofectamine 2000 partially quenches fluorescence (FIG. 25) and prevents hybrid re-association (FIGS. 26 & 27). As shown in FIGS. 28-30 the toehold lengths can be altered with various effects on gene silencing. As shown in FIG. 31 R/DNA hybrids can be designed with chemically modified RNA, having different cell surface recognition domains, and moieties that improve endosomal escape.

Example 2

Rational Design of R/DNA Hybrids and Nomenclature

Figure 32:
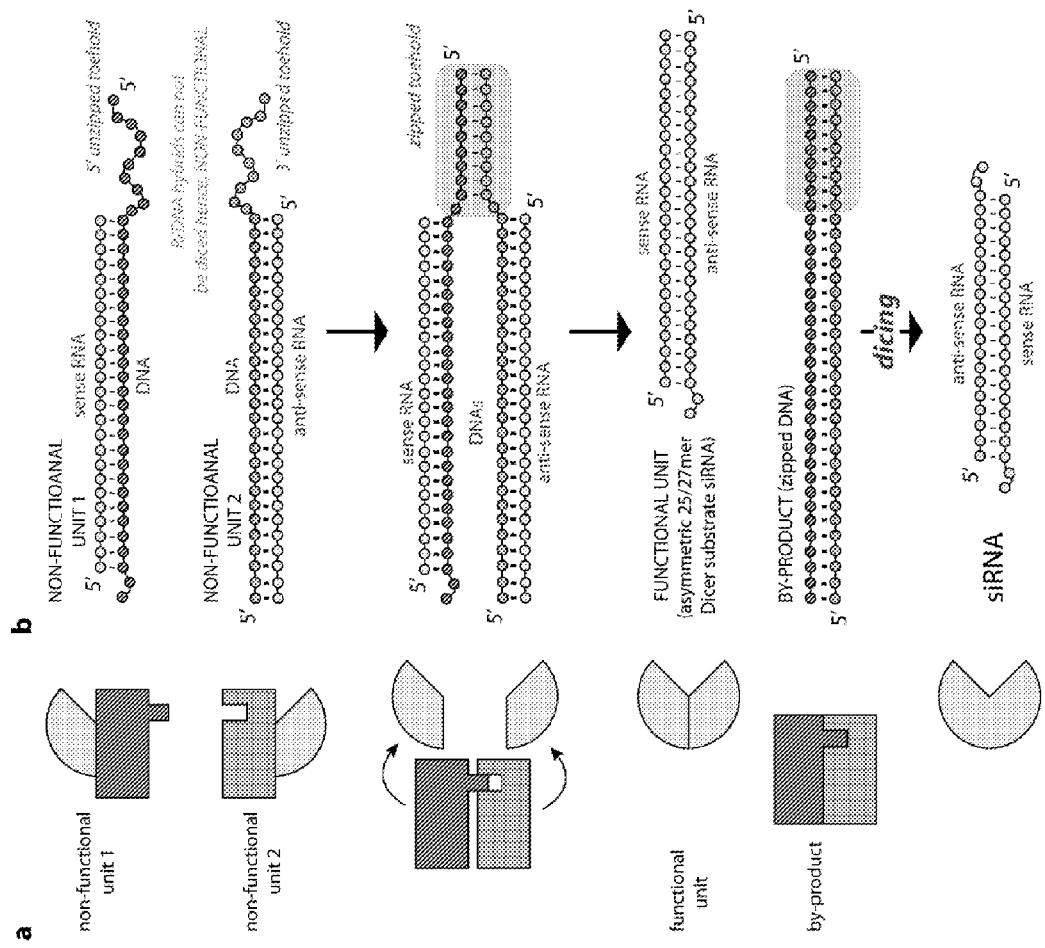
FIG. 32 shows the activation of functionality by two auto-recognizing R/DNA hybrids. (a) illustration showing a general principle of functionality activation upon re-association of two non-functional units. (b) Schematic representation of auto-recognizing R/DNA hybrid re-association resulting in asymmetric Dicer substrate siRNA release. The color code is kept the same throughout the figure.
Figure 33:
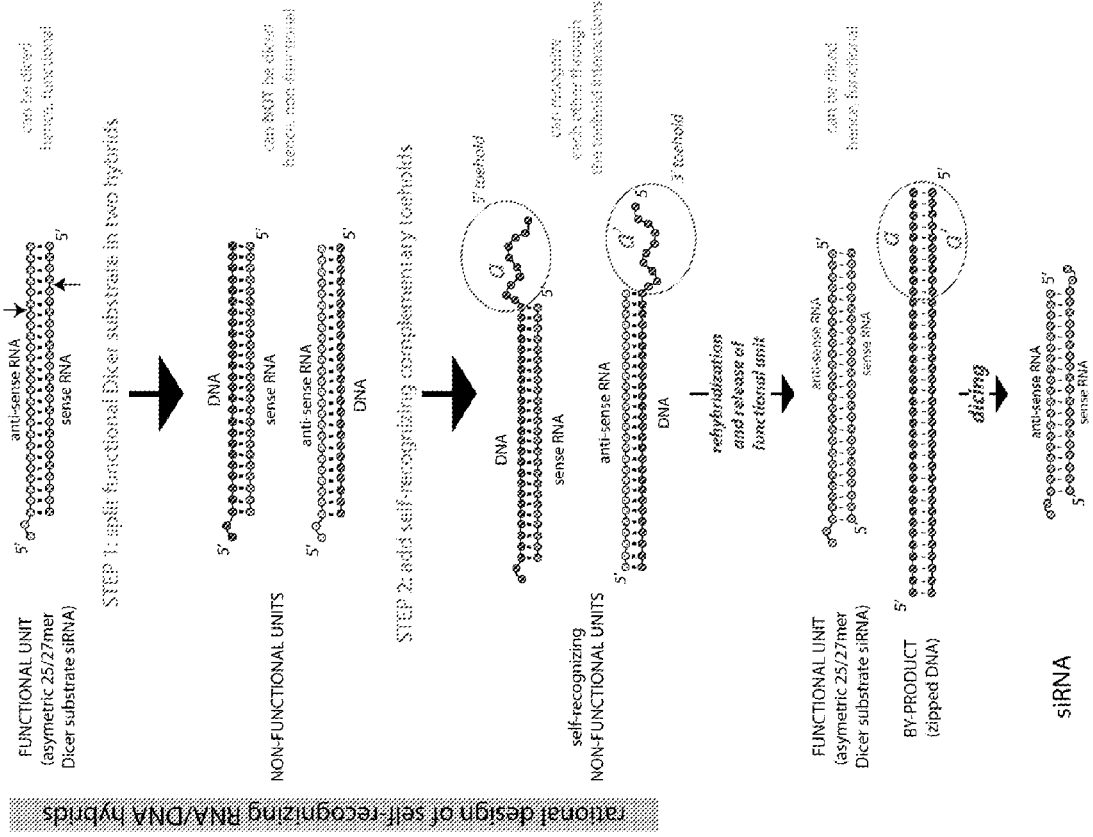
FIG. 33 is an illustration showing the rational design of RNA/DNA hybrids able to release the functionality (asymmetric 25/27mer Dicer substrate) upon re-association.

As a proof of principle, several pairs of R/DNA hybrids were designed which upon re-association release asymmetric Dicer substrates against enhanced green fluorescent protein (eGFP), HIV-1, or glutathione S-transferase P1 (GSTP1). The design rationale of R/DNA hybrids is the following (FIGS. 32 and 33): functional Dicer substrate siRNAs are split between two R/DNA hybrids preventing them from being diced and thus, making them non-functional (FIG. 33, step 1). Additionally, it has been shown that substitution of one or both siRNA strands with DNA completely eradicates RNAi. Next, each of the hybrid DNA strands is decorated with a complementary toehold required for hybrid re-association (FIG. 33, step 2) resulting in Dicer substrate siRNA release. All hybrids containing the sense strand are referred to as H_s and hybrids containing the antisense strand as H_ant. A partial set of sequences used are listed below.

RNA sequences
siRNA duplex:
Asymmetric 25/27mer Dicer substrate siRNA duplex
designed against eGFP
sense
5'-pACCCUGAAGUUCAUCUGCACCACCG (SEQ ID NO: 2)

antisense
5'-CGGUGGUGCAGAUGAACUUCAGGGUCA (SEQ ID NO: 3)

Nicked sense strand for siRNA:
Nicked sense strand for asymmetric 25/27mer
Dicer substrate siRNA duplex designed
against eGFP
1/2 Sense 1
5'-pACCCUGAAGUUC (SEQ ID NO: 4)

1/2 sense 2
5'-AUCUGCACCACCG (SEQ ID NO: 5)

5' sides of sense and 1/2 Sense_12 nt strands are
phosphorylated.
siRNA duplex designed against eGFP
sense
5'-pACCCUGAAGUUCAUCUGCACC (SEQ ID NO: 6)

antisense
5'-UGCAGAUGAACUUCAGGGUCA (SEQ ID NO: 7)

Asymmetric Dicer substrate siRNA duplexes
designed against HIV-1
Protease (Pro). Positions 2332 to 2356,
according to pNL4-3.
sense
5'-pGAGCAGAUGAUACAGUAUUAGAAGA (SEQ ID NO: 8)

antisense
5'-UCUUCUAAUACUGUAUCAUCUGCUCCU (SEQ ID NO: 9)

Envelope (Env). gp120, Positions 7642 to 7665,
according to pNL4-3.
sense
5'-GGACAAUUGGAGAAGUGAAUUAUAUU (SEQ ID NO: 10)

antisense
5'-pUAUAAUUCACUUCUCCAAUUGUCC (SEQ ID NO: 11)

Asymmetric Dicer substrate siRNA duplexes
designed against GSTP1-1
sense
5'-pAAGGAUGACUAUGUGAAGGCACUGC (SEQ ID NO: 12)

antsense
5'-GCAGUGCCUUCACAUAGUCAUCCUUGC (SEQ ID NO: 13)

DNA sequences
Unzipped toeholds are underlined and their
lengths (nt) are represented by the numbers
next to the names
Hybrids designed against eGFP
DNA for sense_12
5'-<u>GGAGACCGTGAC</u>CGGTGGTGCAGATGAACTTCAGGGTCA
(SEQ ID NO: 14)

DNA for antisense_12
5'-TGACCCTGAAGTTCATCTGCACCACCG<u>GTCACGGTCTCC</u>
(SEQ ID NO: 15)

DNA for sense_20
5'-<u>GGAGACCGTGACAGTGATTA</u>CGGTGGTGCAGATGAAC

TTCAGGGTCA (SEQ ID NO: 16)

DNA for antisense_20
5'-TGACCCTGAAGTTCATCTGCACCACCG<u>TAATCACTGT

CACGGTCTCC</u> (SEQ ID NO: 17)

DNA for sense_30
5'-<u>GGAGACCGTGACAGTGATTAGATTACACT</u>CCGGTGGTGCAG

ATGAACTTCAGGGTCA (SEQ ID NO: 18)

DNA for antisense_30
5'-TGACCCTGAAGTTCATCTGCACCACCG<u>GAGTGTAATCTAAT

CACTGTCACGGTCTCC</u> (SEQ ID NO: 19)

Hybrids designed against HIV-1
Protease (Pro)
DNA for sense_12
5'-AGUCUUCUAAUACUGUAUCAUCUGCUCCU<u>GTCACGGTCTCC</u>
(SEQ ID NO: 20)

DNA for antisense_12
5'-<u>GGAGACCGTGAC</u>GAGCAGAUGAUACAGUAUUAGAAGA
(SEQ ID NO: 21)

Envelope (Env)
DNA for sense_12
5'-AATATAATTCACTTCTCCAATTGTCC<u>GTCACGGTCTCC</u>
(SEQ ID NO: 22)

DNA for antisense_12
5'-<u>GGAGACCGTGAC</u>GGACAATTGGAGAAGTGAATTATATT
(SEQ ID NO: 23)

5'-<u>GGAGACCGTGAC</u>TGGAGGAAATGAACAAGTAGATAAAT
(SEQ ID NO: 24)

Hybrids designed against GSTP1-1
DNA for sense
5'-GCAGTGCCTTCACATAGTCATCCTTGC<u>GTCACGGTCTCC</u>
(SEQ ID NO: 25)

DNA for antisense
5'-<u>GGAGACCGTGAC</u>GCAAGGATGACTATGTGAAGGCACTGC
(SEQ ID NO: 26)

Fluorescently labeled RNA sequences
Sense strand of siRNA duplex designed against
eGFP[1]
RNA sense_IRDye700
5'-/5IRD700/ACCCUGAAGUUCAUCUGCACCACCG
(SEQ ID NO: 27)

Fluorescently labeled DNA sequences
DNA for sense_12_Alexa488
5'-<u>GGAGACCGTGAC</u>CGGTGGTGCAGATGAACTTCAGGGTCAtt/3AI
exF488N/ (SEQ ID NO: 28)

DNA for antisense_12_Alexa546
5'-/5AI
exF546N/aaTGACCCTGAAGTTCATCTGCACCACCG<u>GTCACGGTCTCC</u>
(SEQ ID NO: 29)

Truncated DNA for antisense_12_Alexa546
5'-/5AI exF546N/aaTGACCCTGAAGTTCATCTGCACCACCG
(SEQ ID NO: 30)

DNA sense_Iowa Black FQ
5'-/5IAbFQ/ACCCTGAAGTTCATCTGCACCACCG
(SEQ ID NO: 31)

Figure 34:
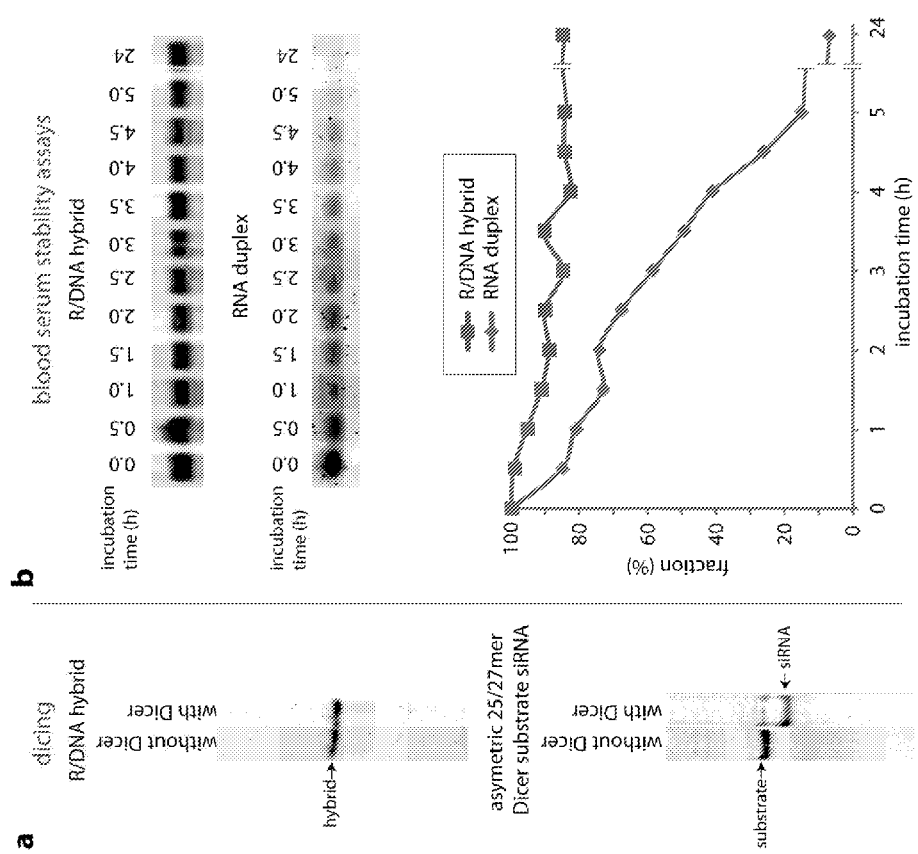
FIG. 34 shows the comparative analysis of R/DNA hybrids and RNA duplexes. (a) Total SYBR Gold staining native PAGE results for dicing experiments carried out for R/DNA hybrid and asymmetric 25/27mer Dicer substrate siRNA duplex respectively with recombinant human turbo dicer enzyme kit (Genlantis). (b) Total ethidium bromide staining agarose gel and quantification results representing the relative stabilities of R/DNA hybrid and asymmetric 25/27mer Dicer substrate siRNA duplex respectively in 80% human blood serum.

A scheme of re-association for the hybrids is shown in FIG. 34. The complementary single-stranded unzipped toeholds in R/DNA hybrids are designed using Mfold (Zuker, M, *Nucleic Acids Res* 31, 3406-3415 (2003)) to avoid any stable secondary structures. In order to exceed a melting temperature ($T_m$) of 37° C., the minimal length of the unzipped toeholds with GC content≥60% should be at least 12 nucleotides (nts). The $T_m$ for designed single stranded toeholds is estimated to be ~40° C. using the Wallace rule (Wallace, R. B. et al., *Nucleic Acids Res* 6, 3543-3557 (1979)). Toeholds of 20 nts and 30 nts were also tested. All H_s hybrids have two base 3'-overhangs due to the asymmetry of siRNA duplexes (FIG. 34). The relative thermodynamic stabilities for DNA, R/DNA and RNA duplexes can be ordered with the highest for RNA and the lowest for DNA duplexes respectively (Sugimoto, N. et al., *Biochemistry* 34, 11211-11216 (1995)). Using nucleic acid package NUPACK (Zadeh, J. N. et al., *J Comput Chem* 32, 170-173 (2011)), free energies of dimerization for RNA and DNA duplexes were calculated at 37° C. and equimolar (1 µM) concentrations of individual strands. Currently, there are no publically available computational methods for R/DNA hybrid free energy calculations. Therefore, to estimate ΔGs of designed R/DNA hybrids, we used the following approximated equation:

$$\Delta G(\text{R/DNA hybrid}) \sim (\Delta G(\text{DNA "hybrid" duplex}) + \Delta G(\text{RNA "hybrid" duplex}))/2 \quad \text{(Eq. 1)}$$

where ΔG(DNA "hybrid" duplex) is the free energy calculated for a DNA duplex having sequences identical to the corresponding R/DNA hybrid and ΔG(RNA "hybrid" duplex) is the free energy of an RNA duplex with sequences identical to the same hybrid.

Free energy of the initial state was calculated:

$$\Delta G_{initial} \sim \Delta G(\text{R/DNA hybrid 1}) + \Delta G(\text{R/DNA hybrid 2}) \quad \text{(Eq. 2)}$$

Free energy of the final state was calculated:

$$\Delta G_{final} = \Delta G(\text{final RNA duplex}) + \Delta G(\text{final DNA duplex}) \quad \text{(Eq. 3)}$$

The difference in free energies between final and initial states was calculated $$\Delta\Delta G \sim \Delta G_{final} - \Delta G_{initial} \quad \text{(Eq. 4)}$$

Therefore, the driving force for re-association after toehold zipping is the difference in free energies (ΔΔG~−19.5 kcal/mol, Eq. 4, above) between the initial (R/DNA hybrids (25 and 27 bps) with ΔG~−85.4 kcal/mol, Eq. 2, above) and the final (siRNA (25 bp) and DNA duplex (39 bps) with ΔG~104.9 kcal/mol, Eq. 3, above) states. Free energies of dimerization for RNA and DNA duplexes were calculated using NUPACK (Zadeh, J. N. et al., *J Comput Chem* 32, 170-173 (2011)).

Example 3

Dicing Assays and Resistance to Ribonuclease Degradation in Human Serum

Engineered R/DNA hybrids and siRNA duplexes were prepared and tested for their ability to be processed by human recombinant Dicer as described previously (Afonin, K. A. et al., *Nat Protoc* 6, 2022-2034 (2011) & Grabow, W. W. et al., *Nano Lett* 11, 878-887 (2011)). Native gel shift assays presented in FIG. 34 confirmed previously published observations (Zhang, H. et al., *The EMBO journal* 21, 5875-5885 (2002)) that human enzyme Dicer is inactive against individual R/DNA hybrids but will cleave the RNA duplexes. Thus, preliminary dicing results support the idea that only recombined R/DNA hybrids that separately enter the cells will be processed by Dicer and further loaded to RISC which in turn will activate the RNAi.

It is known that in a biological context, naked siRNAs can be rapidly degraded by nucleases and therefore, to increase the retention time of the functional siRNAs in the blood stream, chemically modified dNMPs are often introduced (Guo, P., *Nat Nanotechnol* 5, 833-842 (2010)). However, RNA/DNA hybrids were reported to be well protected in the blood serum (Hoerter, J. A. et al., *PloS one* 6, e20359 (2011)). The relative stabilities measured for auto-recognizing R/DNA hybrids and their corresponding siRNA duplexes strongly confirmed previous observations FIG. 34.

Example 4

Studies of R/DNA Hybrid Re-Association In Vitro Using FRET

Figure 35:
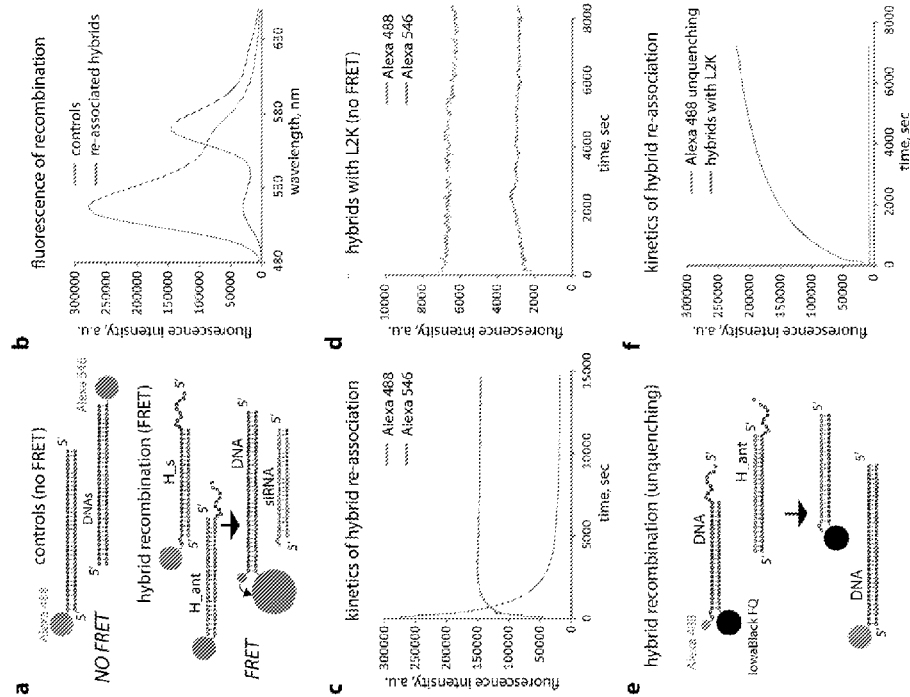
FIG. 35 shows fluorescent studies of auto-recognizing R/DNA hybrid re-association in solution at 37° C. (a) Schematic representations of control DNA duplexes fluorescently labeled with Alexa488 and Alexa546 unable to recombine (upper part) and fluorescently labeled auto-recognizing R/DNA hybrids programmed for re-association (lower part). (b) Emission spectra of control DNA duplexes showing no FRET and recombined auto-recognizing R/DNA hybrids with increased Alexa546 emission signal. (c) FRET time traces during re-association of auto-recognizing R/DNA hybrids labeled with Alexa488 and Alexa546. (d) Fluorescently labeled R/DNA hybrids individually associated with L2K prior to mixing were followed by fluorescent time tracing. Please note that L2K forms complexes with hybrids thus, preventing their re-association and the emission signal of Alexa488 (in green) stays above Alexa546 (in red) comparing to (c). (e-f) Schematic representations and FRET time traces during re-association of auto-recognizing R/DNA hybrids labeled with Alexa488 and quencher IowaBlack FQ (in green) with schematic representation of corresponding hybrids programmed for recombination. Please note that as well as in (d), L2K forms complexes with quenched hybrids (in blue) and prevents their recombination.
Figure 36:
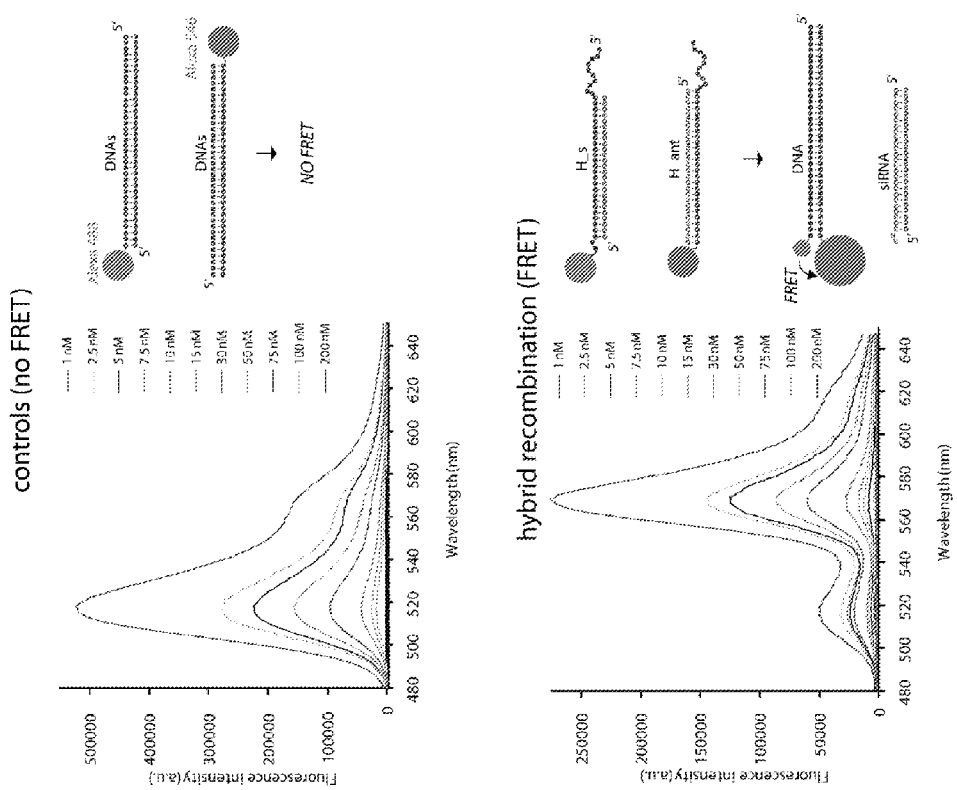
FIG. 36 shows fluorescent studies of auto-recognizing R/DNA hybrid re-association in solution after 3 hour incubation at 37° C. Emission spectra and schematic representations of (upper panel) control DNA duplexes fluorescently labeled with Alexa488 and Alexa546 unable to recombine and (lower panel) emissions of fluorescently labeled auto-recognizing R/DNA hybrids programmed for re-association. Please note an increase in Alexa546 emission signals. For all samples at different concentrations (as indicated in nM), the excitation was at 460 nm.
Figure 37:
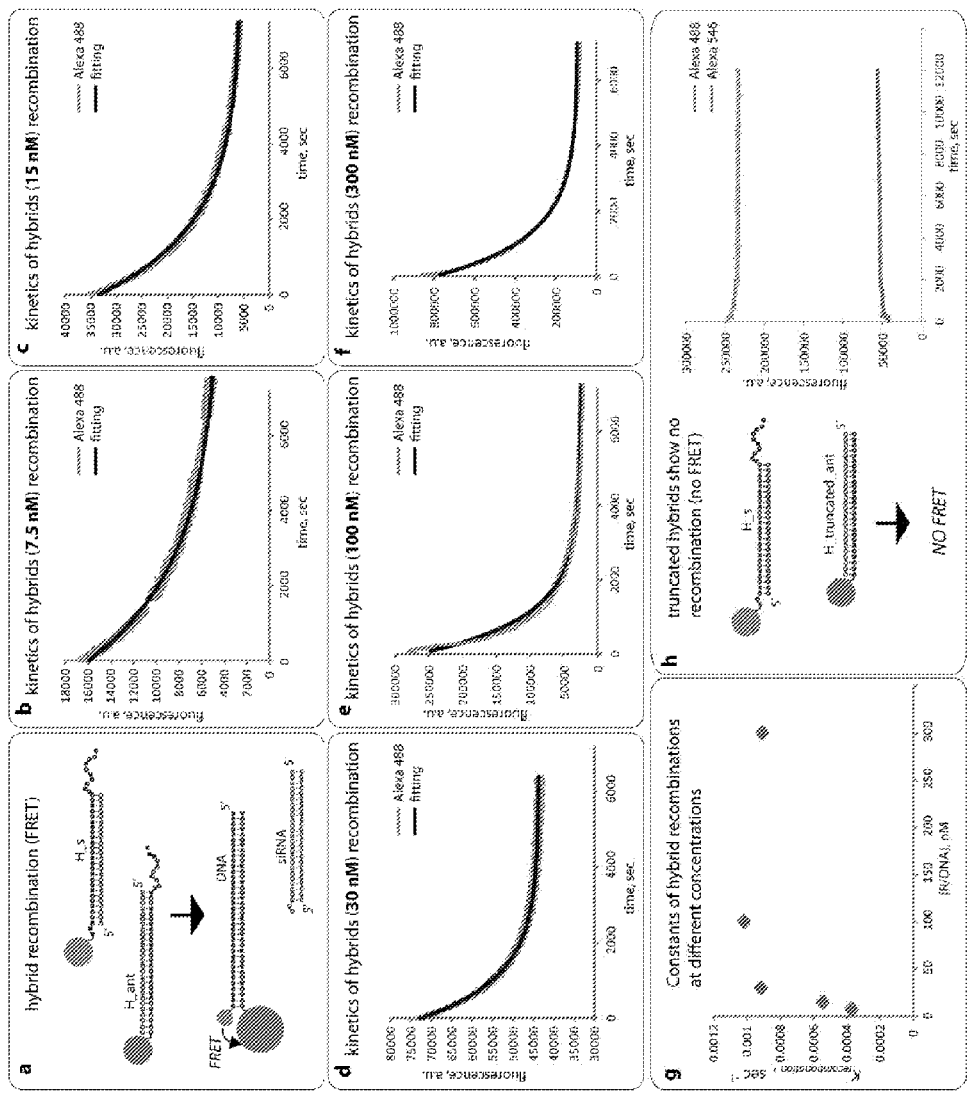
FIGS. 37A-37E are schematics and graphs showing the kinetics of auto-recognizing R/DNA hybrid re-association at 37° C. (a) Schematic representation of re-association and (b-f) FRET time traces and their fittings during re-association of auto-recognizing R/DNA hybrids labeled with Alexa488 and Alexa546 which were mixed at different equimolar concentrations specified above for each case and incubated at 37° C. For all samples, excitation was set at 460 nm and emission was measured at 520 nm every 1 second for b-d and every 30 seconds for e and f. (g) Constants of auto-recognizing R/DNA hybrid re-association (derived from b-f fittings) depend on the concentrations of hybrids at lower concentrations (below ~30 nM). (h) Schematic representation of truncated hybrid without toehold and corresponding FRET time traces. Please note that there are no significant changes in the fluorescence signals suggesting that the toeholds are essential for re-association.

To introduce the additional functionality of imaging the triggered response to delivery and re-association of R/DNA hybrids in cells and to study their interactions in vitro, the 3'-side of antisense and the 5'-side of sense binding DNAs were fluorescently tagged with Alexa488 and Alexa546 respectively (FIG. 35A). These dyes are commonly used in Förster resonance energy transfer (FRET) studies (Berney, C. & Danuser, G., *Biophysical journal* 84, 3992-4010 (2003)). When two fluorescently labeled R/DNA hybrids are mixed and incubated at 37° C., their re-association places Alexa488 within the Förster distance ($R_0$=6.31 nm) of Alexa546. As a result, when excited at 460 nm, the emission of Alexa546 tremendously increases and the signal of Alexa488 drops compared to a control system of the premade fluorescently labeled DNA duplexes unable to recombine (FIGS. 35B and 36). Titration experiments for different concentrations were carried out to determine the lowest sensitivity concentration (~5 nM) of cognate R/DNA duplexes at which FRET can be recorded (FIG. 36).

The kinetics of re-association were also studied using the same FRET based system. In these experiments, R/DNA hybrids labeled with Alexa488 were incubated at 37° C. for two minutes followed by the addition of hybrids tagged with Alexa546. The process of re-association through FRET measurements was tracked every 30 seconds (FIG. 35C). The experiments were repeated at several different concentrations of cognate R/DNA hybrids (FIGS. 37A-37F).

The reaction of re-association for auto-recognizing R/DNA hybrids consists of two steps and can be represented by the following equation:

where R and D stand for single-stranded RNA and DNA. The first step ($k_1$) is the auto-recognition of the R/DNA hybrids through the zipping of the toeholds leading to the formation of a tetramer. The second step ($k_2$) is the rehybridization which yields RNA and DNA duplexes.

Kinetics of Recombination

The reaction taking place during the re-association process can be described as follows:

Or more simply

The decay of the different products can then be described as follows:

$$\frac{d[A]}{dt} = -k_1[A]$$

-continued $$\frac{d[B]}{dt} = k_1[A] - k_2[B]$$

$$\frac{d[C]}{dt} = -k_2[B]$$

Provided the two kinetic constants are different, the integration of the differential equations yields the following rate equations:

$$[A] = [A]_0 e^{-k_1 t}$$

$$[B] = [A]_0 \frac{k_1}{k_2 - k_1}(e^{-k_1 t} - e^{-k_2 t}) + [B]_0 e^{-k_2 t}$$

$$[C] = [A]_0 \left(1 + \frac{k_1 e^{-k_2 t} - k_2 e^{-k_1 t}}{k_2 - k_1}\right) + [B]_0 (1 - e^{-k_2 t}) + [C]_0$$

Initially, since no re-association has taken place, $[B]_0=0$ and $[C]_0=0$ and the equation simplifies as follows:

$$[C] = [A]_0 \left(1 + \frac{k_1 e^{-k_2 t} - k_2 e^{-k_2 t}}{k_2 - k_1}\right)$$

Since the first reaction between the two hybrids is of second order, $k_1$ is proportional to $[A]_0$, the initial concentration. For the case of very high initial concentrations, $[A]_0$, $k_2 \ll k_1$ and the appearance of the product producing FRET, C, can be modeled with the following exponential decay:

$$[C] = [A]_0 (1 - e^{-k_2 t})$$

for which the rate constant $k_2$ is not concentration dependent.

For the case of very low initial concentrations $[A]_0$, $k_2 \gg k_1$ and the appearance of the product producing FRET, C, can be modeled with the following exponential decay:

$$[C] = [A]_0 (1 - e^{-k_1 t})$$

for which the rate constant $k_1$ depends on the initial hybrid concentration $[A]_0$.

The mathematical model predicts that for high initial concentrations of hybrids the second step is rate limiting and that this rate is concentration independent while for low initial concentrations of hybrids the first step becomes rate determining and that the rate is concentration dependent. According to that model, we could fit the data at the different concentrations with a single exponential decay (FIG. 37) and show that at concentrations lower than ~30 nM the limiting step of re-association is the zipping of the toeholds, while at higher concentrations, the rehybridization becomes the rate determining step.

To emphasize the importance of toehold interactions in the process of re-association and siRNA release, a hybrid without a toehold was tested for its ability to recombine (FIG. 37H). In this experiment, H_s hybrid labeled with Alexa488 was mixed with the truncated hybrid H_ant_truncated labeled with Alexa546 and their interactions were tracked through FRET measurements as described above. The results indicate no significant interactions within 3 hours of incubation at 37° C., thus providing evidence for the crucial role of toehold zipping in the re-association process.

Figure 38:
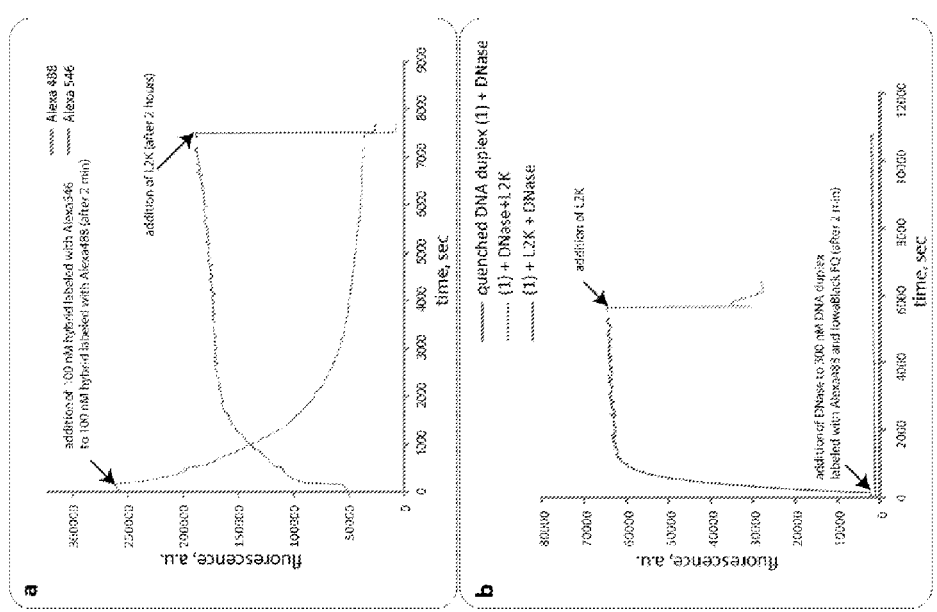
FIG. 38 shows that the Addition of lipofectamine2000 (L2K) quenches the fluorescence of recombined R/DNA hybrids in solution and protects duplexes from enzymatic degradation. (a) R/DNA hybrids labeled with Alexa488 and Alexa546 were mixed at 100 nM concentrations and L2K was added after two hours of incubation at 37° C. Excitation was set at 460 nm and emission was measured at 520 nm and 570 nm. Please note that the emission signal of Alexa546 stays above Alexa488. (b) Quenched DNA duplex labeled with Alexa488 and IowaBlack FQ was mixed at 300 nM concentrations with L2K and DNase was added after two minutes of incubation at 37° C. (blue line). No degradation was observed after three hours of incubation. As the control, the same duplex without L2K was completely digested by DNase (red line). L2K was then added upon digestion to assess its' own quenching potential on the digested duplex thereby providing a reference for the signal expected if digestion was to take place with L2K complexed duplexes. Excitation was set at 460 nm and emission was measured at 520 nm.

To mimic the transfection conditions in vitro, fluorescently labeled hybrids were separately pre-incubated with Lipofectamine2000 (L2K), a polycationic carrier used in this work for all transfection experiments, and then the kinetics of re-association were tracked (FIG. 35D). Results demonstrated no re-association between auto-recognizing R/DNA hybrids associated with the L2K in solution. Interestingly, the addition of L2K causes a ~10-fold drop in the fluorescence signals for Alexa488 and 546 (FIG. 38A). Additionally, L2K provides good protection (less than ~4% degradation) for duplexes against enzymatic activity (FIG. 38B).

Figure 39:
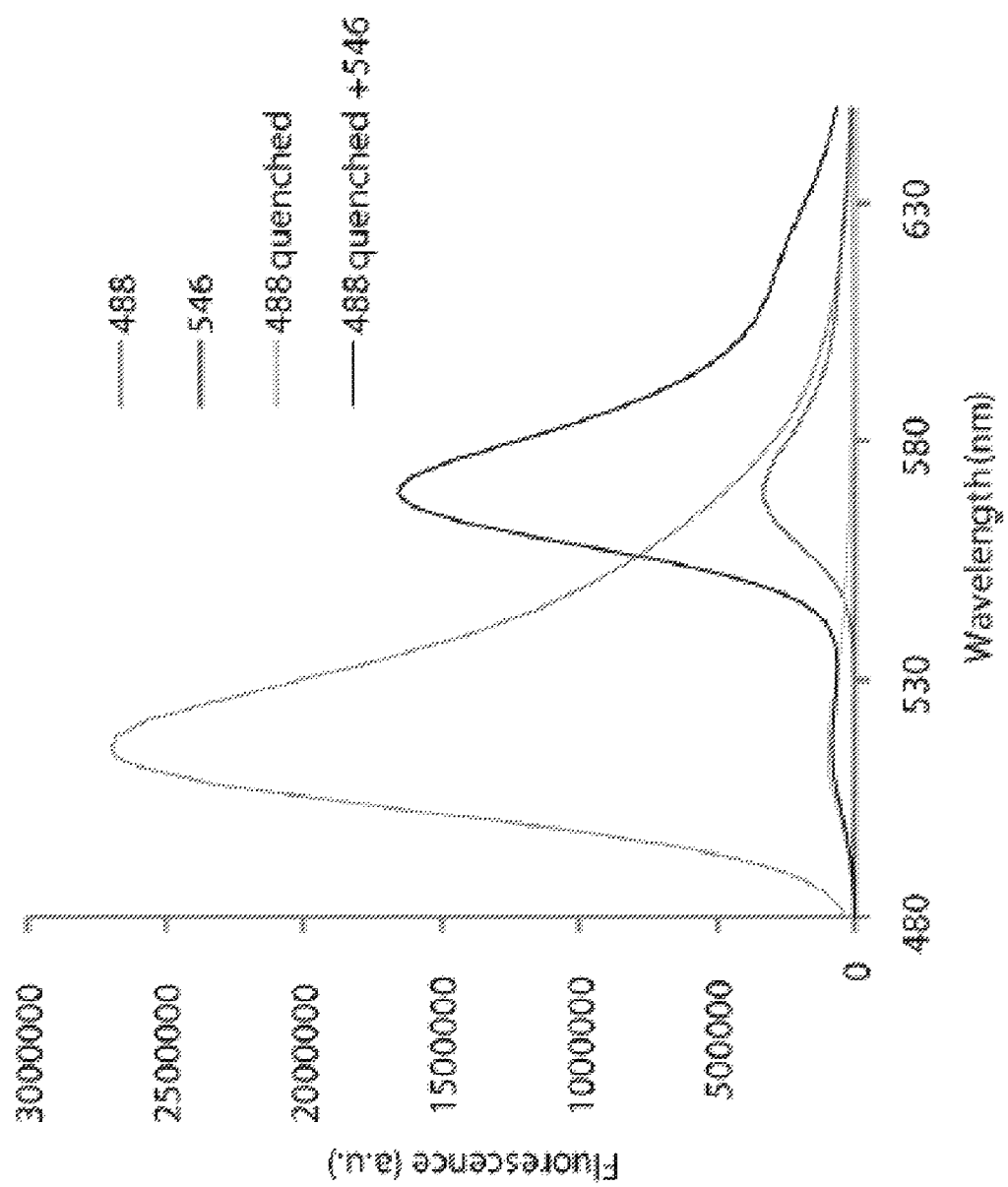
FIG. 39 shows fluorescent studies of auto-recognizing R/DNA hybrid re-association in solution after 3 hour incubation at 37° C. For all samples, excitation was set at 460 nm and a 100 nM concentration was used. The emission spectra were collected for an R/DNA hybrid labeled with Alexa488 (green curve) or Alexa546 (red curve), a duplex containing Alexa488 and the quencher IowaBlack FQ (yellow curve) and for the mixture of a duplex Alexa488/IowaBlack FQ with its cognate R/DNA Alexa546 hybrid (black).

As an alternative way to track the recombination, another FRET system based on an auto-recognizing duplex having Alexa488 quenched by the IowaBlack fluorescence quencher was used (FIG. 39). In this case, re-association separates the quencher from Alexa488 restoring its emission. Consistent with previous findings, experiments with L2K showed no recombination.

Example 5

R/DNA Hybrid Re-Association in Cells Monitored Using FRET

Figure 40:
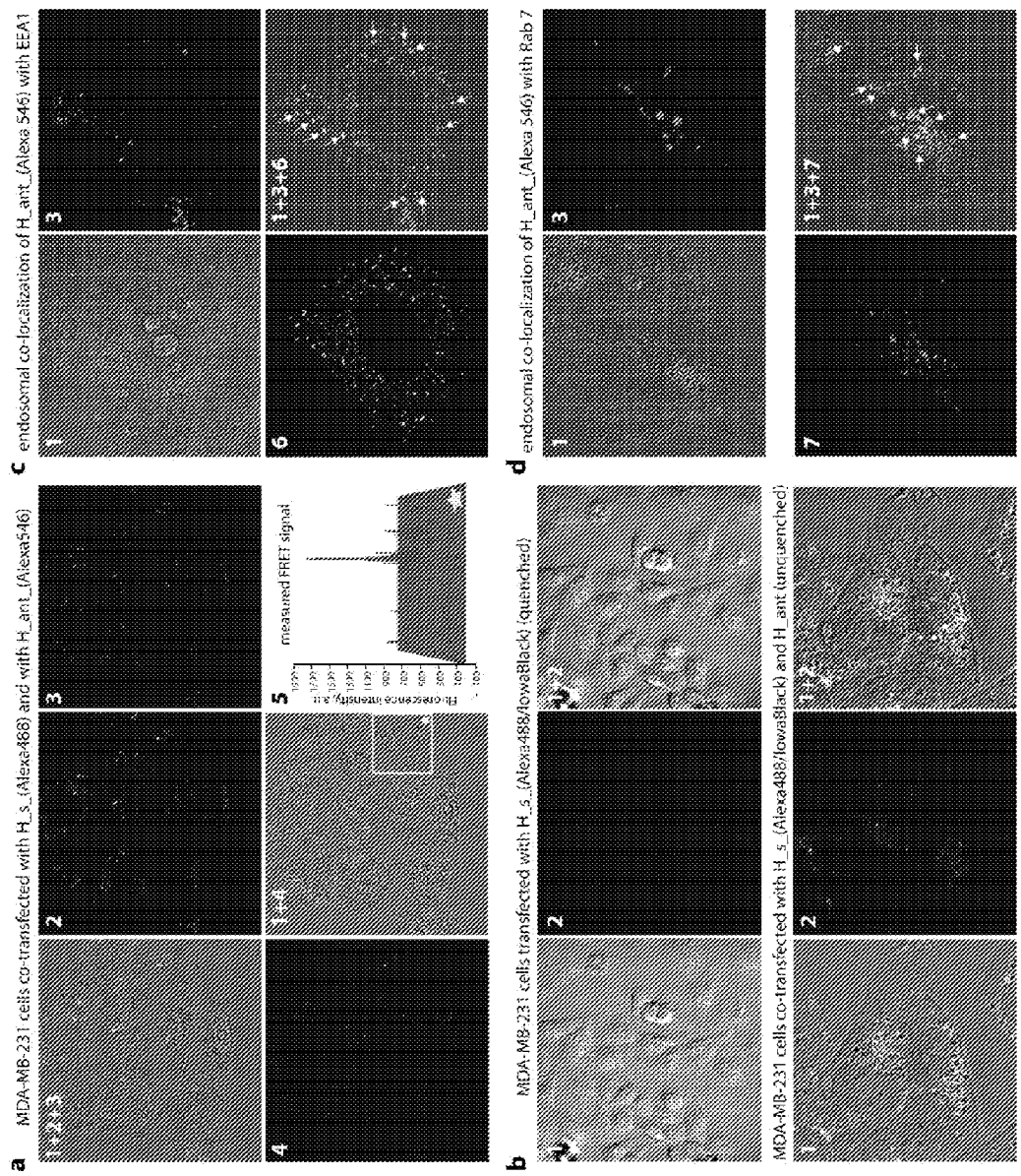
FIGS. 40A-40D shows the re-association and localization of auto-recognizing R/DNA hybrids in human breast cancer cells (MDA-MB-231) visualized by confocal fluorescence microscopy.

The ability of the auto-recognizing R/DNA hybrids to enter and recombine within cells was assessed through confocal microscopy. R/DNA hybrids labeled with Alexa488 and Alexa546 were co-transfected in MDA MB 231 cells and imaged through confocal microscopy the next day (FIGS. 40 and 41). The punctuated inhomogeneous pattern observed in FIG. 40A is consistent with an endosomal location of the fluorescent hybrids FIG. 40. The overlap of the Alexa488 and Alexa546 fluorescence indicates that while a portion of them are distributed in distinct endosomes, a significant amount of co-localization characterized by a yellow signal takes place. To further check whether FRET occurs within those endosomal compartments, Alexa546 sensitized emission was imaged. The sample was excited at 488 nm and the emission of Alexa546 was collected. The FRET signal remaining upon bleed through correction is presented in FIG. 40A (1+4 and 5). Not only do the R/DNA hybrid co-localize in endosomic compartments, they also exhibit considerable FRET. Since a high concentration of hybrids is accumulated within endosomes, the FRET observed could still emanate from close proximity that did not lead to recombination. In order to address this point in a more conclusive manner, a different system was used. Instead of introducing fluorophores able to exhibit FRET upon re-association a quenched auto-recognizing duplex containing Alexa488 and IowaBlack fluorescence quencher were transfected. This duplex by itself does not exhibit any fluorescence (FIGS. 40B, top row and 42). However, if this quenched duplex is co-transfected with an auto recognizing R/DNA hybrid, an unquenching of Alexa488 within the endosomic compartments was observed, additionally evidencing the occurrence of re-association between the two constructs within the cells.

Example 6

Release of siRNA Upon Re-Association R/DNA Hybrids in Cells

Figure 43:
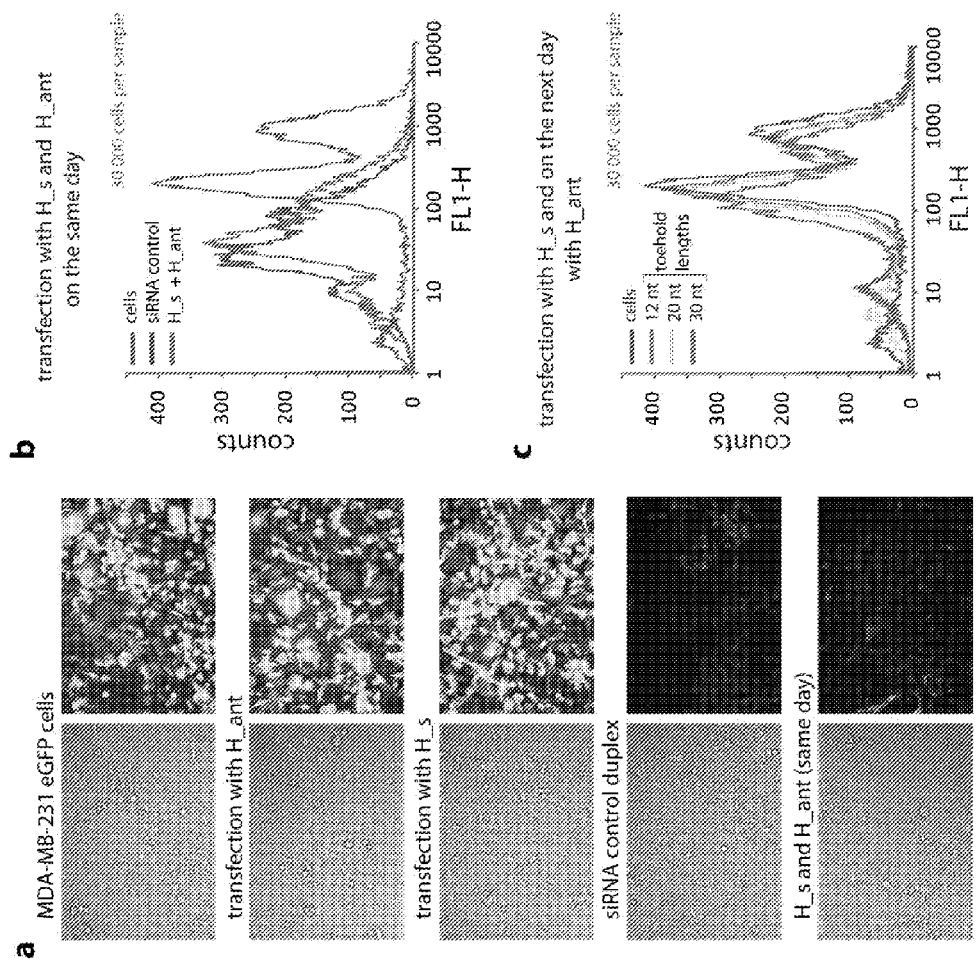
Figure 45:
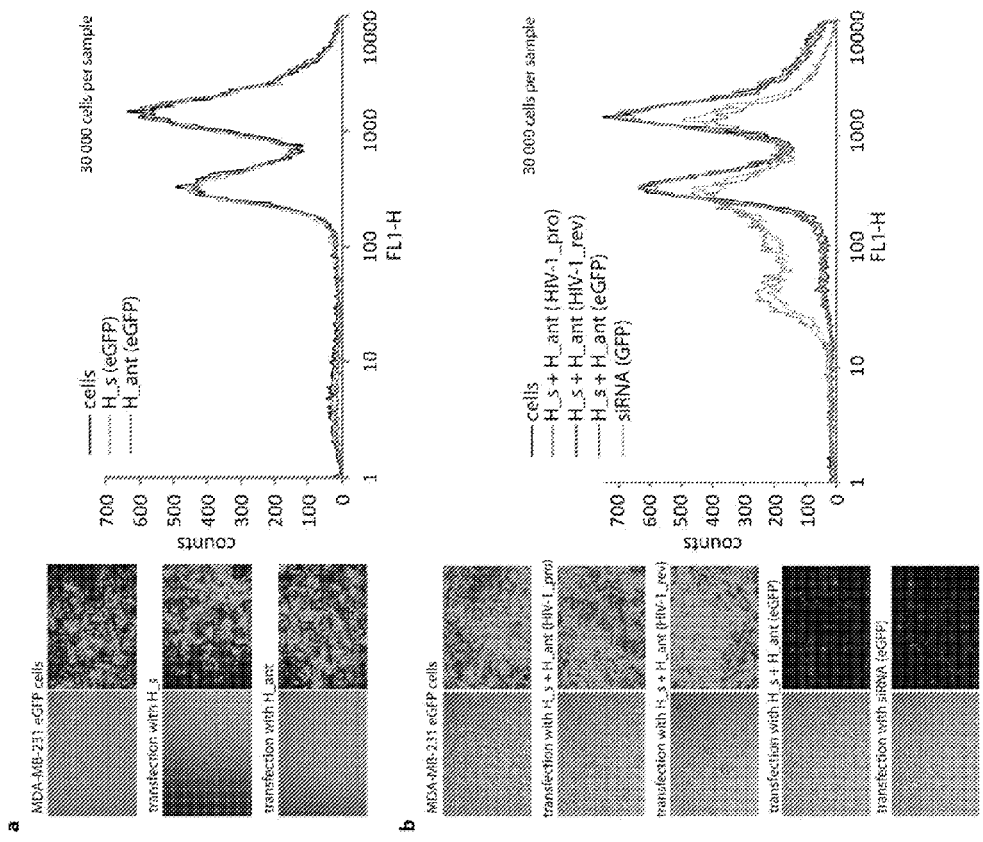

To assess the ability of auto-recognizing R/DNA hybrids to recombine in cells and release therapeutic moieties (siRNAs), experiments with human breast cancer cells stably expressing eGFP (MDA-MB231/eGFP) were carried out (FIGS. 44 and 45). First, cells were co-transfected with only one hybrid at a time (H_s or H_ant) and three days after, the level of eGFP expression was analyzed with fluorescence microscopy and flow cytometry. All experiments were repeated at least three times. The results demonstrated no silencing in eGFP production caused by the individual hybrids (FIGS. 43 and 45A). However, when cells were co-transfected with separately prepared complexes of L2K with individual cognate R/DNA hybrids (H_s/L2K and H_ant/L2K), the level of silencing measured three days after was comparable to the silencing resulting from the transfections with control pre-formed asymmetric Dicer substrate siRNAs (FIGS. 43 and 43B). Based on the kinetic studies of re-association for L2K bound R/DNA hybrids (FIGS. 35D & 35E), it can concluded that the re-association of co-transfected hybrids and siRNA release takes place not in the media but in cells.

As negative controls, unrelated to eGFP silencing, auto-recognizing R/DNA hybrids designed against HIV-1 were used (FIG. 43B). Also, the release of classical-size siRNAs (21 nts) upon R/DNA hybrids re-association demonstrated lower silencing efficiency comparing to asymmetric Dicer substrate siRNAs (FIG. 46) which is in agreement with published data (Rose, S. D. et al., *Nucleic acids research* 33, 4140-4156 (2005)).

Figure 47:
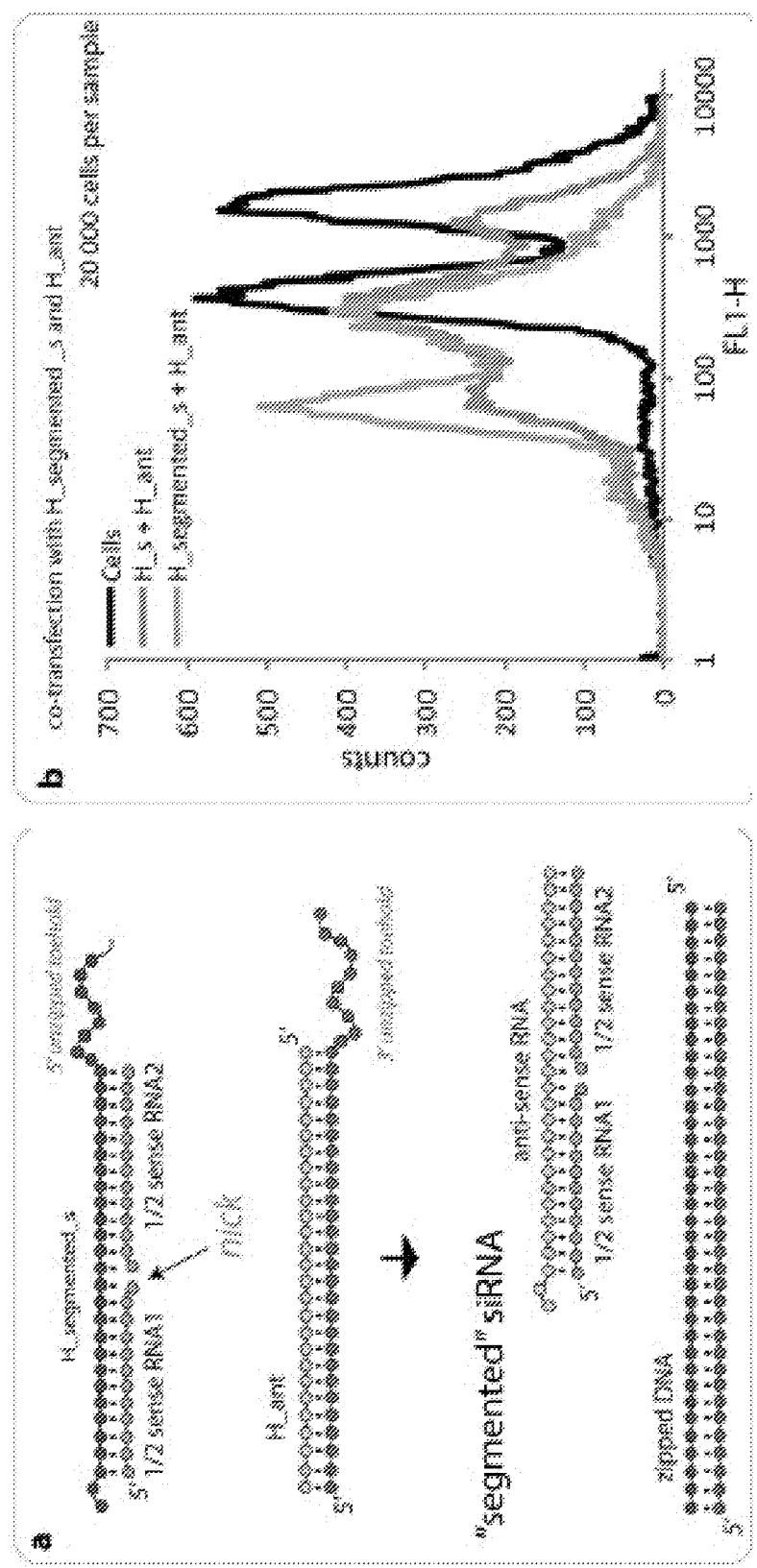

Furthermore, small internally segmented interfering RNAs reported to have a higher silencing potency (Bramsen, J. B. et al., *Nucleic Acids Res* 35, 5886-5897 (2007)), were tested at the level of R/DNA hybrids (FIG. 47). In these experiments, the sense strand was segmented into two shorter RNAs (1/2sense1 and 1/2sense2) that were used together with a DNA sense strand to make a segmented R/DNA hybrid (H_segmented_s). The co-transfection results showed a higher silencing efficiency for hybrids with segmented siRNAs which is in agreement with published data (Bramsen, J. B. et al., *Nucleic Acids Res* 35, 5886-5897 (2007)).

Example 7

Effect of Toehold Length on siRNA Release in Cells

The experiments in which the R/DNA hybrids were co-transfected on two different days revealed some silencing as well (FIG. 43B, red line). This serves as additional evidence for the intracellular re-association and therapeutic release of siRNA. The effect of the lengths of the zipping toeholds in R/DNA hybrids on the relative efficiencies of siRNA release were then investigated. The relative silencing of eGFP was statistically analyzed for constructs having toeholds of 12, 20 and 30 nts, which were co-transfected on the same and on two different days. The results presented in FIG. 48 show no difference in silencing efficiency for hybrids co-transfected the same day. However, when the individual hybrids were transfected with a one day interval the construct with a 30 nts toehold showed the highest efficiency (FIG. 43) while weaker and comparable silencing was observed for the constructs with 12 and 20 nts toeholds.

Example 8

Delivery and Re-Association of R/DNA Hybrid In Vivo

To assess the delivery of auto-recognizing R/DNA hybrids in vivo, bio-distribution experiments were carried out in athymic nude mice bearing xenograft tumors. R/DNA hybrids and Dicer substrate siRNAs fluorescently labeled with IRDye700 were systemically delivered to the mice by tail-vein injections. Consequently, in vivo bio-distribution and tumor uptake were evaluated by fluorescence imaging after 10 min, 20 min, 30 min, 45 min, 1 hour, 2 hours, and 3 hours (FIG. 49). The bio-distribution profile shows a relatively higher uptake of the auto-recognizing R/DNA hybrids within the tumor compared to other major organs (spleen, liver, kidney, intestines, and gallbladder) within the time course of 3 hours. Fluorescent signals in the spleen, lungs, heart and brain were not detected. At the three hour time point, some organs, tumor and blood samples were quantitatively analyzed ex vivo. As shown in FIG. 49B, the relative concentration of R/DNA hybrids in mouse blood after three hours is almost six times higher than the concentration of siRNAs. The tumor/kidney ratios presented in FIG. 49C indicate a significantly higher uptake (~2.5-fold) for the R/DNA hybrids compared to siRNAs accumulated mostly in the kidneys. This can be attributed to the relative chemical instability of siRNAs in vivo leading to its degradation and renal excretion. In addition, we performed in vivo gene silencing of eGFP expressing MDA-MB-231 xenografts. Auto-recognizing R/DNA hybrids and siRNAs against eGFP were administrated by intra-tumor injections into two mice. The extents of silencing were analyzed ex vivo by measuring the fluorescent intensities of eGFP in tumors (compared to the control animal) five days post-injection (FIG. 49D and FIG. 50). Both injections with the R/DNA hybrids and the siRNAs resulted in a comparable decrease of ~70% in eGFP fluorescent intensities. These results are in a good agreement with our multiple in vitro silencing experiments, confirming a successful silencing of target genes by auto-recognizing R/DNA hybrids.

Example 9

Auto-Recognizing R/DNA Hybrids Against HIV- and Cancer Targets

To demonstrate the generality of the approach and the feasibility of using auto-recognizing R/DNA hybrids as therapeutic moieties, several HIV-1 and cancer genes were also targeted.

In the case of HIV-1 target genes, siRNAs previously described (Lowe, J. T. et al., *Mol Ther* 20, 820-828 (2012)) were used to design auto-recognizing R/DNA hybrids and corresponding siRNA duplexes. Two main targets—the protease-coding region found in full-length, genomic RNA that encodes the Gag and Gag-Pol polyprotein precursors (Pro_siRNA), and env mRNA that encodes the HIV-1 glycoproteins (Env_siRNA, located in gp120) were selected. Results presented in FIG. 51 demonstrated dose-dependent viral inhibition with siRNA and R/DNA hybrids. HIV-1 production was inhibited by 85% with only 20 nM of the Pro_Hybrids. Env_siRNA, which also binds full-length mRNA encoding Gag and Gag-Pol, reduced virus production by 65% to 80% (FIG. 51A). Levels of gp160 and gp120 were also reduced inside the cell (FIG. 51B). Inhibition of HIV-1 gp160 and gp120 reached as high as 76% and 82%, respectively (data not shown). The total amount of Gag (Pr55+p24/p25) was reduced on average by 72% with 20 nM of Pro Hybrids siRNA after recombination inside the cell. Env_Hybrids siRNA knocked down up to 75% of cellular Gag (FIG. 51B). We also tested different approaches to study the toxicity effect of these siRNAs in our system. Toxicity levels were low, as demonstrated by expressing of a co-transfected vector encoding *Renilla* luciferase (supporting FIG. 52). Cellular expression levels of glyceraldehyde 3-phosphate dehydrogenase (GAPDH) were also not significantly affected (data not show). These results clearly demonstrate that auto-recognizing R/DNA hybrids can recombine inside the cell and inhibit HIV-1 through different targets.

As a cancer target gene, glutathione S-transferase P1 (GSTP1) was chosen. GSTP1 is the phase II detoxification enzyme that catalyzes conjugation of glutathione to a variety of electrophilic compounds, including anticancer agents. GSTP1 is believed to play an important protective role in tumor cell pathogenesis and survival, and the overexpression of GSTP1 that is frequently observed in cancer has been linked to chemoresistance (Townsend, D. M. & Tew, K. D., Oncogene 22, 7369-7375 (2003)). In addition, GSTP1 has been proposed to inhibit the mitogen-activated protein kinase (MAPK) pathway through direct interaction with c-jun-NH2-kinase 1 (JNK1), decreasing a cells' sensitivity to drug-induced apoptosis (Townsend, D. M. & Tew, K. D., Oncogene 22, 7369-7375 (2003)). Downregulation of GSTP1 expression by RNA interference could be used therapeutically to sensitize cancer cells to chemotherapy.

It was shown that the endogenous GSTP1 protein expression could be effectively down-regulated with R/DNA hybrids individually co-transfected on two different days, 24 hours apart. Incubation of the A549 lung adenocarcinoma cells with R/DNA hybrids resulted in significant (~55%) decrease in GSTP1 protein production (supporting FIG. 53).

Example 10

R/DNA Chimeric Polyfunctional Nanoparticles (NP) Bind and Enter HIV Infected Cells and Increase Apoptosis in HIV Infected Cells Therapeutic R/DNA chimeric polyfunctional nanoparticles (NP) were computationally designed towards recognition, visualization, and functional cure of HIV infection. Without being bound to a particular theory, the release of multiple therapeutic siRNAs can be triggered by the presence of at least two R/DNA NP separately entering cells infected with HIV. Two or more cognate R/DNA NP are decorated with different recognition domains targeting expressing cell surface proteins characteristic of HIV infected cells (e.g. aptamers for gp41 and/or gp120).

Therapeutic R/DNA NP are shown in FIG. 54. Each of the cognate R/DNA NP is independently therapeutically inactive and has several functionalities (cell surface recognition domains, fluorescent tags, domains facilitating cellular uptakes, etc.) as well as several split functionalities (split lipase, split green fluorescent protein (GFP), etc.) covalently attached to the DNA strands.

In one embodiment, two or more cognate R/DNA NP are decorated with different recognition domains targeting cell surface proteins characteristic of HIV infected cells (e.g. aptamers for gp41 and/or gp120). Computational predictions show that the presence of both cognate R/DNA NP in close proximity (e.g. in the endosome or cytoplasm) promotes structural re-association through engineered toehold recognition. This activates the functionalities (lipase for endosomal escape, GFP for visualization, etc.) and releases therapeutic siRNAs. Using small interfering RNAs (siRNAs) it is routinely possible to knock down target mRNA expression. Furthermore, it is possible to induce cell death (apoptosis) through the combinatorial RNA interference (co-RNAi) by simultaneously targeting several human apoptosis inhibitor genes with different siRNAs.

Importantly, in the R/DNA NP of the invention, the number of therapeutic siRNAs is fully programmable by modulating the number of branches depending on particular tasks. The human enzyme Dicer is inactive against individual R/DNA NP, but cleaves the recombined siRNAs and transfers one of the siRNA strands (the guide strand) to the RNA induced silencing complex (RISC), which in turns activates the co-RNAi. The guide strand is designed to have an antisense sequence to human apoptosis inhibitor genes (BCL-2, FLIP, STAT3, XIAP, etc.). Thus, the activation of co-RNAi results in apoptosis of an HIV-infected cell.

It is known that the pharmokinetics of regular siRNAs is very poor because of their chemical instabilities and small sizes (<10 nm) which promote kidney clearance. The R/DNA NP are chemically stable with an average size exceeding 10 nm which makes them attractive candidates for therapeutical applications. Such synthetic "smart" R/DNA NP represent a key building block for eradication therapies of HIV infected patients.

Example 11

Auto-Recognizing R/DNA Duplexes Targeting GFP Decreased GFP Expression in Cells

Ab initio and studied self-recognizing R/DNA duplex system, targeting the production of GFP in human cells were engineered (FIG. 55). The auto-recognizing R/DNA duplexes effectively found each other in cells and released siRNAs which knocked down the synthesis of GFP. Thus, the auto-recognizing R/DNA duplexes were not processed by Dicer until recombined. Moreover, even when auto-recognizing R/DNA duplexes were individually transfected on two different days, the siRNA release was still observed.

Example 12

Therapeutic R/DNA NP Having HIV Cell Surface Recognition Domains and siRNA Sequences Targeting Apoptosis Inhibitor Genes Increase Apoptosis in HIV Infected Cells Novel and leading bioinformatics approaches for RNA secondary structure prediction, RNA 3D structure modeling and RNA sequence design have been developed for the computational characterization of the designed particles. Generating three-dimensional models of therapeutic R/DNA NP subjected to molecular dynamics simulations provides important information regarding the kinetic behavior of synthetic R/DNA NP.

In silico designed library of therapeutic R/DNA NP are tested in vitro and in HIV infected cells. Newly designed sequences are tested in vitro for their abilities to assemble into the R/DNA NP of desirable compositions. Once assembled, cognate R/DNA NP are tested in pairs for their auto-recognition (binding affinities, kinetics of recombination, etc.). The release of siRNA duplexes from cognate R/DNA NP pairs is amenable to human Dicer processivity and is useful for therapy. Dicer activity is expected in cases of auto-recognized recombination. If required, proper chemical modifications on RNA structures is performed to promote Dicer processivity of the recombined siRNAs and further loading of the RISC complex.

To test the activity of R/DNA NP pairs, HIV infected human cells (H9 and/or Jurkat cells) are transfected with cognate R/DNA NP at different time points, concentrations and compositions. R/DNA NP having cell surface recognition domains targeting cell surface HIV markers bind to and enter the HIV infected cells The R/DNA NP contain siRNA sequences targeting apoptosis inhibitor genes increase apoptosis in the HIV infected cells. Without being bound to a particular theory, the presence of both cognate R/DNA NP in a close proximity (e.g. in endosome or cytoplasm) promotes structural re-association through engineered toehold recognition moieties. Apoptosis can be measured by a commercial kit, e.g., by flow cytometry using the BD™ Mito-Screen (JC-1) flow cytometry kit. Non-infected cell lines are used as a control.

Example 13

Auto-Recognizing RNA/DNA Hybrids Releasing Multiple Functionalities Upon Re-Association One can split multiple functionalities (FRET, aptamers, ribozymes, siRNAs, proteins, etc.) and introduce them simultaneously in auto-recognizing RNA/DNA hybrids. These hybrids, by themselves, are inactive, but the presence of at least two of them results in re-association and functionality release (FIG. 56). Several hybrids containing aptamers, various siRNAs (against eGFP and HIV-1), and fluorescent pair of Foerster dyes were designed and experimentally tested. The sequences are shown below:

sense
(SEQ ID NO: 6)
5'-pACCCUGAAGUUCAUCUGCACC antisense
(SEQ ID NO: 32)
5'-pUGCAGAUGAACUUCAGGGUCA MG aptamer 1
(SEQ ID NO: 33)
5'-UAUGACAGGUAACGAAUGACAGUAU MG aptamer 2
(SEQ ID NO: 34)
5'-AUACUGUCCGACAUGUCAUA Hybrids for siRNA and MG aptamer
Small letter sequences were added to DNA strands to compensate asymmetry of MG aptamer and 2nts 3' overhangs of siRNAs D_4_s
(SEQ ID NO: 35)
5'-GGAGACCGTGACGGTGCAGATGAACTTCAGGGTca D_4_a
(SEQ ID NO: 36)
5'-TGACCCTGAAGTTCATCTGCAccGTCACGGTCTCC

D_4_mg1
(SEQ ID NO: 37)
5'-GGAGACCGTGACATACTGTCATTCGTTACCATGTCATAgcatg

D_4_mg2
(SEQ ID NO: 38)
5'-catgcTATGACATGTCGGACAGTATGTCACGGTCTCC

MG aptamer and siRNA

D_4_s_mg1
5'-
(SEQ ID NO: 39)
GGAGACCGTGACGGTGCAGATGAACTTCAGGGTcaATACTGTCATTCGTTACCATGTCATAgcatg D_4_a_mg2
(SEQ ID NO: 40)
5'-catgcTATGACATGTCGGACAGTATTGACCCTGAAGTTCATCTGCAccGTCACGGTATCC

D_4_mg1_s
(SEQ ID NO: 41)
5'-AL546-GGAGACCGTGACATACTGTCATTCGTTACCATGTCATAgcatgGGTGCACATGAACTTCAGGGTca D_4_mg2_a
(SEQ ID NO: 42)
5'-TGACCCTGAAGTTCATCTGCAcccatgcTATGACATGTCGGACAGTATGTCACGGTCTCC-AL488

2 siRNAs

D_4_ss
(SEQ ID NO: 43)
5'-GGAGACCGTGACGGTGCAGATGAACTTCAGGGTcaGGTGCAGATGAACTTCAGGGTca

D_4_aa
(SEQ ID NO: 44)
5'-TGACCCTGAAGTTCATCTGCAccTGACCCTGAAGTTCATCTGCAccGTCACGGTCTCC

MG aptamer and 2 siRNAs

D_4_s_s_mg1
(SEQ ID NO: 45)
5'-GGAGACCGTGACGGTGCAGATGAACTTCAGGGTcaATACTGTCATTCGTTACCATGTCATAgcatg D_4_a_a_mg2
(SEQ ID NO: 46)
5'-catgcTATGACATGTCGGACAGTATTGACCCTGAAGTTCATCTGCAccTGACCCTGAAGTTCATCTGCAccGTCACGGTCTCC

D_4_s_mg1_s
(SEQ ID NO: 47)
5'-GGAGACCGTGACGGTGCAGATGAACTTCAGGGTcaATACTGTCATTCGTTACCATGTCATAgcatgGGTGCAGATGAACTTCAGGGTca D_4_a_mg2_a
(SEQ ID NO: 48)
5'-TGACCCTGAAGTTCATCTGCAcccatgcTATGACATGTCGGACAGTATTGACCCTGAAGTTCATCTGCAccGTCACGGTCTCC**

D_4_mg1_s_s
(SEQ ID NO: 49)
5'-GGAGACCGTGACATACTGTCATTCGTTACCATGTCATAgcatgGGTGCAGATGAACTTCAGGGTcaGGTGCAGATGAACTTCAGGGTca D_4_mg2_a_a
(SEQ ID NO: 50)
5'-TGACCCTGAAGTTCATCTGCAccTGACCCTGAAGTTCATCTGCAcccatgcTATGACATGTCGGACAGTATGTCACGGTCTCC

3 siRNAs

D_4_sss
(SEQ ID NO: 51)
5'-GGAGACCGTGACGGTGCAGATGAACTTCAGGGTcaGGTGCAGATGAACTTCAGGGTca -continued D_4_aaa
(SEQ ID NO: 52)
5'-TGACCCTGAAGTTCATCTGCAccTGACCCTGAAGTTCATCTGCAccT GACCCTGAAGTTCATCTGCAccGTCACGGTCTCC 3 siRNAs against HIV-1 (1877, 1dr, Gag)

Protease (Pro). Positions 2332 to 2356, according
to pNL4-3.-1877
sense
(SEQ ID NO:8)
5'-pGAGCAGAUGAUACAGUAUUAGAAGA antisense
(SEQ ID NO:9)
5'-UCUUCUAAUACUGUAUCAUCUGCUCCU Envelope (Env). gp120, Positions 7642 to 7665,
accord to pNL4-3.-7193
sense
(SEQ ID NO: 10)
5'-GGACAAUUGGAGAAGUGAAUUAUAUU antisense
(SEQ ID NO: 11)
5'-pUAUAAUUCACUUCUCCAAUUGUCC R/T-3722
sense
(SEQ ID NO: 53)
5'-pGAGGAAAUGAACAAGUAGAUAAAU antisense
(SEQ ID NO: 54)
5'-AUUUAUCUACUUGUUCAUUUCCUCCA D_4_s(18-71-37)
(SEQ ID NO: 55)
GGAGACCGTGACATTTATCTACTTGTTCATTTCCTCCAAATATAATTCAC

TTCTCCAATTGTCCTCTTCTAATACTGTATCATCTGCTCCT

D_4_a(18-71-37)
(SEQ ID NO: 56)
AGGAGCAGATGATACAGTATTAGAAGAGGACAATTGGAGAAGTGAATTAT

ATTTGGAGGAAATGAACAAGTAGATAAATGTCACGGTCTCC

Figure 57:
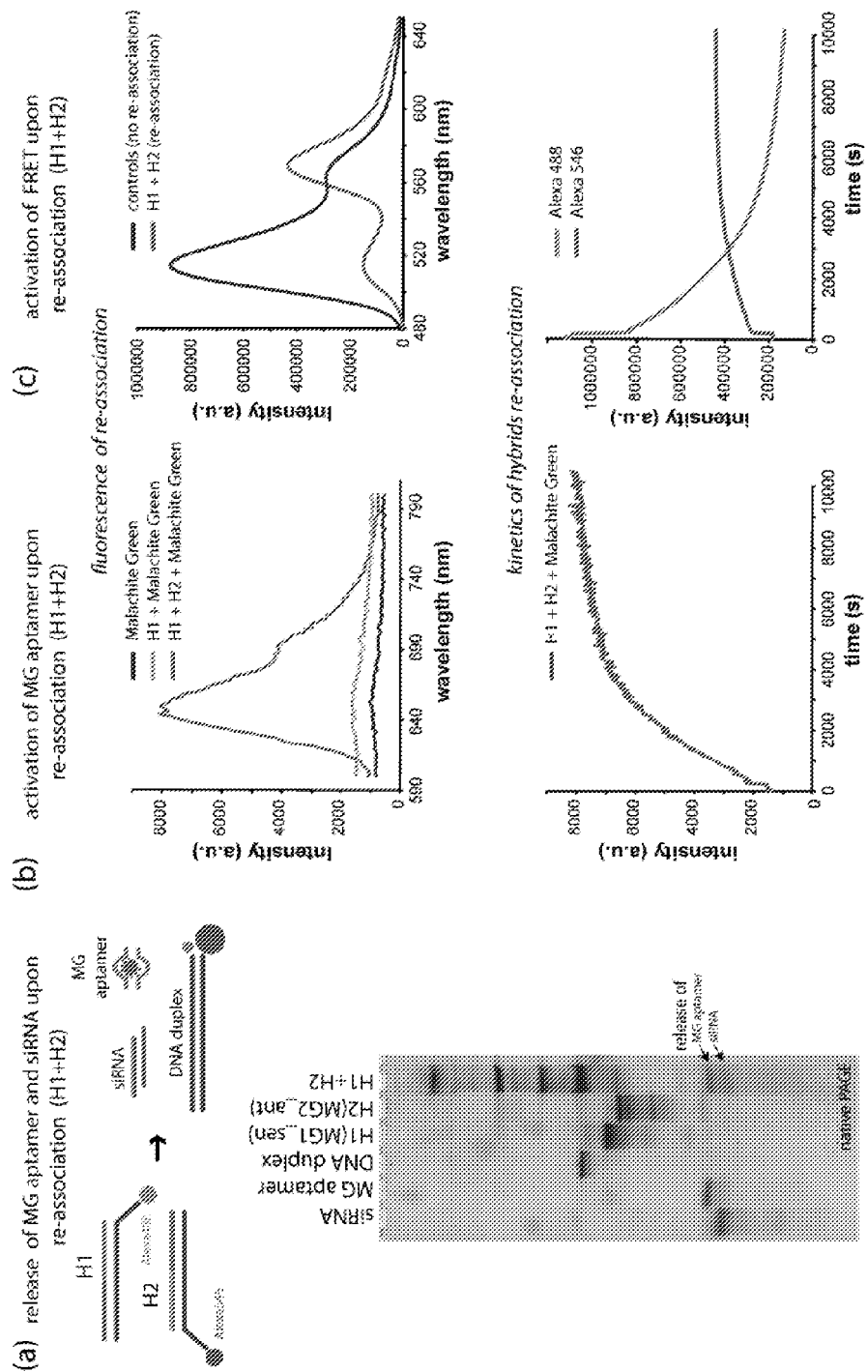

The results show the successful release of all functionalities. A split Malachite Green aptamer as a fluorescent reporter which was embedded in hybrids at different positions was used (FIGS. 57 and 58). We chose the triphenylmethane dye, Malachite Green (MG), as the fluorescent reporter because in its unbound state in water solution it exhibits extremely low fluorescence quantum yield from the S1 excited state because of efficient internal conversion. The emission of the dye increases substantially when the non-radiative relaxation channels from S1 are shut down. Whereas the detailed underlying mechanisms of this phenomenon are still being debated, related studies show that "rigidifying" the dye by placing it in a highly viscous environment or in a binding cage increases its emission dramatically. For instance, it was reported recently that the emission of MG increases by several orders of magnitude upon binding to an RNA aptamer obtained by in vitro selection (SELEX).

Figure 59:
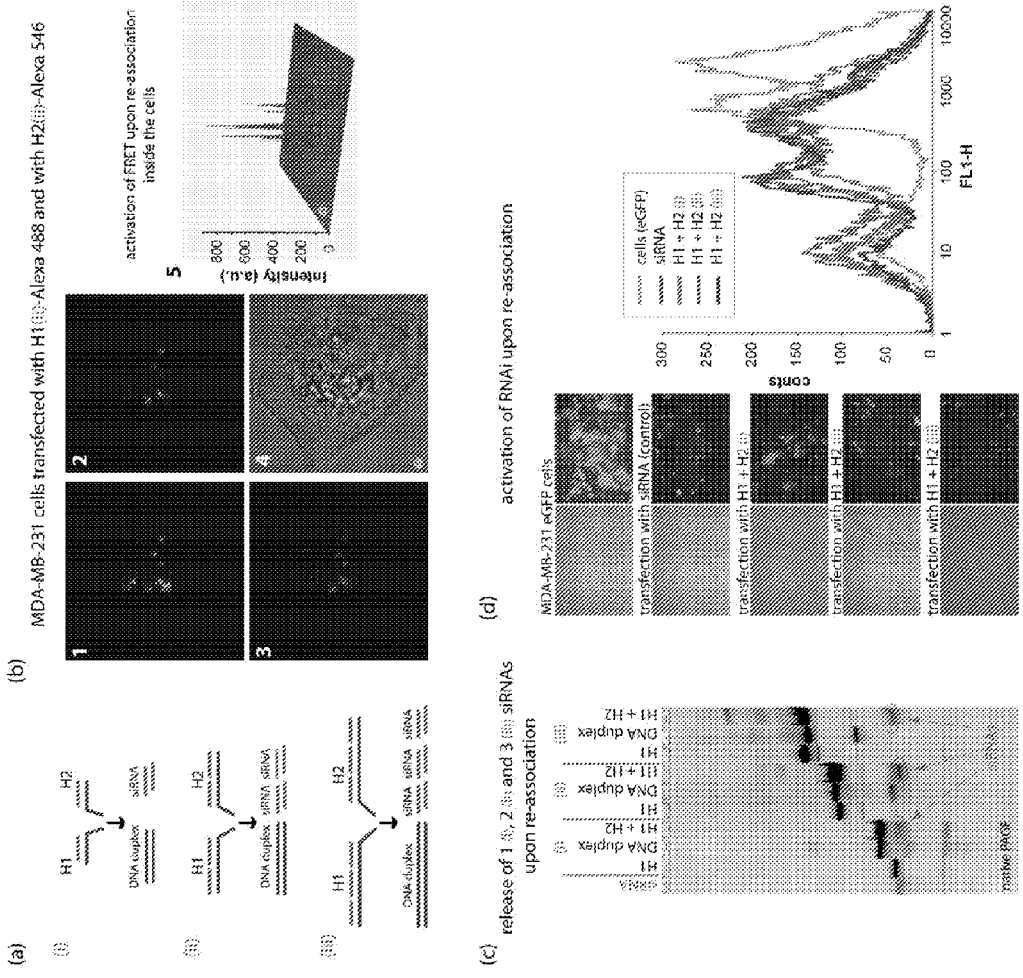

The ability of the auto-recognizing R/DNA hybrids to enter and recombine within cells was assessed through confocal microscopy (FIG. 59). R/DNA hybrids labeled with Alexa488 and Alexa546 were co-transfected into MDA-MB-231 cells and imaged through confocal microscopy the next day. The punctuated inhomogeneous pattern observed in FIG. 59B is consistent with an endosomal location of the fluorescent hybrids (FIGS. 59C and 59D). The overlap of the Alexa488 and Alexa546 fluorescence indicates that while a portion of them are distributed in distinct endosomes, a significant amount of co-localization characterized by a yellow signal takes place. To further check whether FRET occurs within those endosomal compartments, Alexa546 sensitized emission was imaged. The sample was excited at 488 nm and the emission of Alexa546 was collected. The FRET signal remaining upon bleed through correction is presented in FIG. 59B (4 and 5).

To assess the ability of auto-recognizing R/DNA hybrids to re-associate in cells and release functional moieties (asymmetric Dicer substrate siRNAs), experiments with human breast cancer cells stably expressing eGFP (MDA-MB-231/eGFP) were carried out (FIG. 59D). First, cells were co-transfected with only one hybrid at a time (H1 or H2) and three days after, the level of eGFP expression was analyzed with fluorescence microscopy and flow cytometry. All experiments were repeated at least three times. The results demonstrated no silencing in eGFP production caused by the individual hybrids. However, when cells were co-transfected with separately prepared complexes of L2K and individual cognate R/DNA hybrids (H1/L2K and H2/L2K), the level of silencing measured three days after was comparable to the silencing resulting from the transfections with control pre-formed asymmetric Dicer substrate siRNAs with the higher silencing efficiencies for the hybrids releasing three siRNAs (Hybrids (iii)).

The above examples were carried out using the following materials and methods.

RNA and DNA Sequence Design.

Single-stranded DNA toehold sequences were optimized with the mFold program (Zuker, M, *Nucleic Acids Res* 31, 3406-3415 (2003)) to minimize the occurrence of alternative secondary structure folds. siRNA sequences for the duplex were used from previous studies (Afonin, K. A. et al., *Nat Protoc* 6, 2022-2034 (2011) and Rose, S. D. et al., *Nucleic Acids Res* 33, 4140-4156 (2005)). The full list of RNA and DNA sequences used is available (Supporting Information). RNAs, DNAs and fluorescently labeled DNAs for hybrid duplexes were purchased from Integrated DNA Technologies, Inc. In the case of the fluorescently labeled DNAs, additional linkers of two nucleotides (either TT or AA) were added for the fluorescent tags.

Hybrid R/DNA Duplexes Assemblies and Native PAGE.

There is a variety of duplex formation approaches detailed elsewhere (Afonin, K. A. et al., *Nat Protoc* 6, 2022-2034 (2011)) and in this work; we used the fastest protocol. The oligo (RNAs and/DNAs) units at concentrations specified in the text were mixed in doubledeionized water and incubated in a heat block at 95 C for two minutes. The block containing the samples was removed from heat, and placed directly on ice over a period of 10 minutes. Hybridization buffer (89 mM Tris, 80 mM Boric Acid (pH 8.3), 10 mM magnesium acetate) was added to the mixtures either prior to heating, or after the step at 95. C. Native PAGE experiments were performed as described (Afonin, K. A. et al., *Nat Protoc* 6, 2022-2034 (2011); Afonin, K. A. et al., *Chembiochem* 9, 1902-1905 (2008); Afonin, K. A. & Leontis, N. B. *Journal of the American Chemical Society* 128, 16131-16137 (2006)) Typically, assembly experiments reported were analyzed at 10° C. on 7% (29:1) native polyacrylamide gels in the presence of 89 mM Trisborate, pH 8.3, 2 mM Mg(OAc)$_2$. A Hitachi FMBIO II Multi-View Imager was used to visualize SYBR Gold stained R/DNA hybrids.

Recombinant Human Dicer Assay.

Hybrid R/DNA duplexes were prepared as described above to a final concentration of 3 μM. For dicing experiments, samples were incubated for 4 hours at 37° C. with recombinant human turbo dicer enzyme kit (Genlantis), containing an ultra-active form of human recombinant dicer enzyme, according to the manufacturer's suggested protocol. Dicing reactions were quenched by adding dicer stop solution (provided by the manufacturer) prior to analysis on 2 mM Mg(OAc)$_2$ native 7% PAGE (described above).

Human Serum Degradation Studies.

Aliquots of freshly drawn human whole blood serum (blood was allowed to coagulate, then spun down and supernatant was collected) were immediately used for each new study. RNA duplexes and R/DNA hybrids at the concentration 100 times above that used in our in vitro efficacy studies were kept on ice prior to incubation with 80% (v/v) human blood serum at 37° C. for various time periods. Final RNA concentration was 2 µM. Prior to immediate loading on 2% agarose gel, degradation time courses were quenched on dry ice. A Hitachi FMBIO II Multi-View Imager was used to visualize ethidium bromide stained RNA duplexes and R/DNA hybrids.

Fluorescence Studies.

To assess the re-association of R/DNA hybrids in vitro, FRET measurements were performed using a FluoroMax3 (Jobin-Yvon, Horiba). For all the experiments, the excitation wavelength was set at 460 nm and the excitation and emission slit widths were set at 2 nm. In a first set of experiments, complementary DNAs were modified with Alexa488 or Alexa546. To follow the kinetics of recombination, an Alexa488 R/DNA hybrid containing sense RNA was first incubated for two minutes at 37° C. and an Alexa543 R/DNA hybrid containing antisense RNA was then added in equimolar amounts specified in text. Upon excitation at 460 nm, the emissions at 520 nm and 570 nm were recorded simultaneously every 30 seconds to follow the process of re-association through FRET measurements. This was done with naked hybrids and hybrids pre-complexed with Lipofectamine 2000 in the amounts relevant for transfection conditions (see below). Static measurements were also performed upon 3 hours co-incubation of equimolar amounts of the two fluorescently labeled hybrids. In a second set of experiments a DNA duplex containing one strand modified with Alexa488 and another with IowaBlack FQ was used. The dequenching of Alexa488 upon addition of the Alexa543 R/DNA hybrid or unlabeled R/DNA hybrid was followed as described above for the FRET experiments. The decrease of Alexa488 fluorescence was fitted in Sigmaplot. A linear regression was applied to fit the data to a single exponential decay equation with 3 parameters as follows:
$y = y_0 + ae^{-kt}$ Stability assays with RQ1 DNase To study the stability of pre-formed duplex/L2K complexes in presence of nucleases, DNA duplexes containing one strand modified with Alexa488 and another with IowaBlack FQ were pre-incubated with L2K and the dequenching of Alexa488 upon digestion with RQ1 RNase free DNase (Promega) was followed as described above for the FRET experiments. As the control, quenched DNA duplexes were used alone. RQ1 RNase free DNase was used according to the manufacturer's protocol.

Transfection of Human Breast Cancer Cells with siRNA-Containing RNA NPs.

For assaying the delivery of functional R/DNA hybrids, human breast cancer cell line MDA-MB-231 (with or without eGFP) was grown in D-MEM media (Gibco BRL) supplemented with 10% FBS and penicillin-streptomycin in a 5% CO2 incubator. All transfections in this project were performed using Lipofectamine 2000 (L2K) purchased from Invitrogen. 10× or 50× solutions of R/DNA hybrids were pre-incubated at 30° C. with L2K. Prior to each transfection, the cell media was swapped with OPTI-MEM and prepared 10× or 50×RNA NP/L2K complex was added to the final concentration of 1×. The cells were incubated for 4 hours followed by the media change (D-MEM, 10% FCS, 1% pen-strep).

Microscopy.

To assess the re-association of R/DNA hybrids in cells, measurements were performed using a LSM 710 confocal microscope (Carl Zeiss) with a 63×, 1.4 NA magnification lens. MDA-MB-231 cells were plated in glass bottom petri dishes (Ibidi, Germany) and subjected to transfection with R/DNA hybrids as described above. In a first set of experiments R/DNA hybrids individually modified Alexa488 and Alexa546 were co-transfected into cells as described above. On the next day, the samples were fixed by incubation in 4% paraformaldehyde for 20 minutes at room temperature. Images of the cells were then taken to assess the appearance of FRET within the sample. For Alexa488 imaging, the 488 nm line of an Argon laser was used as excitation and the emission was collected between 493 and 557 nm. For Alexa546 imaging, a DPSS 561 laser was used for excitation and emission was collected between 566 and 680 nm. In order to evaluate the sensitized emission through FRET, images were taken exciting the sample with the 488 nm line and collecting emission between 566 and 680 nm. Because of spectral overlap, the FRET signal is contaminated by donor emission into the acceptor channel and by the excitation of acceptor molecules by the donor excitation wavelength. This bleed through was assessed through measurements performed with samples transfected with individual dyes and mathematically removed from the images of FRET. In another set of experiments, a DNA duplex containing one strand modified with Alexa 488 and another modified with Iowa Black FQ was used. This duplex was either transfected alone or cotransfected with an R/DNA hybrid able to recombine with the duplex. Alexa 488 fluorescence was monitored as described above. All images were taken with a pinhole adjusted to 1 airy unit.

Endosomal Co-Localization Studies.

To confirm the endosomal location of endocytosed fluorescently labeled R/DNA hybrids in cells, co-staining experiments with several endosomal markers were performed. In one set of experiments, the cells were transfected with Alexa 546 R/DNA hybrids. On the next day, the cells were fixed with 4% paraformaldehyde for 20 minutes at room temperature and handled at this temperature thereafter. Samples were washed three times with PBS and then permeabilized with 0.2% Triton X-100 for 20 minutes. Upon washing three times with PBS, samples were blocked for one hour with 1% BSA and then exposed to primary antibodies against the early endosome associated protein EEA1 (Cell signaling) or against the late endosome marker Rab7 (Cell signaling). Upon washing three times with PBS, the samples were stained with a secondary Alexa 488 antibody (Molecular Probes). In a second set of experiments, the cells were transfected with plasmids expressing GFP-Rab5 or GFP-Rab7. Two days upon transfection, the cells were re-transfected with Alexa 546 R/DNA hybrids and imaged the day after. In both sets of experiments, Alexa 488 and 546 fluorescence was analyzed by confocal microscopy as described above.

Flow Cytometry Experiments.

For statistical analysis with flow cytometry experiments, the MDA-MB-231 231 (with or without eGFP) cells grown in 12-well plates ($10 \times 10^4$ cells per well) were lifted with cell dissociation buffer, washed twice with PBS and the level of expression of eGFP was determined by fluorescence-activated cell sorting (FACS) analysis on a FACScalibur flow cytometer (BD Bioscience). At least 20,000 events were collected and analyzed using the Cell quest software.

In Vivo Experiments.

Animal studies were performed according to the Frederick National Laboratory for Cancer Research (Frederick, Md.) Animal Care and Use Committee guidelines. For all experiments, $10^6$ MDA-MB-231 tumor cells were injected in the flank of each athymic nude mouse (Charles River Laboratories, Frederick, Md.). Bio-distribution experiments were performed when the tumors reached 5 mm in their longest diameter (about two weeks after MDA-MB-231 (no eGFP) injection). The mice were injected once in the tail vein with 100 µl (500 nM) of siRNA_IRDye700 or R/DNA_IRDye700 associated with bolaamphiphilic cationic carriers at 10 µg/ml (described in Grinberg, S. et al., *Langmuir* 21, 7638-7645 (2005)). Control mice were injected with 100 µl of PBS buffer. Fluorescence imaging (Maestro GNIR-FLEX, Cambridge Research & Instrumentation, Inc. Woburn, Mass.) was performed at baseline (pre-injection for determining auto-fluorescence), and 10 min, 20 min, 30 min, 45 min, 1 hr and 2 hrs and 3 hrs post injection while the animal was anesthetized (1-2% isoflurane in $O_2$ at 1 L/min flow). The animal's internal temperature was maintained prior, during the scan (heated imaging table), and post imaging while the animal recovered from anesthesia. Image analysis (image library for auto-fluorescence and contrast agent) was performed according to manufacturer's protocol (Maestro software 2.10.0, CRi, Woburn, Mass.). Due to the IR wavelength parameters of the contrast agent, image acquisition utilized an excitation filter (590±15 nm), emission filter (645 nm long pass) and a multispectral acquisition of 650-850 nm with 10 nm steps. Regions of interests were drawn around different organs and the total signal (counts/s) recovered for the different time points. The signal was then normalized by the weight of the different organs. After the 3 hrs post injection time-point, mice were euthanized ($CO_2$ asphyxiation as per ACUC guideline) to measure pertinent organ (spleen, lung, brain, liver, kidney, intestines, heart, tumor, and bladder) weights and uptake implementing the in vivo imaging acquisition parameters. For silencing experiments MDA-MB-231 tumor cells expressing eGFP were used. 5 days post tumor cell injection, the mice were injected intra-tumorally with 100 µl (500 nM) of either siRNA or co-injected with self-recognizing R/DNA hybrids 50 µl (500 nM) each, associated with bolaamphiphilic cationic carriers at 10 µg/ml (described elsewhere). Control mice were injected with 100 µl of PBS buffer. After five (120 hours) and ten days (240 hours), mice were sacrificed. Tumors were removed from mice, fixed overnight at 4 t in 4% PFA, then transferred to 20% sucrose overnight at 4° C. Excess sucrose was blotted from the tumor, and the tumor was embedded in OCT Compound (Tissue-Tek). 10 µm cryosections were mounted on slides and stained with DAPI (Invitrogen) then coverslipped with Prolong Gold a/Fade reagent (Invitrogen). Images were captured using Nikon's Eclipse 80i microscope, with a QImaging Retiga-2000R camera and Nikon's NIS-Elements AR Imaging Software.

HIV-1 Inhibition by Auto-Recognizing R/DNA Hybrids.

To test the potential for HIV-1 inhibition from hybrids after intracellular re-association, Hela cells were co-transfected with the WT HIV-1 molecular clone, pNL4-3, and the R/DNA hybrids. Two different targets were chosen: Protease, targeting the full-length, genomic mRNA; and gp120, targeting both env and full-length, genomic mRNAs. As knockdown controls, heteroduplex siRNAs were used. siRNA concentrations used in the assays were 5, 10 and 20 nM. Incubation of Hybrids Protease_antisense and Protease_sense with pNL4-3 and Lipofectamine 2000 (Invitrogen) was performed separately and then added to the cells (2 µg of DNA and 2 µl of Lipofectamine 2000/well). At 48 h posttransfection, the supernatants were harvested and the reverse transcriptase (RT) activity was measured in an in vitro reaction (Freed 1994). Levels of RT activity are directly proportional to levels of released virus. Cell lysates were analyzed by radioimmunoprecipitation assay according to the protocol described previously (Waheed A A et al, *Methods Mol. Biol.* 485, 163-84 (2009)). Briefly, 48 hours posttransfection, cells were starved in Met/Cys-free RPMI medium for 30 min and metabolically labeled with [$^{35}$S] Met/Cys-Pro-mix (Amersham) for 4 h. Cells lysates were prepared and immunoprecipitated with pooled immunoglobulin from HIV-1-infected patients (HIV-Ig; NIH AIDS Research and Reference Reagent Program). Immunoprecipitated proteins were separated on 12% acrylamide gels by SDS-PAGE; gels were exposed to a phosphorimager plate (Kodak or Fuji) and bands quantified by Quantity One software (Bio-Rad). Total HIV-1 Gag protein was measured (55 kDa Gag precursor+capsid p24/p25) and values were normalized with virus control (no siRNA co-transfected with pNL4-3).

Transfection Experiments with Anti-GSTP1 Auto-Recognizing R/DNA Hybrids and Immunoblotting.

A549 lung adenocarcinoma cells at 60% confluence were transfected with 25 nmols of R/DNA hybrid 1 or 2 using HiPerfect transfection reagent (Qiagen, Valencia, Calif.) using manufacturer's protocol. 24-h after addition of the first hybrid, the complement hybrid was co-transfected using the same protocol. Cells were collected and processed for immunoblotting using standard protocol 24 h later. Anti-GSTP1 antibody was from Cell Signaling Technology, and β-actin antibody from Abcam.

Sensitized Emission Method

1) Two fluorescent probes were used, Alexa488 (G for green) and Alexa546 (R for Red). The upper case letters G and R will be used to abbreviate the probes themselves, while lower case letters refer to their corresponding excitation (488 nm for Alexa488 and 561 nm for Alexa546) and emission wavelengths (between 493 and 557 nm for Alexa488 and between 566 and 680 nm for Alexa546) as described below.

2) For each sample, 3 images were taken. The first 2 were taken simultaneously using a 488 excitation (g) with two collecting emission channels, one between 493 and 557 nm for g (gg, first image) and another between 566 and 680 nm for r (gr, second image corresponding to the sensitized emission plus bleed through). A third image was taken just after using a 561 excitation (r) with a collecting emission between 566 and 680 nm for r (m, third image).

For samples containing the two probes, the signal, S at a given pixel in the sensitized emission image (gr), can be described by the following equation $$S_{gr}^{sample} = F + B_{gr}^G \times G_{gg}^{sample} + B_{gr}^R \times R_{rr}^{sample} \qquad \text{(Equation 1)},$$

where the first letter of the subscript refers to the excitation wavelength used and the second one to the emission wavelength collected (example: gr stands for green excitation at 488 nm and red emission between 566 and 680 nm). The superscript sample means that this value is sample dependent. F is the FRET signal at the given pixel. The subscripts of G and R refer to Alexa488 and Alexa546 respectively. $B_{gr}^{G}$ is the bleed through of Alexa488 into the Alexa546 emission channel when excited at 488 nm. Likewise $B_{gr}^{R}$ is the bleed through of Alexa546 into the Alexa488 emission channel when excited at 488 nm. Those bleed through correction factors are constants measured separately as described below. $G_{gg}^{sample}$ the intensity from Alexa488 when excited with 488 and emitted light from 493 to 557 nm is collected. Likewise, $R_{rr}^{sample}$ is the intensity from alexa546 when excited with 561 nm and emitted light from 566 and 680 nm is collected. $G_{gg}^{sample}$ and $R_{rr}^{sample}$ are sample dependent and correspond to the signal from the first image and third image respectively.

For the first image, equation 1 simplifies as follows $S_{GG}^{sample}=G_{GG}^{sample}$.

For the third image, equation 1 simplifies as follows $S_{RR}^{sample}=R_{RR}^{sample}$.

The two bleed through correction factors are calculated from different samples containing only Alexa488 or only Alexa546.

On samples containing only Alexa488, equation 1 simplifies as follows For the first image, $S_{gg}^{sample}=G_{gg}^{sample}$ For the second image, $S_{gr}^{sample}=B_{gr}^{G} \times G_{gg}^{sample}$ By taking the ratio of the two we obtain $B_{gr}^{G}=S_{gr}^{sample}/S_{gg}^{sample}$ On samples containing only Alexa546, equation 1 simplifies as follows For the third image, $S_{rr}^{sample}=R_{rr}^{sample}$ For the second image, $S_{gr}^{sample}=B_{gr}^{R} \times R_{gr}^{sample}$ By taking the ratio of the two we obtain $B_{gr}^{R}=S_{gr}^{sample}/S_{rr}^{sample}$ 4) All images were collected under the same confocal microscope settings, and background signal was subtracted before performing the above calculations.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

---

What is claimed is:

1. An R/DNA chimeric polyfunctional nanoparticle (R/DNA NP) comprising at least two complementary auto-recognizing chimeric nanoparticles,
   said first chimeric nanoparticle comprising a first DNA oligonucleotide that is hybridized along its length to one or more complementary first RNA oligonucleotides,
   said second chimeric nanoparticle comprising a second DNA oligonucleotide that is hybridized along its length to one or more complementary second RNA oligonucleotides,
   wherein the first DNA oligonucleotide is complementary to the second DNA oligonucleotide and the first RNA oligonucleotides are complementary to the second RNA oligonucleotides,
   wherein the first DNA oligonucleotide comprises a 5' toehold sequence and the second DNA oligonucleotide comprises a 3' toehold sequence that is complementary to the 5' toehold sequence, and
   wherein a DNA duplex and one or more functional RNA duplexes are formed upon the hybridization of the 5' and 3' toeholds and the subsequent reassociation of the complementary first and second RNA oligonucleotides.

2. The R/DNA chimeric polyfunctional nanoparticles of claim 1, wherein the one or more functional RNA duplexes is a Dicer substrate which can be converted by dicing to an siRNA molecule which inhibits one or more target RNAs.

3. The R/DNA chimeric polyfunctional nanoparticles of claim 2, wherein the one or more target RNAs produce a therapeutically beneficial result when inhibited.

4. The R/DNA chimeric polyfunctional nanoparticles of claim 2, wherein the one or more target RNAs encode proteins involved in a disease process or a portion thereof.

5. The R/DNA chimeric polyfunctional nanoparticles of claim 1, wherein the one or more target RNAs encode an apoptosis inhibitor protein.

6. The R/DNA chimeric polyfunctional nanoparticles of claim 5, wherein the apoptosis inhibitor protein is selected from the group consisting of BCL-2, FLIP, STAT3, and XIAP.

7. The R/DNA chimeric polyfunctional nanoparticles of claim 1, wherein the target RNA is a pathogenic RNA genome, an RNA transcript derived from the genome of the pathogenic agent, or a portion thereof.

8. The R/DNA chimeric polyfunctional nanoparticles of claim 1, wherein the first chimeric nanoparticle comprises a first functional moiety.

9. The R/DNA chimeric polyfunctional nanoparticles of claim 8, wherein the second chimeric nanoparticle comprises a second functional moiety.

10. A composition comprising an R/DNA chimeric polyfunctional nanoparticle of claim 1.

11. A pharmaceutical composition comprising an R/DNA chimeric polyfunctional nanoparticle of any of claim 1.

12. The pharmaceutical composition of claim 11 further comprising a pharmaceutically acceptable excipient, carrier, or diluent.

13. A method of inhibiting the expression of an HIV-1 or cancer gene in a cell comprising contacting the cell with an effective amount of the R/DNA chimeric polyfunctional nanoparticle of claim 2, and wherein the Dicer substrate may be converted to an siRNA by dicing which inhibits the expression of the HIV-1 or cancer gene.

14. A kit comprising the R/DNA chimeric polyfunctional nanoparticle of claim 1.

15. The R/DNA chimeric polyfunctional nanoparticle of claim 8, wherein first functional moiety is a FRET fluorescence moiety.

16. The R/DNA chimeric polyfunctional nanoparticle of claim 8, wherein second functional moiety is a FRET fluorescence moiety.

17. The R/DNA chimeric polyfunctional nanoparticle of claim 1, wherein the one or more functional RNA duplexes formed upon reassociation are each Dicer substrates capable of forming siRNAs.

18. The R/DNA chimeric polyfunctional nanoparticle of claim 17, wherein the siRNAs silence the same target RNA or different target RNAs.

19. The R/DNA chimeric polyfunctional nanoparticle of claim 1, wherein the one or more functional RNA duplexes formed upon reassociation comprise at least one Dicer substrate and at least one additional functionality.

20. The R/DNA chimeric polyfunctional nanoparticle of claim 19, wherein the at least one additional functionality is an RNA aptamer.

21. The R/DNA chimeric polyfunctional nanoparticle of claim 20, wherein the RNA aptamer is a Malachite Green RNA aptamer which produces a fluorescent signal upon formation of the RNA duplex.

22. The R/DNA chimeric polyfunctional nanoparticle of claim 1, wherein the first and second DNA oligonucleotides each contain complementary second 5' or 3' toehold sequences to provide complementary toehold sequences at both ends of the first and second chimeric nanoparticles.

* * * * *